United States Patent
Kinsho et al.

(10) Patent No.: US 7,638,256 B2
(45) Date of Patent: Dec. 29, 2009

(54) FLUORINATED CYCLIC STRUCTURE-BEARING SILICON COMPOUNDS AND SILICONE RESINS, RESIST COMPOSITIONS USING THE SAME, AND PATTERNING PROCESS

(75) Inventors: Takeshi Kinsho, Joetsu (JP); Takeru Watanabe, Joetsu (JP); Mutsuo Nakashima, Joetsu (JP); Yoshitaka Hamada, Joetsu (JP)

(73) Assignee: Shin-Etsu Chemical Co., Ltd., Tokyo (JP)

(*) Notice: Subject to any disclaimer, the term of this patent is extended or adjusted under 35 U.S.C. 154(b) by 574 days.

(21) Appl. No.: 11/480,944

(22) Filed: Jul. 6, 2006

(65) Prior Publication Data

US 2007/0009832 A1    Jan. 11, 2007

(30) Foreign Application Priority Data

Jul. 7, 2005 (JP) .................... 2005-198609

(51) Int. Cl.
G03F 7/039 (2006.01)
G03F 7/038 (2006.01)
G03F 7/20 (2006.01)
G03F 7/30 (2006.01)
G03F 7/38 (2006.01)

(52) U.S. Cl. .............. 430/270.1; 430/325; 430/326; 430/905; 430/907; 549/214; 549/356; 549/357; 549/369; 549/416; 549/417; 549/423; 549/427; 549/428; 549/429; 549/475; 549/476; 549/497; 549/502; 549/504

(58) Field of Classification Search ............ None
See application file for complete search history.

(56) References Cited

U.S. PATENT DOCUMENTS

| | | |
|---|---|---|
| 5,714,625 A | 2/1998 | Hada et al. |
| 5,972,560 A | 10/1999 | Kaneko et al. |
| 6,004,724 A | 12/1999 | Yamato et al. |
| 6,063,953 A | 5/2000 | Hada et al. |
| 6,261,738 B1 | 7/2001 | Asakura et al. |
| 6,512,020 B1 | 1/2003 | Asakura et al. |
| 6,730,453 B2 | 5/2004 | Nakashima et al. |
| 6,908,722 B2 | 6/2005 | Ebata et al. |
| 2002/0012871 A1 | 1/2002 | Hatakeyama et al. |
| 2002/0085165 A1 | 7/2002 | Fukumoto et al. |
| 2003/0157430 A1 | 8/2003 | Yoon et al. |
| 2003/0170561 A1 | 9/2003 | Iwasawa et al. |
| 2004/0143082 A1 | 7/2004 | Iwasawa et al. |
| 2006/0093960 A1* | 5/2006 | Kinsho et al. ............ 430/270.1 |
| 2007/0218402 A1* | 9/2007 | Kinsho et al. ............ 430/270.1 |

FOREIGN PATENT DOCUMENTS

| | | |
|---|---|---|
| EP | 1 398 339 A1 | 3/2004 |
| JP | 9-95479 A | 4/1997 |
| JP | 9-208554 A | 8/1997 |
| JP | 9-230588 A | 9/1997 |
| JP | 10-324748 A | 12/1998 |
| JP | 11-302382 A | 11/1999 |
| JP | 2000-314956 A | 11/2000 |
| JP | 2001-215714 A | 8/2001 |
| JP | 2002-55346 A | 2/2002 |
| JP | 2002-220471 A | 8/2002 |
| JP | 2002-268227 A | 9/2002 |
| JP | 2002-278073 A | 9/2002 |
| JP | 2003-20335 A | 1/2003 |
| JP | 2003-173027 A | 6/2003 |
| JP | 2004-313762 A | 11/2004 |

OTHER PUBLICATIONS

H. Ito, et al., "Fluropolymers for 157/193 nm Lithography: Chemistry, New Platform, Formulation Strategy, and Lithographic Evaluation", Journal of Photopolymer Science and Technology, Nov. 4, 2002, pp. 591-602, vol. 15.

European Office Action dated Nov. 23, 2006 issued in corresponding European patent application No. 06253485.4.

H. Ito et al.; "Fluoropolymers for 157/193 nm Lithography: Chemistry, New Platform, Formulation Strategy, and Lithographic Evaluation"; Journal of Photopolymer Science and Technology, vol. 15, No. 4, pp. 591-602, 2002. Cited in the Specification.

Cheng-Ping Qian et al.; "Perfluoro-Enolate Chemistry: Facile Generation and Unique Reactivities of Metal F-1-Propen-2-Olates"; Tetrahedron Letters, vol. 29, No. 33, pp. 4119-4122, 1988.

T. Hiyama; "Organofluorine Compounds—Chemistry and Applications", Reagents for Fluorination, pp. 39-47, 2000.

Cheng-Ping Qian et al.; Generation and use of Lithium Pentafluorophopen-2-Olate: 4-Hydroxy-1,1,1,3,3-Pentafluoro-2-Hexanone Hydrate (2,2,4-Hexanetriol, 1,1,1,3,3-pentafluoro- from 1-Propen-2-ol, 1,1,3,3,3-pentafluro-, lithium salt); Organic Synthesis, vol. 76, pp. 151-158, 1997.

* cited by examiner

*Primary Examiner*—Sin J. Lee
(74) *Attorney, Agent, or Firm*—Westerman, Hattori, Daniels & Adrian, LLP

(57) ABSTRACT

Silicon compounds having fluorinated hemiacetal structure are provided. Silicone resins having the same structure have an appropriate acidity to enable formation of a finer pattern by minimizing the pattern collapse by swelling, exhibit improved resistance to the etching used in the pattern transfer to an organic film, and are thus suited for use in resist compositions for the bilayer process.

11 Claims, No Drawings

FLUORINATED CYCLIC STRUCTURE-BEARING SILICON COMPOUNDS AND SILICONE RESINS, RESIST COMPOSITIONS USING THE SAME, AND PATTERNING PROCESS

CROSS-REFERENCE TO RELATED APPLICATION

This non-provisional application claims priority under 35 U.S.C. §119(a) on Patent Application No. 2005-198609 filed in Japan on Jul. 7, 2005, the entire contents of which are hereby incorporated by reference.

This invention relates to silicon compounds and silicone resins useful as a base resin in chemically amplified positive resist compositions for use in the micropatterning step of the semiconductor device manufacturing process. More particularly, it relates to silicon compounds and silicone resins useful as a base resin in resist compositions intended for the photolithography using deep-ultraviolet or the lithography using x-ray or electron beam, especially positive resist compositions intended for the bilayer resist process; resist compositions using the same; and a patterning process using the resist compositions.

BACKGROUND OF THE INVENTION

In the drive for higher integration and operating speeds in LSI devices, the pattern rule is made drastically finer. Under the miniaturizing trend, the lithography has achieved formation of finer patterns by using a light source with a shorter wavelength and by a choice of a proper resist composition for the shorter wavelength. Predominant among others are positive resist compositions which are used as a single layer. These single layer positive resist compositions are based on resins possessing a skeleton having resistance to etching with chlorine or fluorine gas plasma and provided with a resist mechanism that exposed areas become dissolvable. Typically, the resist composition is coated on a substrate to be processed and exposed to a pattern of light, after which the exposed areas of the resist coating are dissolved to form a pattern. Then, the substrate can be processed by etching with the remaining resist pattern serving as an etching mask.

In an attempt to achieve a finer feature size, i.e., to reduce the pattern width with the thickness of a resist coating kept unchanged, the resist coating becomes low in resolution performance. If the resist coating is developed with a liquid developer to form a pattern, the so-called "aspect ratio" (depth/width) of the resist pattern becomes too high, resulting in pattern collapse. For this reason, the miniaturization is accompanied by a thickness reduction of the resist coating (thinner coating). On the other hand, with the progress of the exposure wavelength toward a shorter wavelength, the resin in resist compositions is required to have less light absorption at the exposure wavelength. In response to changes from i-line to KrF and to ArF, the resin has made a transition from novolac resins to polyhydroxystyrene and to acrylic resins. Actually, the etching rate under the above-indicated etching conditions has been accelerated. This suggests the inevitableness that a substrate to be processed is etched through a thinner resist coating having weaker etching resistance. It is urgently required to endow the resist coating with etching resistance.

Meanwhile, a process known as multilayer resist process was developed in the art for processing a substrate by etching. The process uses a resist coating which has weak etching resistance under the etching conditions for the substrate, but is capable of forming a finer pattern, and an intermediate coating which has resistance to etching for processing the substrate and can be patterned under the conditions to which the resist coating is resistant. Once the resist pattern is transferred to the intermediate coating, the substrate is processed by etching through the pattern-transferred intermediate coating as an etching mask. A typical process uses a silicon-containing resin as the resist composition and an aromatic resin as the intermediate coating. In this process, after a pattern is formed in the silicon-containing resin, oxygen-reactive ion etching is carried out. Then the silicon-containing resin is converted to silicon oxide having high resistance to oxygen plasma etching, and at the same time, the aromatic resin is readily etched away where the etching mask of silicon oxide is absent, whereby the pattern of the silicon-containing resin is transferred to the aromatic resin layer. Unlike the single layer resist coating, the aromatic resin need not have light transmittance at all, allowing for use of a wide variety of aromatic resins having high resistance to etching with fluorine or chlorine gas plasma. Using the aromatic resin as the etching mask, the substrate to be processed can be etched with fluorine or chlorine gas plasma.

With respect to the bilayer resist process, active studies were made on the exposure to the radiation (193 nm) of ArF excimer laser and radiation of shorter wavelength where aromatic resins can be no longer used, and several reports have already been made. For example, JP-A 10-324748 and JP-A 11-302382 disclose a siloxane polymer having carboxyl group-containing, non-aromatic monocyclic or polycyclic hydrocarbon groups or bridged cyclic hydrocarbon groups on side chains wherein at least some of the carboxyl groups are substituted with acid labile groups, for example, a siloxane polymer in which a norbornyl group having a t-butoxycarbonyl group at 5-position is bonded to a silicon atom, and a resist composition comprising the polymer. Allegedly this resist composition is less absorptive to KrF (248 nm) excimer laser or ArF excimer laser radiation, forms a pattern of good profile, and is improved in sensitivity, resolution and dry etching resistance. Also, JP-A 2002-055346 and JP-A 2002-268227 disclose that silicone-containing polymers having fluorinated alcohol incorporated therein are less absorptive at the wavelength (157 nm) of $F_2$ laser and improved in sensitivity, resolution and plasma etching resistance.

For the technology intended to improve resolution by reducing the wavelength of an exposure light source, there have been reported compositions using fluorinated siloxane polymers having less absorption at the exposure wavelength of $F_2$ laser. For example, JP-A 2002-220471 discloses that a radiation-sensitive resin composition comprising a polysiloxane having a specific acid-assisted leaving group linked to a silicon atom via at least two norbornane rings is useful in that it is improved in dry etching resistance and highly transparent to the radiation of $F_2$ laser. With respect to the technique of improving resolution by forming a thinner coating of material, JP-A 2001-215714 discloses that a silicon-containing polymer having a viscosity in a specific range enables to form a thinner resist coating while maintaining in-plane uniformity in the resist coating.

Among the recent studies on single layer resist coatings where attempts were made to form a finer pattern, it was reported as the cause of pattern collapse that the polymer undergoes substantial swelling immediately before dissolution during development, which inhibits formation of a finer pattern. One effective measure for preventing such swell is to introduce a unit containing a hydroxyl group having a phenol-like acidity due to fluorine substitution at proximate positions, into a resin as a polar group for thereby imparting an appropriate alkali solubility to the resin. See H. Ito et al., Journal of Photopolymer Science and Technology, Vol. 15, No. 4 (2002), 591-602. The pattern collapse is a common problem to silicon-containing resist compositions comprising silicone resins as a base polymer. There is a possibility that the high resolution of the aforementioned polysiloxane polymer be accompanied by this effect.

However, in an actual practice, an attempt to transfer a pattern to an aromatic resin organic coating using a fluorine-rich resin as an etching mask revealed that its resistance to oxygen-reactive etching is far below the expectation. There is a need for further improvement in resistance to etching under these conditions.

Prior Art 1: JP-A 10-324748
Prior Art 2: JP-A 11-302382
Prior Art 3: JP-A 2002-055346
Prior Art 4: JP-A 2002-268227
Prior Art 5: JP-A 2002-220471
Prior Art 6: JP-A 2001-215714
Prior Art 7: JP-A 2002-278073
Prior Art 8: JP-A 2003-20335
Prior Art 9: JP-A 2003-173027
Prior Art 10: H. Ito et al., Journal of Photopolymer Science and Technology, Vol. 15, No. 4 (2002), 591-602

DISCLOSURE OF THE INVENTION

An object of the present invention is to provide a silicon compound or a silicone resin for use in a silicone resin-containing resist composition for the bilayer process, which has an appropriate acidity to enable formation of a finer pattern by minimizing the pattern collapse by swelling, which exhibits improved resistance to the etching used in the pattern transfer to an underlying organic film, and which can achieve the appropriate acidity by a smaller number of fluorine substitution; a resist composition comprising the silicone resin; and a patterning process using the resist composition.

The inventor has found that silicon compounds bearing a fluorinated cyclic structure having an appropriate phenol-like acidity, as represented by the general formula (1), (2), (3) or (4), shown below, and fluorinated cyclic structure-bearing silicone resins comprising a partial structure having the general formula (1a), (2a), (3a) or (4a) can be prepared from currently available raw materials, and that using these, radiation-sensitive resist compositions having high transparency at a wavelength of up to 300 nm and excellent development properties are obtainable.

In one aspect, the present invention provides a silicon compound bearing a fluorinated cyclic structure, having the general formula (1):

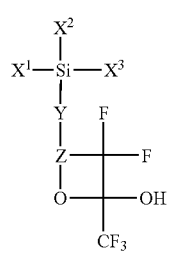

(1)

wherein $X^1$, $X^2$ and $X^3$ each are hydrogen atom, hydroxyl group, halogen atom, a straight, branched or cyclic alkoxy group of 1 to 6 carbon atoms, or a monovalent organic group of 1 to 20 carbon atoms having a straight, branched, cyclic or polycyclic skeleton (excluding alkoxy), Y is a single bond or a divalent organic group, and Z is a trivalent organic group.

The invention also provides a silicon compound bearing a fluorinated cyclic structure, having the general formula (2), (3) or (4).

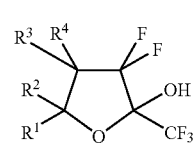

(2)

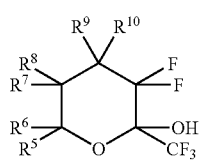

(3)

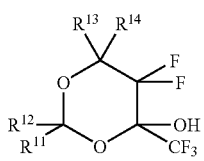

(4)

Herein at least one of $R^1$, $R^2$, $R^3$ and $R^4$ is a silicon-containing substituent group of the general formula:

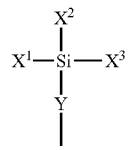

wherein $X^1$, $X^2$ and $X^3$ each are hydrogen atom, hydroxyl group, halogen atom, a straight, branched or cyclic alkoxy group of 1 to 6 carbon atoms, or a monovalent organic group of 1 to 20 carbon atoms having a straight, branched, cyclic or polycyclic skeleton (excluding alkoxy), and Y is a single bond or a divalent organic group, and each of the remaining $R^1$ to $R^4$ is independently hydrogen, hydroxyl, halogen, or a monovalent organic group of 1 to 20 carbon atoms having a straight, branched, cyclic or polycyclic skeleton, or a combination of any two or more of $R^1$, $R^2$, $R^3$ and $R^4$ may bond together to form a ring with the carbon atom or atoms to which they are attached;

at least one of $R^5$, $R^6$, $R^7$, $R^8$, $R^9$ and $R^{10}$ is a silicon-containing substituent group of the general formula:

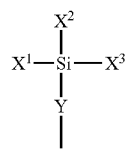

wherein $X^1$, $X^2$ and $X^3$ each are hydrogen atom, hydroxyl group, halogen atom, a straight, branched or cyclic alkoxy group of 1 to 6 carbon atoms, or a monovalent organic group of 1 to 20 carbon atoms having a straight, branched, cyclic or polycyclic skeleton (excluding alkoxy), and Y is a single bond or a divalent organic group, and each of the remaining $R^5$ to $R^{10}$ is independently hydrogen, hydroxyl, halogen, or a monovalent organic group of 1 to 20 carbon atoms having a straight, branched, cyclic or polycyclic skeleton, or a combination of any two or more of $R^5$ to $R^{10}$ may bond together to form a ring with the carbon atom or atoms to which they are attached;

at least one of $R^{11}$, $R^{12}$, $R^{13}$ and $R^{14}$ is a silicon-containing substituent group of the general formula:

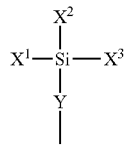

wherein $X^1$, $X^2$ and $X^3$ each are hydrogen atom, hydroxyl group, halogen atom, a straight, branched or cyclic alkoxy group of 1 to 6 carbon atoms, or a monovalent organic group of 1 to 20 carbon atoms having a straight, branched, cyclic or polycyclic skeleton (excluding alkoxy), and Y is a single bond or a divalent organic group, and each of the remaining $R^{11}$ to $R^{14}$ is independently hydrogen atom, hydroxyl group, halogen atom, or a monovalent organic group of 1 to 20 carbon atoms having a straight, branched, cyclic or polycyclic skeleton, or a combination of any two or more of $R^{11}$, $R^{12}$, $R^{13}$ and $R^{14}$ may bond together to form a ring with the carbon atom or atoms to which they are attached.

In formulae (1) to (4), Y is preferably a divalent organic group having aliphatic ring, and more preferably a divalent organic group having the general formula:

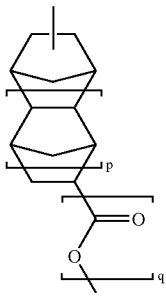

wherein p and q are each independently 1 or 0.

In a second aspect, the invention provides a fluorinated cyclic structure-bearing silicone resin comprising a partial structure having the general formula (1a), (2a), (3a) or (4a).

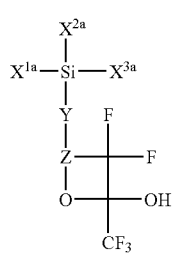

(1a)

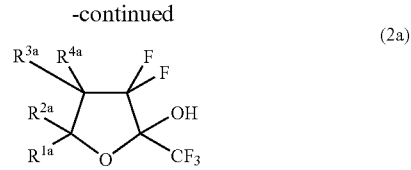

(2a)

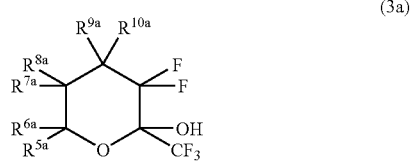

(3a)

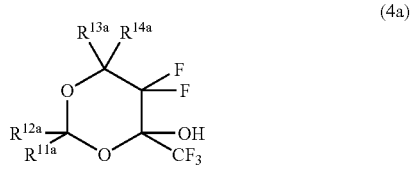

(4a)

Herein Y is a single bond or a divalent organic group, Z is a trivalent organic group, at least one of $X^{1a}$, $X^{2a}$ and $X^{3a}$ is an oxygen atom, and the remaining is hydrogen atom, hydroxyl group, halogen atom, a straight, branched or cyclic alkoxy group of 1 to 6 carbon atoms, or a monovalent organic group of 1 to 20 carbon atoms having a straight, branched, cyclic or polycyclic skeleton (excluding alkoxy), at least one of $R^{1a}$, $R^{2a}$, $R^{3a}$ and $R^{4a}$ is a silicon-containing substituent group of the general formula:

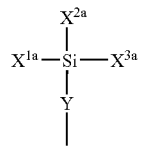

wherein at least one of $X^{1a}$, $X^{2a}$ and $X^{3a}$ is an oxygen atom and the remaining is hydrogen atom, hydroxyl group, halogen atom, a straight, branched or cyclic alkoxy group of 1 to 6 carbon atoms, or a monovalent organic group of 1 to 20 carbon atoms having a straight, branched, cyclic or polycyclic skeleton (excluding alkoxy), and Y is as defined above, and each of the remaining $R^{1a}$ to $R^{4a}$ is independently hydrogen atom, hydroxyl group, halogen atom, or a monovalent organic group of 1 to 20 carbon atoms having a straight, branched, cyclic or polycyclic skeleton, or a combination of any two or more of $R^{1a}$ to $R^{4a}$ may bond together to form a ring with the carbon atom or atoms to which they are attached;

at least one of $R^{5a}$, $R^{6a}$, $R^{7a}$, $R^{8a}$, $R^{9a}$ and $R^{10a}$ is a silicon-containing substituent group of the general formula:

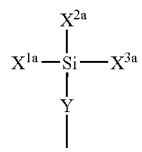

wherein at least one of $X^{1a}$, $X^{2a}$ and $X^{3a}$ is an oxygen atom and the remaining is hydrogen atom, hydroxyl group, halogen atom, a straight, branched or cyclic alkoxy group of 1 to 6 carbon atoms, or a monovalent organic group of 1 to 20 carbon atoms having a straight, branched, cyclic or polycyclic skeleton (excluding alkoxy), and Y is as defined above, and each of the remaining $R^{5a}$ to $R^{10a}$ is independently hydrogen atom, hydroxyl group, halogen atom, or a monovalent organic group of 1 to 20 carbon atoms having a straight, branched, cyclic or polycyclic skeleton, or a combination of any two or more of $R^{5a}$ to $R^{10a}$ may bond together to form a ring with the carbon atom or atoms to which they are attached;

at least one of $R^{11a}$, $R^{12a}$, $R^{13a}$ and $R^{14a}$ is a silicon-containing substituent group of the general formula:

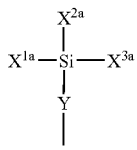

wherein at least one of $X^{1a}$, $X^{2a}$ and $X^{3a}$ is an oxygen atom and the remaining is hydrogen atom, hydroxyl group, halogen atom, a straight, branched or cyclic alkoxy group of 1 to 6 carbon atoms, or a monovalent organic group of 1 to 20 carbon atoms having a straight, branched, cyclic or polycyclic skeleton (excluding alkoxy), and Y is as defined above, and each of the remaining $R^{11a}$ to $R^{14a}$ is independently hydrogen atom, hydroxyl group, halogen atom, or a monovalent organic group of 1 to 20 carbon atoms having a straight, branched, cyclic or polycyclic skeleton, or a combination of any two or more of $R^{11a}$ to $R^{14a}$ may bond together to form a ring with the carbon atom or atoms to which they are attached;

In a third aspect, the invention provides a resist composition comprising (A) the silicone resin defined above, (B) a photoacid generator, and (C) a solvent.

In a fourth aspect, the invention provides a patterning process comprising the steps of applying the resist composition onto a substrate to form a resist layer; heat treating the resist layer and exposing it to high energy radiation having a wavelength of up to 300 nm or electron beam through a photomask; and optionally heat treating the exposed resist layer, and developing it with a developer.

BENEFITS OF THE INVENTION

The silicon compound or silicone resin of the invention has an appropriate acidity to enable formation of a finer pattern by minimizing the pattern collapse by swelling, exhibits improved resistance to the etching used in the pattern transfer to an underlying organic film, and can achieve the appropriate acidity by a smaller number of fluorine substitution. The silicone resin is suited for use in a resist composition for the bilayer process involving ArF exposure. The resist composition is effective for preventing a pattern formed thereof from being collapsed by swelling and exhibits improved resistance to etching with an oxygen-base gas plasma.

DESCRIPTION OF THE PREFERRED EMBODIMENTS

Silicon Compound

In one embodiment of the invention, the silicon compounds having a fluorinated cyclic structure are those having a fluorinated hemiacetal structure represented by the general formula (1).

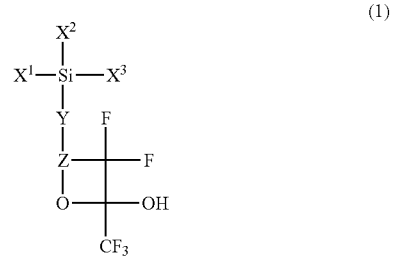

In formula (1), $X^1$, $X^2$ and $X^3$ each are a hydrogen atom, a hydroxyl group, a halogen atom, a straight, branched or cyclic alkoxy group of 1 to 6 carbon atoms, or a monovalent organic group of 1 to 20 carbon atoms having a straight, branched, cyclic or polycyclic skeleton (excluding alkoxy), Y is a single bond or a divalent organic group, and Z is a trivalent organic group.

For stability and ease of preparation, the hemiacetal structure is preferably a 5-membered or 6-membered ring hemiacetal structure. More preferred are compounds of oxolane, oxane and dioxane hemiacetal structures having the general formulae (2), (3) and (4), respectively.

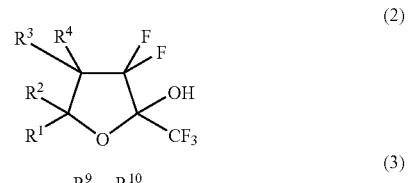

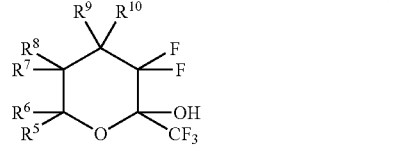

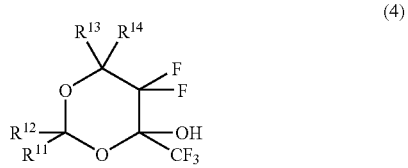

Herein at least one of $R^1$, $R^2$, $R^3$ and $R^4$, preferably one, is a silicon-containing substituent group of the general formula:

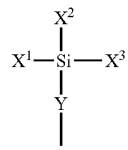

wherein $X^1$, $X^2$ and $X^3$ each are a hydrogen atom, a hydroxyl group, a halogen atom, a straight, branched or cyclic alkoxy group of 1 to 6 carbon atoms, or a monovalent organic group of 1 to 20 carbon atoms having a straight, branched, cyclic or polycyclic skeleton (excluding alkoxy), and Y is a single bond or a divalent organic group, and the remaining $R^1$ to $R^4$ are each independently a hydrogen atom, a hydroxyl group, a halogen atom, or a monovalent organic group of 1 to 20 carbon atoms having a straight, branched, cyclic or polycyclic skeleton, or a combination of any two or more of $R^1$, $R^2$, $R^3$ and $R^4$ may bond together to form a ring with the carbon atom or atoms to which they are attached.

At least one of $R^5$, $R^6$, $R^7$, $R^8$, $R^9$ and $R^{10}$, preferably one, is a silicon-containing substituent group of the general formula:

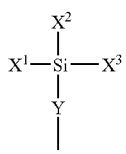

wherein $X^1$, $X^2$ and $X^3$ each are a hydrogen atom, a hydroxyl group, a halogen atom, a straight, branched or cyclic alkoxy group of 1 to 6 carbon atoms, or a monovalent organic group of 1 to 20 carbon atoms having a straight, branched, cyclic or polycyclic skeleton (excluding alkoxy), and Y is a single bond or a divalent organic group, and the remaining $R^5$ to $R^{10}$ are each independently a hydrogen atom, a hydroxyl group, a halogen atom, or a monovalent organic group of 1 to 20 carbon atoms having a straight, branched, cyclic or polycyclic skeleton, or a combination of any two or more of $R^5$, $R^6$, $R^7$, $R^8$, $R^9$ and $R^{10}$ may bond together to form a ring with the carbon atom or atoms to which they are attached.

At least one of $R^{11}$, $R^{12}$, $R^{13}$ and $R^{14}$, preferably one, is a silicon-containing substituent group of the general formula:

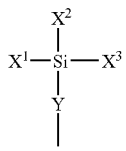

wherein $X^1$, $X^2$ and $X^3$ each are a hydrogen atom, a hydroxyl group, a halogen atom, a straight, branched or cyclic alkoxy group of 1 to 6 carbon atoms, or a monovalent organic group of 1 to 20 carbon atoms having a straight, branched, cyclic or polycyclic skeleton (excluding alkoxy), and Y is a single bond or a divalent organic group, and the remaining $R^{11}$ to $R^{14}$ are each independently a hydrogen atom, a hydroxyl group, a halogen atom, or a monovalent organic group of 1 to 20 carbon atoms having a straight, branched, cyclic or polycyclic skeleton, or a combination of any two or more of $R^{11}$, $R^{12}$, $R^{13}$ and $R^{14}$ may bond together to form a ring with the carbon atom or atoms to which they are attached.

It is generally believed that a hemiacetal structure (HA) is in equilibrium with a chain keto-alcohol compound (KA). It is said that in the case of a 5- or 6-membered ring, the equilibrium is biased toward the hemiacetal side, which has higher stability. The compound of hemiacetal structure (HA) having the general formula (2), (3) or (4) becomes predominant for the following reason. A corresponding chain keto-alcohol structure (KA) of the general formula (2'), (3') or (4'), shown below, has five fluorine atoms substituted on carbon atoms (α-carbon and α'-carbon) adjoining the carbonyl group. Due to the strong electron-withdrawing effect of these fluorine atoms, the carbon of the carbonyl group is more susceptible to attack by a nucleophilic agent than ordinary carbonyl groups. This allows for an intramolecular nucleophilic attack by the hydroxyl group of the chain keto-alcohol compound (KA). Thus the compound is more likely to take a stable hemiacetal structure (HA). Particularly in the case of dioxane hemiacetal structure of formula (4), the chain keto-alcohol compound (4') assumes an unstable chain hemiacetal structure, which structure is considered not to exist stable. Inversely stated, by taking a cyclic hemiacetal structure through cyclization, the compound (4) in which an acetal structure and a hemiacetal structure are co-present within the molecule exists stable.

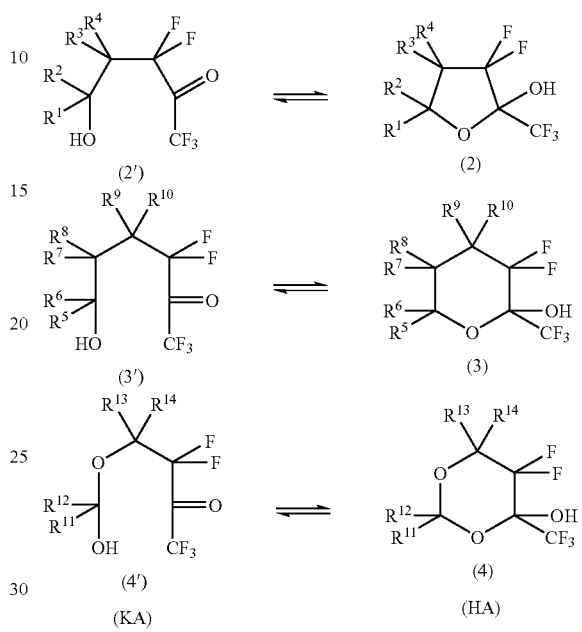

In these hemiacetal structures, five fluorine atoms are attached to the carbon atoms which bond to the carbon atom having the hydroxyl group attached, and due to the strong electron-withdrawing effect of these fluorine atoms, the oxygen of the hydroxyl group has a lower electron density. Then the hydroxyl group in these hemiacetal structures has a high acidity, as compared with the hydroxyl group in ordinary hemiacetal structures without fluorine substitution, imparting an appropriate alkali solubility to the resin.

At least one of $R^1$, $R^2$, $R^3$ and $R^4$ is a silicon-containing substituent group of the general formula:

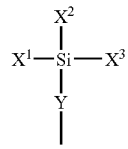

wherein $X^1$, $X^2$ and $X^3$ each are hydrogen, hydroxyl, halogen, a straight, branched or cyclic alkoxy group of 1 to 6 carbon atoms, or a monovalent organic group of 1 to 20 carbon atoms, preferably 1 to 8 carbon atoms, having a straight, branched, cyclic or polycyclic skeleton (excluding alkoxy), and Y is a single bond or a divalent organic group.

The remaining $R^1$ to $R^4$ are each independently hydrogen, hydroxyl, halogen, or a monovalent organic group of 1 to 20 carbon atoms, preferably 1 to 8 carbon atoms, having a straight, branched, cyclic or polycyclic skeleton. For the remaining groups, exemplary halogen atoms are fluorine, chlorine and bromine atoms. Examples of the monovalent organic group of 1 to 20 carbon atoms having a straight, branched, cyclic or polycyclic skeleton include monovalent hydrocarbon groups, for example, straight, branched or cyclic alkyl groups such as methyl, ethyl, propyl, isopropyl, n-butyl, sec-butyl, tert-butyl, tert-amyl, n-pentyl, n-hexyl, n-heptyl, n-octyl, n-nonyl, n-decyl, cyclopropyl, cyclobutyl, cyclopentyl, cyclopentylmethyl, cyclopentylethyl, cyclopentylbutyl, cyclohexyl, cyclohexylmethyl, cyclohexylethyl, cyclohexylbutyl, methylcyclohexylmethyl, ethylcyclohexylmethyl, ethylcyclohexylethyl, bicyclo[2.2.1]heptyl, bicyclo[2.2.1]heptylmethyl, bicyclo[2.2.1]heptylethyl, bicyclo[2.2.1]heptylbutyl, methylbicyclo[2.2.1]heptylmethyl, ethylbicyclo[2.2.1]heptylmethyl, ethylbicyclo[2.2.1]heptylethyl, bicyclo[2.2.2]octyl, bicyclo[2.2.2]octylmethyl, bicyclo[2.2.2]octylethyl, bicyclo[2.2.2]octylbutyl, methylbicyclo[2.2.2]octylmethyl, ethylbicyclo[2.2.2]octylmethyl, ethylbicyclo[2.2.2]octylethyl, tricyclo[5.2.1.0$^{2,6}$]decyl, tricyclo[5.2.1.0$^{2,6}$]decylmethyl, tricyclo[5.2.1.0$^{2,6}$]decylethyl, tricyclo[5.2.1.0$^{2,6}$]decylbutyl, methyltricyclo[5.2.1.0$^{2,6}$]decylmethyl, ethyltricyclo[5.2.1.0$^{2,6}$]decylmethyl, ethyltricyclo[5.2.1.0$^{2,6}$]decylethyl, adamantyl, adamantylmethyl, adamantylethyl, adamantylbutyl, methyladamantylmethyl, ethyladamantylmethyl, ethyladamantylethyl, tetracyclo[4.4.0.1$^{2,5}$.1$^{7,10}$]dodecyl, tetracyclo[4.4.0.1$^{2,5}$.1$^{7,10}$]dodecylmethyl, tetracyclo[4.4.0.1$^{2,5}$.1$^{7,10}$]dodecylethyl, tetracyclo[4.4.0.1$^{2,5}$.1$^{7.10}$]dodecylbutyl, methyltetracyclo[4.4.0.1$^{2,5}$.1$^{7,10}$]dodecylmethyl, ethyltetracyclo[4.4.0.1$^{2,5}$.1$^{7,10}$]dodecylmethyl, and ethyltetracyclo[4.4.0.1$^{2,5}$.1$^{7,10}$]dodecylethyl; aryl groups such as phenyl, methylphenyl, naphthyl, anthryl, and phenanthryl; and aralkyl groups such as benzyl, diphenylmethyl and phenethyl; alkoxy groups such as methoxy, ethoxy and propoxy; and acyloxy groups such as formyloxy and acetoxy. Some of the hydrogen atoms on the foregoing groups may be replaced by halogen atoms, alkyl, aryl, alkoxy, alkoxycarbonyl or oxo groups, and the methylene moiety in the foregoing groups may be replaced by an oxygen atom. Inter alia, $R^1$, $R^2$, $R^3$, and $R^4$ are more preferably selected from hydrogen, hydroxyl, fluorine, methyl, ethyl and perfluoroalkyl groups, especially of 1 to 8 carbon atoms.

Any two or more of $R^1$, $R^2$, $R^3$ and $R^4$ taken together may form a ring with the carbon atom or atoms to which they are attached. Examples of the ring include cycloaliphatic hydrocarbon groups of 3 to 12 carbon atoms, such as cyclopropane, cyclobutane, cyclopentane, cyclohexane, bicyclo[2.2.1]heptane, bicyclo[2.2.2]octane, tricyclo[5.2.1.0$^{2,6}$]decane, adamantane, and tetracyclo[4.4.0.1$^{2,5}$1$^{7,10}$]dodecane as well as fused rings containing any. Some hydrogen atoms on the foregoing cycloaliphatic hydrocarbon groups may be replaced by halogen atoms, alkyl, aryl, alkoxy, alkoxycarbonyl or oxo groups, and the methylene moiety in the foregoing groups may be replaced by an oxygen atom.

For $R^5$, $R^6$, $R^7$, $R^8$, $R^9$, and $R^{10}$ and $R^{11}$, $R^{12}$, $R^{13}$ and $R^{14}$, those groups exemplified for $R^1$, $R^2$, $R^3$ and $R^4$ are similarly appropriate.

Y is a single bond or a divalent organic group. Illustrative organic groups are divalent organic groups of 1 to 20 carbon atoms, preferably 1 to 12 carbon atoms, having a straight, branched, cyclic or polycyclic skeleton. Suitable divalent organic groups are obtained from monovalent hydrocarbon groups by substituting a single bond for one hydrogen atom, while examples of suitable monovalent hydrocarbon groups include alkyl groups having a straight, branched, cyclic or polycyclic skeleton such as methyl, ethyl, propyl, isopropyl, n-butyl, sec-butyl, tert-butyl, tert-amyl, n-pentyl, n-hexyl, n-heptyl, n-octyl, n-nonyl, n-decyl, cyclopropyl, cyclobutyl, cyclopentyl, cyclopentylmethyl, cyclopentylethyl, cyclopentylbutyl, cyclohexyl, cyclohexylmethyl, cyclohexylethyl, cyclohexylbutyl, methylcyclohexylmethyl, ethylcyclohexylmethyl, ethylcyclohexylethyl, bicyclo[2.2.1]heptyl, bicyclo[2.2.1]heptylmethyl, bicyclo[2.2.1]heptylethyl, bicyclo[2.2.1]heptylbutyl, methylbicyclo[2.2.1]heptylmethyl, ethylbicyclo[2.2.1]heptylmethyl, ethylbicyclo[2.2.1]heptylethyl, bicyclo[2.2.2]octyl, bicyclo[2.2.2]octylmethyl, bicyclo[2.2.2]octylethyl, bicyclo[2.2.2]octylbutyl, methylbicyclo[2.2.2]octylmethyl, ethylbicyclo[2.2.2]octylmethyl, ethylbicyclo[2.2.2]octylethyl, tricyclo[5.2.1.0$^{2,6}$]decyl, tricyclo[5.2.1.0$^{2,6}$]decylmethyl, tricyclo[5.2.1.0$^{2,6}$]decylethyl, tricyclo[5.2.1.0$^{2,6}$]decylbutyl, methyltricyclo[5.2.1.0$^{2,6}$]decylmethyl, ethyltricyclo[5.2.1.0$^{2,6}$]decylmethyl, ethyltricyclo[5.2.1.0$^{2,6}$]decylethyl, adamantyl, adamantylmethyl, adamantylethyl, adamantylbutyl, methyladamantylmethyl, ethyladamantylmethyl, ethyladamantylethyl, tetracyclo[4.4.0.1$^{2,5}$.1$^{7,10}$]dodecyl, tetracyclo[4.4.0.1$^{2,5}$.1$^{7,10}$]dodecylmethyl, tetracyclo[4.4.0.1$^{2,5}$.1$^{7,10}$]dodecylethyl, tetracyclo[4.4.0.1$^{2,5}$.1$^{7,10}$]dodecylbutyl, tetracyclo[4.4.0.1$^{2,5}$.1$^{7,10}$]dodecylmethyl, ethyltetracyclo[4.4.0.1$^{2,5}$.1$^{7,10}$]dodecylmethyl, and ethyltetracyclo[4.4.0.1$^{2,5}$.1$^{7,10}$]dodecylethyl; aryl groups such as phenyl, tolyl, naphthyl, anthryl, and phenanthryl; and aralkyl groups such as benzyl, diphenylmethyl and phenethyl. Some of the hydrogen atoms on the foregoing groups may be replaced by halogen atoms, alkyl, aryl, alkoxy, alkoxycarbonyl or oxo groups, and the methylene moiety in the foregoing groups may be replaced by an oxygen atom.

Of these divalent organic groups, those groups containing a cycloaliphatic ring are more preferred. Suitable cycloaliphatic rings include cyclopentane, cyclohexane, bicyclo[2.2.1]heptane (or norbornane), bicyclo[2.2.2]octane, and tetracyclo[4.4.0.1$^{2,5}$1$^{7,10}$]dodecane (or tetracyclododecane). Inter alia, those groups containing bicyclo[2.2.1]heptane or tetracyclo[4.4.0.1$^{2,5}$.1$^{7,10}$]dodecane are especially preferred.

Of the groups containing bicyclo[2.2.1]heptane or tetracyclo[4.4.0.1$^{2,5}$.1$^{7,10}$]dodecane, divalent organic groups of the general formula shown below are even more preferred.

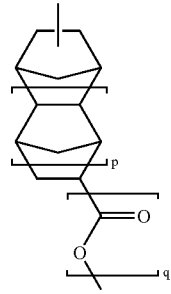

Herein, p and q are each independently 1 or 0. It is noted that this formula represents either one or both of the following.

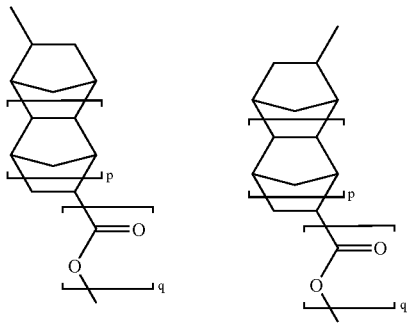

$X^1$, $X^2$ and $X^3$ each are a hydrogen atom, a hydroxyl group, a halogen atom, a straight, branched or cyclic alkoxy group of 1 to 6 carbon atoms, or a monovalent organic group of 1 to 20 carbon atoms having a straight, branched, cyclic or polycyclic skeleton (excluding alkoxy). In this regard, preferred halogen atoms are chlorine and bromine atoms. Examples of straight, branched or cyclic $C_1$-$C_6$ alkoxy groups include methoxy, ethoxy, propoxy, isopropoxy, butoxy, sec-butyloxy, pentyloxy, hexyloxy, cyclopentyloxy, cyclohexyloxy, methoxymethoxy, methoxyethoxy, methoxyethoxymethoxy, and methoxyethoxyethoxy. Examples of monovalent $C_1$-$C_{20}$ organic groups having a straight, branched, cyclic or polycyclic skeleton include straight, branched, cyclic or polycyclic alkyl groups such as methyl, ethyl, propyl, isopropyl, n-butyl, sec-butyl, tert-butyl, tert-amyl, n-pentyl, n-hexyl, n-heptyl, n-octyl, n-nonyl, n-decyl, cyclopropyl, cyclobutyl, cyclopentyl, cyclopentylmethyl, cyclopentylethyl, cyclopentylbutyl, cyclohexyl, cyclohexylmethyl, cyclohexylethyl, cyclohexylbutyl, methylcyclohexylmethyl, ethylcyclohexylmethyl, ethylcyclohexylethyl, bicyclo[2.2.1]heptyl, bicyclo[2.2.1]heptylmethyl, bicyclo[2.2.1]heptylethyl, bicyclo[2.2.1]heptylbutyl, methylbicyclo[2.2.1]heptylmethyl, ethylbicyclo[2.2.1]heptylmethyl, ethylbicyclo[2.2.1]heptylethyl, bicyclo[2.2.2]octyl, bicyclo[2.2.2]octylmethyl, bicyclo[2.2.2]octylethyl, bicyclo[2.2.2]octylbutyl, methylbicyclo[2.2.2]octylmethyl, ethylbicyclo[2.2.2]octylmethyl, ethylbicyclo[2.2.2]octylethyl, tricyclo[5.2.1.0$^{2,6}$]decyl, tricyclo[5.2.1.0$^{2,6}$]decylmethyl, tricyclo[5.2.1.0$^{2,6}$]decylethyl, tricyclo[5.2.1.0$^{2,6}$]decylbutyl, methyltricyclo[5.2.1.0$^{2,6}$]decylmethyl, ethyltricyclo[5.2.1.0$^{2,6}$]decylmethyl, ethyltricyclo[5.2.1.0$^{2,6}$]decylethyl, adamantyl, adamantylmethyl, adamantylethyl, adamantylbutyl, methyladamantylmethyl, ethyladamantylmethyl, ethyladamantylethyl, tetracyclo[4.4.0.1$^{2,5}$.1$^{7,10}$]dodecyl, tetracyclo[4.4.0.1$^{2,5}$.1$^{7,10}$]dodecylmethyl, tetracyclo[4.4.0.1$^{2,5}$.1$^{7,10}$]dodecylethyl, tetracyclo[4.4.0.1$^{2,5}$.1$^{7,10}$]dodecylbutyl, tetracyclo[4.4.0.1$^{2,5}$.1$^{7,10}$]dodecylmethyl, ethyltetracyclo[4.4.0.1$^{2,5}$.1$^{7,10}$]dodecylmethyl, and ethyltetracyclo[4.4.0.1$^{2,5}$.1$^{7,10}$]dodecylethyl; aryl groups such as phenyl, tolyl, naphthyl, anthryl, and phenanthryl; and aralkyl groups such as benzyl, diphenylmethyl and phenethyl. Some of the hydrogen atoms on the foregoing groups may be replaced by halogen atoms, alkyl, aryl, alkoxy, alkoxycarbonyl or oxo groups, and the methylene moiety in the foregoing groups may be replaced by an oxygen atom.

When $X^1$, $X^2$ and $X^3$ each are a hydrogen atom, a hydroxyl group, a halogen atom, or a straight, branched or cyclic $C_1$-$C_6$ alkoxy group (collectively referred to as "hydrolyzable substituent group," hereinafter), the silicon compound having such a fluorinated cyclic structure becomes a reaction substrate and serves as a silane monomer during cohydrolytic condensation reaction when a silicone resin is prepared therefrom as will be described later. Included are a silane monomer having one hydrolyzable substituent group (referred to as monofunctional silane monomer, hereinafter), a silane monomer having two hydrolyzable substituent groups (referred to as difunctional silane monomer, hereinafter), and a silane monomer having three hydrolyzable substituent groups (referred to as trifunctional silane monomer, hereinafter). Inter alia, di- and tri-functional silane monomers are preferred for the purpose of preparation of the silicone resin according to the invention. The hydrolyzable substituent groups in the molecule of silane monomers may be of the same type or two or more different types of hydrolyzable substituent groups may be included. Preferred hydrolyzable substituent groups are alkoxy groups, with methoxy and ethoxy being more preferred. When the mono- or di-functional silane monomer is used, the remaining two or one substituent group on silicon other than the hydrolyzable substituent groups is a monovalent organic group of 1 to 20 carbon atoms having a straight, branched, cyclic or polycyclic skeleton. Monovalent organic groups of up to 6 carbon atoms are preferred for ease of purification by distillation or the like, with alkyl of up to 6 carbon atoms, perfluoroalkyl of 1 to 8 carbon atoms, and phenyl are especially preferred.

In the fluorinated cyclic structure-bearing silicon compounds having the formula (1), (2), (3) or (4) according to the invention, depending on the type and combination of the groups represented by $X^1$, $X^2$, $X^3$, Y, Z, $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$, carbon atoms constituting the molecule can be asymmetric, and there can exist enantiomers and diastereomers. Each of formulae (1) to (4) collectively represents all such stereoisomers. Such stereoisomers may be used alone or in admixture.

Illustrative examples of the fluorinated cyclic structure-bearing silicon compounds having formulae (1), (2), (3) and (4) are given below, but are not limited thereto. It is noted that the partial structure having the general formula:

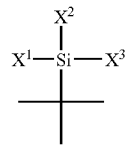

represents either one or both of partial structures in which a free valence bond extending from the silicon atom is attached to the carbon atom on the right or left side of the bond segment across which the free valence bond straddles, that is, two partial structures having the following general formulae.

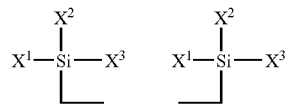

The same applies throughout the specification.

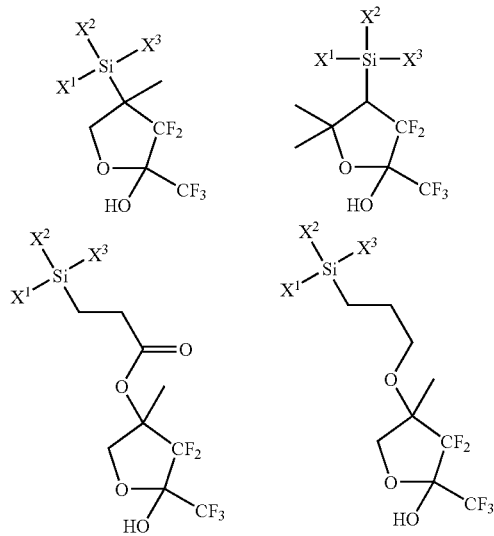

-continued
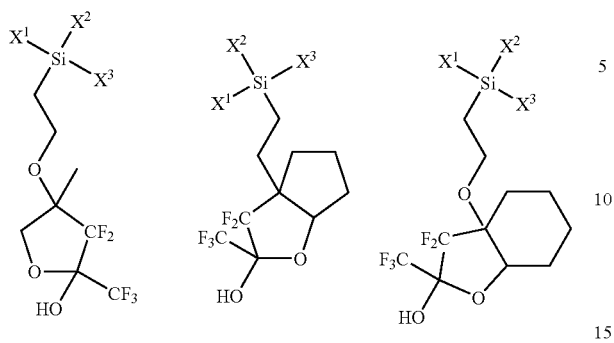
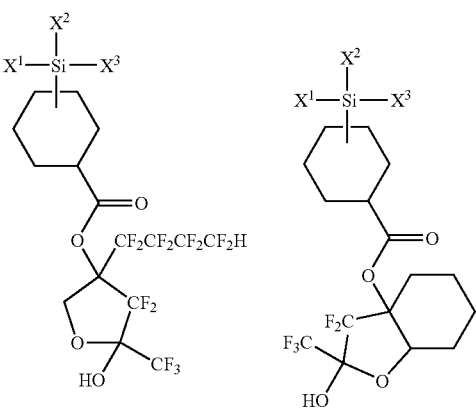
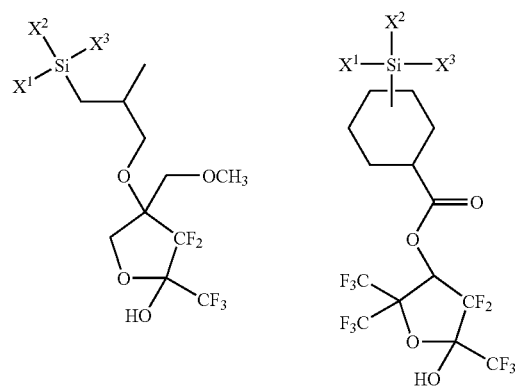
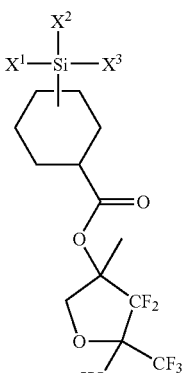
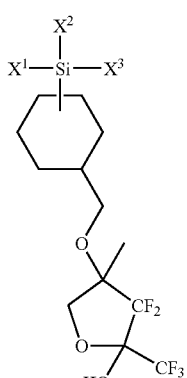
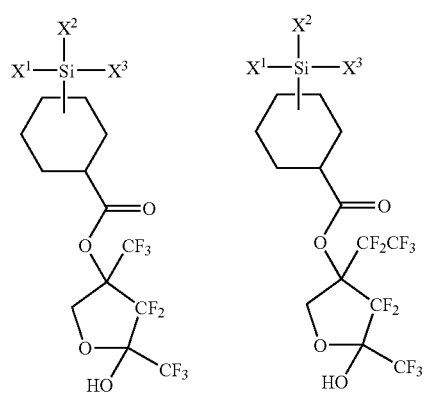
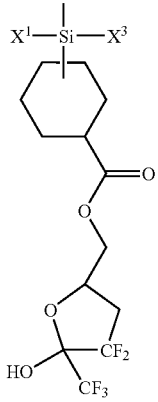
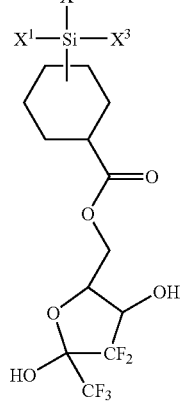
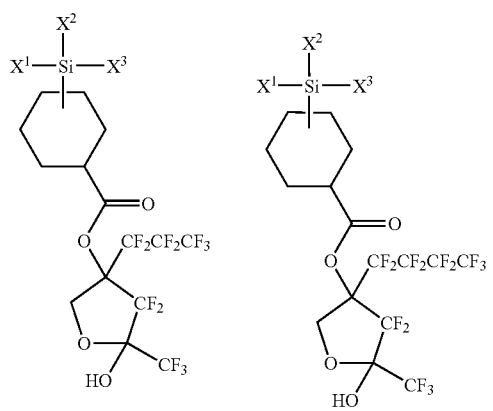
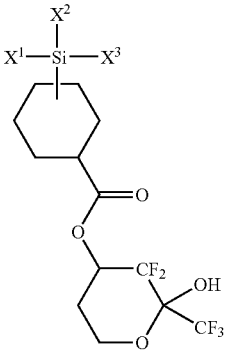
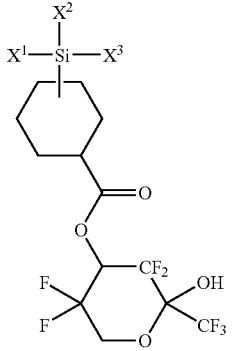

-continued
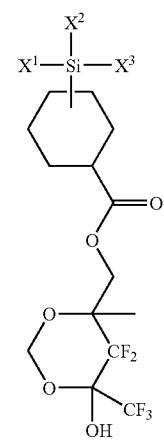 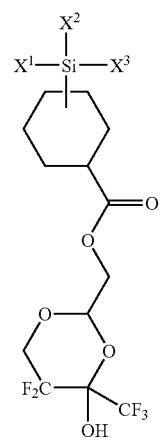
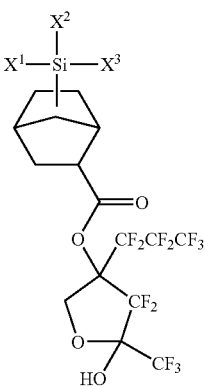 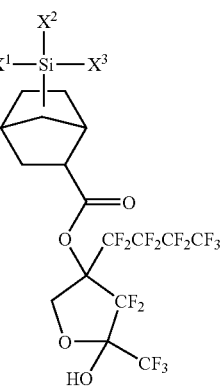
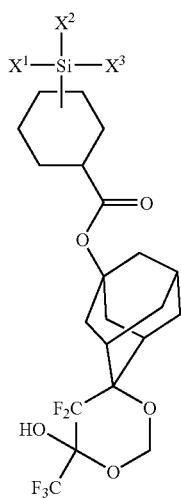 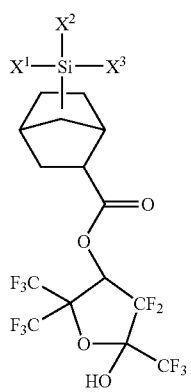
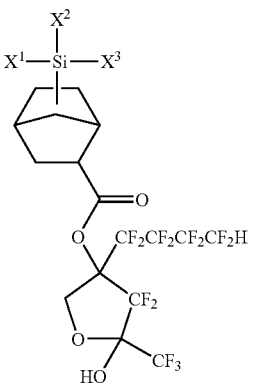 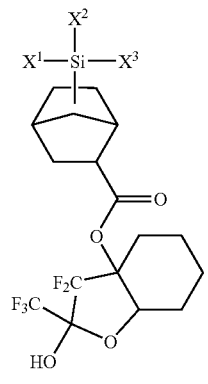
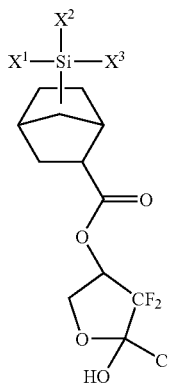 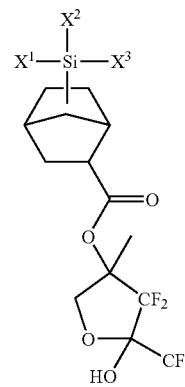
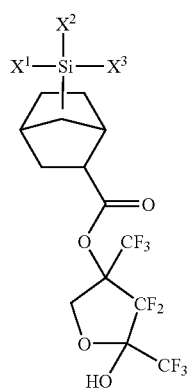 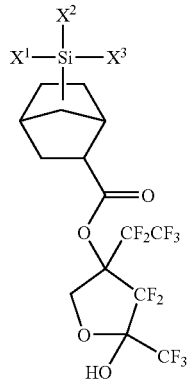
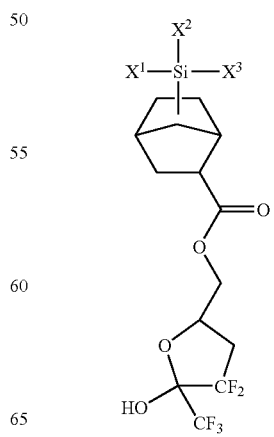 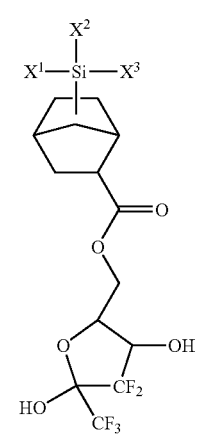

-continued
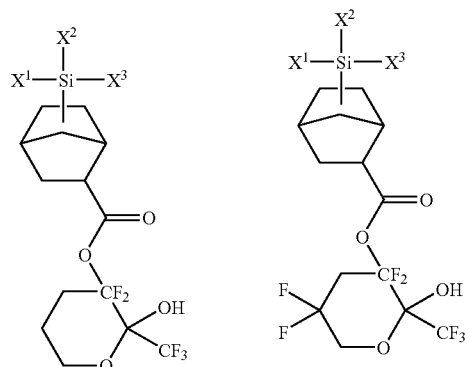
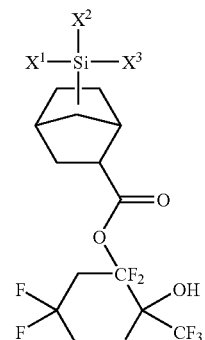
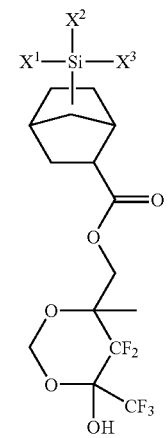
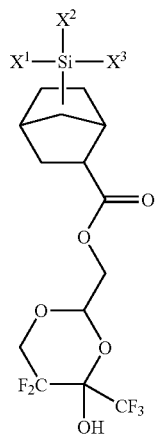
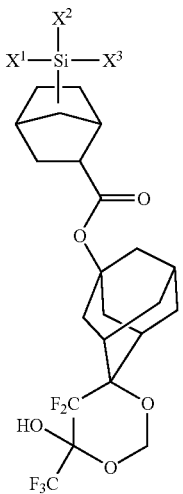
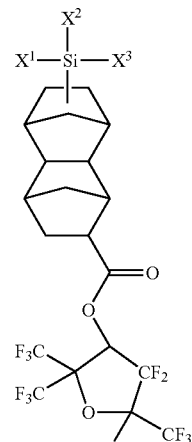
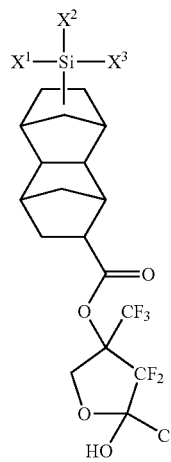
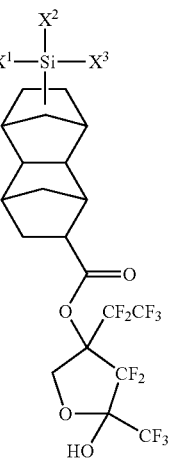
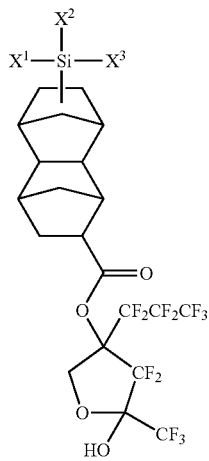
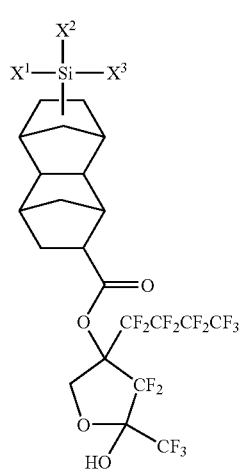
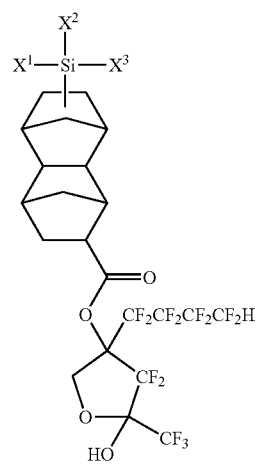
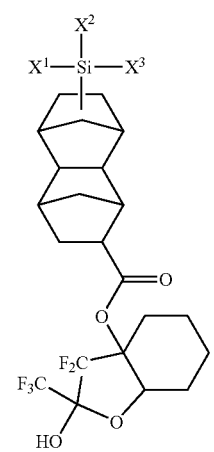

-continued
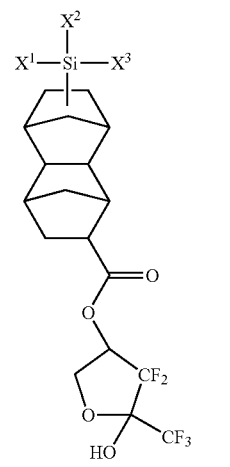
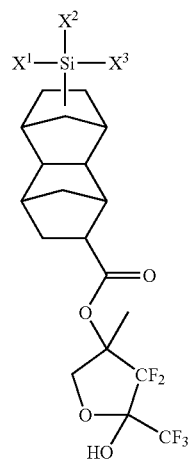
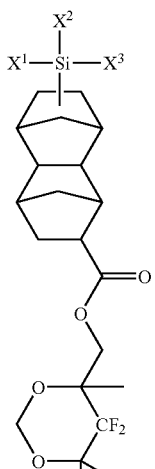
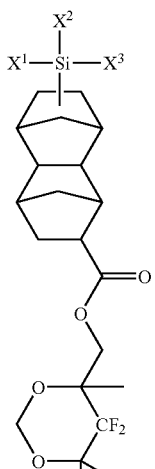
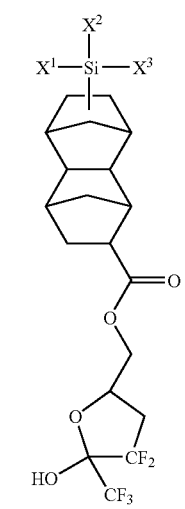
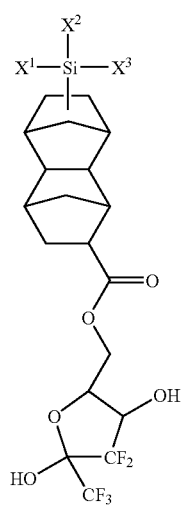

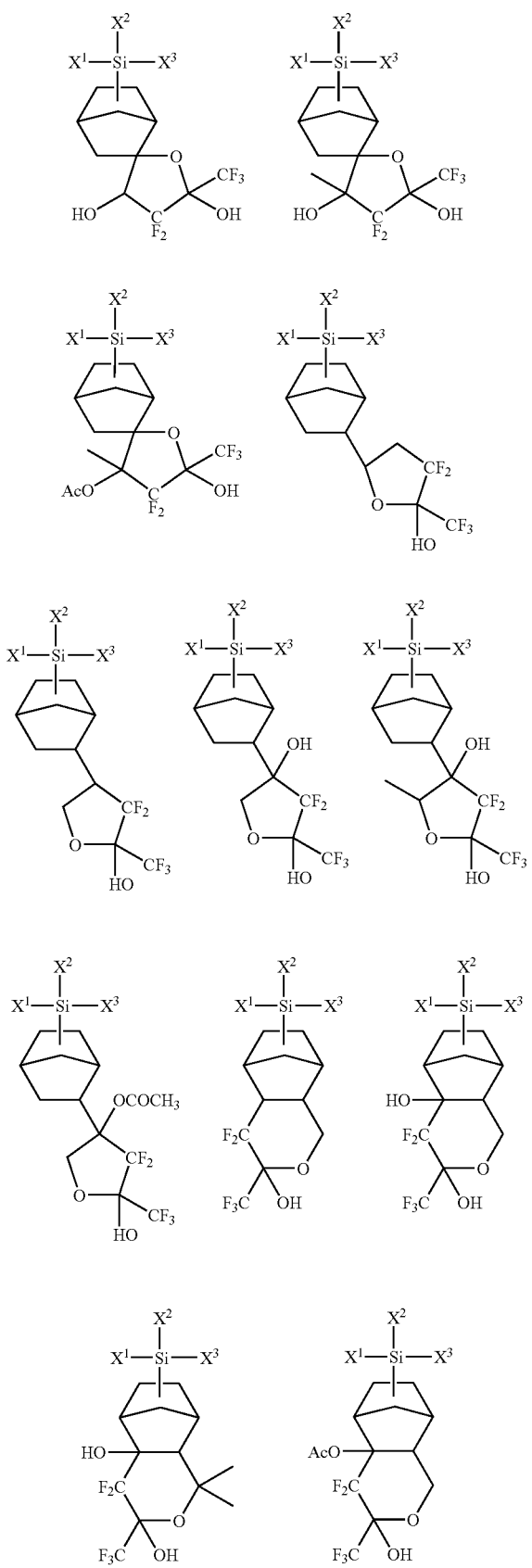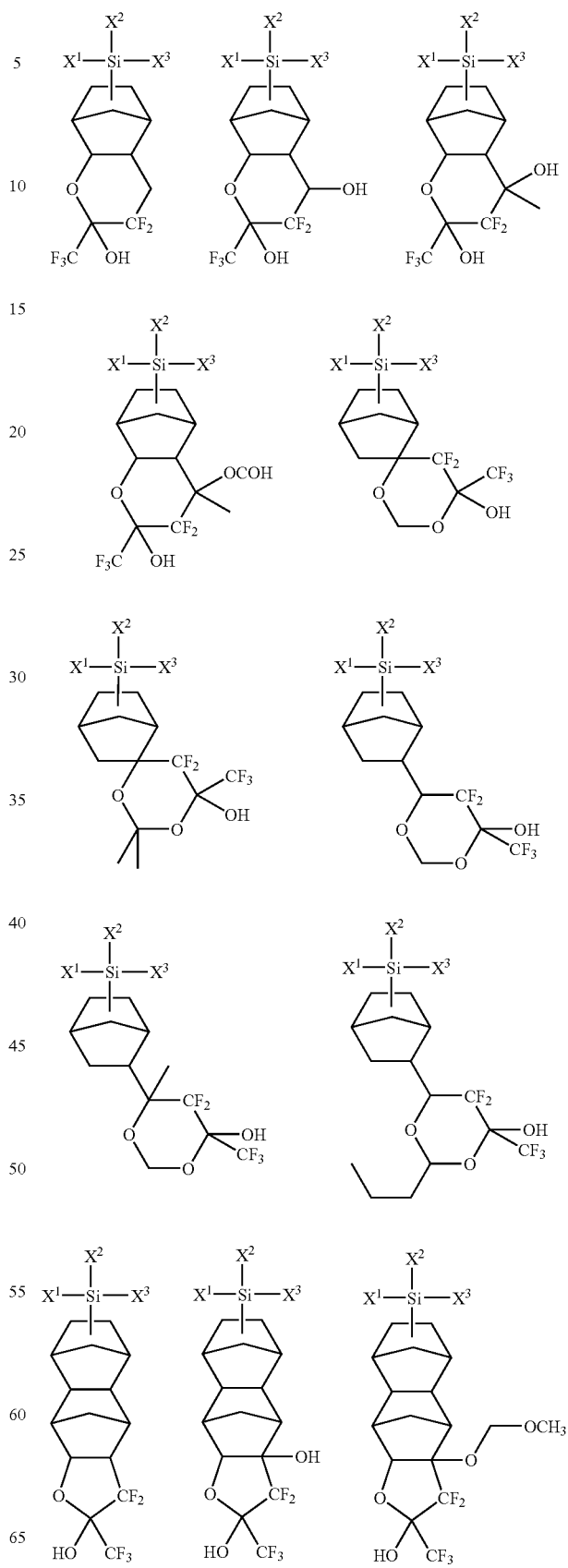

-continued

-continued

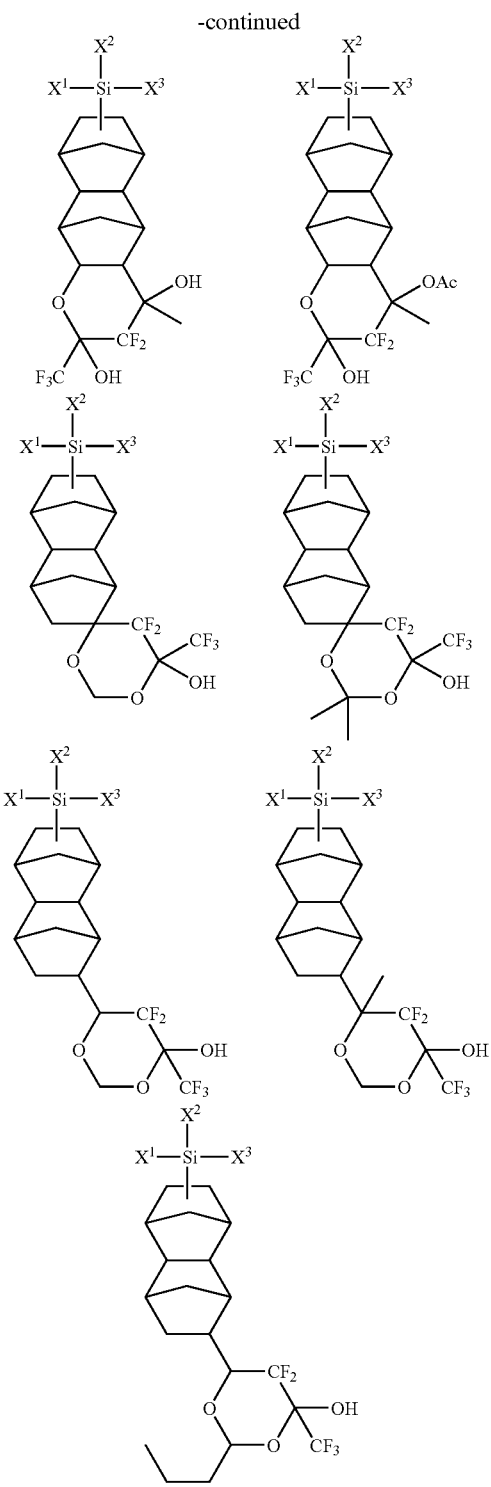

The fluorinated cyclic structure-bearing silicon compounds of the invention can be synthesized through various well-known carbon-to-silicon bond-forming reactions, preferably through hydrosilylation reaction of a fluoro-hemiacetal derivative having an unsaturated bond with a SiH-containing silane compound. The fluoro-hemiacetal derivatives having an unsaturated bond, preferably a double bond can be prepared by the method described in Japanese Patent Appln. No. 2004-313762 (U.S. Ser. No. 11/258,894, EP Appln. No. 05256687.4) by the same applicant/assignee as the present invention.

The hydrosilylation reaction is generally performed by heating reactants in the presence of a transition metal catalyst such as platinum, palladium or iridium. The reaction is usually performed without solvent. When the reactants are solid, however, one or more solvents selected from among hydrocarbons such as n-hexane, n-heptane, n-octane, benzene, toluene and xylene, ketones such as acetone and methyl ethyl ketone, and ethers such as diethyl ether, di-n-butyl ether, tetrahydrofuran and 1,4-dioxane may be used as an auxiliary medium.

The method described in Japanese Patent Appln. No. 2004-313762 is to produce cyclic structure-bearing fluorinated monomers having the general formulae (i), (ii), (iii) and (iv).

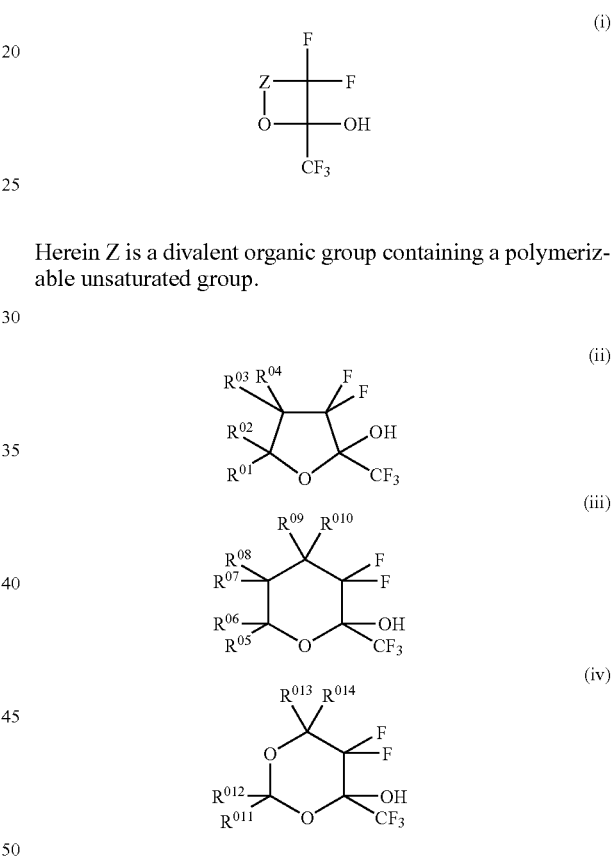

Herein Z is a divalent organic group containing a polymerizable unsaturated group.

Herein $R^{O1}$, $R^{O2}$, $R^{O3}$, and $R^{O4}$ are each independently selected from among hydrogen, hydroxyl, halogen, and straight, branched or cyclic monovalent organic groups of 1 to 15 carbon atoms, and at least one of $R^{O1}$, $R^{O2}$, $R^{O3}$ and $R^{O4}$ is a monovalent organic group containing a polymerizable unsaturated group. A combination of any of $R^{O1}$, $R^{O2}$, $R^{O3}$ and $R^{O4}$ may bond together to form a ring with the carbon atom or atoms to which they are attached. $R^{O5}$, $R^{O6}$, $R^{O7}$, $R^{O8}$, $R^{O9}$, and $R^{O10}$ are each independently selected from among hydrogen, hydroxyl, halogen, and straight, branched or cyclic monovalent organic groups of 1 to 15 carbon atoms, and at least one of $R^{O5}$, $R^{O6}$, $R^{O7}$, $R^{O8}$, $R^{O9}$, and $R^{O10}$ is a monovalent organic group containing a polymerizable unsaturated group. A combination of any of $R^{O5}$, $R^{O6}$, $R^{O7}$, $R^{O8}$, $R^{O9}$, and $R^{O10}$ may bond together to form a ring with the carbon atom or atoms to which they are attached. $R^{O11}$, $R^{O12}$, $R^{O13}$, and $R^{O14}$ are each independently selected from among hydrogen, hydroxyl, halogen, and straight, branched or cyclic monovalent organic groups of 1 to 15 carbon atoms, and at least one of $R^{o11}$, $R^{o12}$, $R^{o13}$ and $R^{o14}$ is a monovalent organic group containing a polymerizable unsaturated group. A combination of any of $R^{o11}$, $R^{o12}$, $R^{o13}$ and $R^{o14}$ may bond together to form a ring with the carbon atom or atoms to which they are attached.

For the preparation of the cyclic structure-bearing fluorinated monomers having formulae (i), (ii), (iii) and (iv), the key reaction is a reaction to form a hemiacetal ring. More specifically, the key is the step where a chain keto-alcohol compound having the general formula (v), (vi), (vii) or (viii) undergoes cyclization into a hemiacetal compound having the general formula (ix), (x), (xi) or (xii).

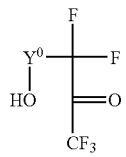

(v)

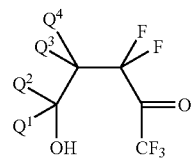

(vi)

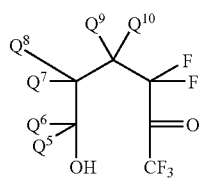

(vii)

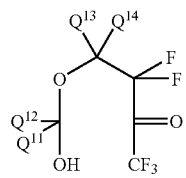

(viii)

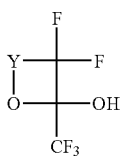

(ix)

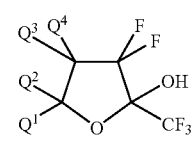

(x)

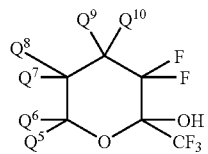

(xi)

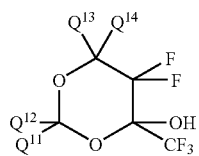

(xii)

Herein $Y^o$ is a divalent organic group containing a polymerizable unsaturated group or a divalent organic group having a functional group which can be converted to a polymerizable unsaturated group. $Q^1$, $Q^2$, $Q^3$, and $Q^4$ are each independently selected from among hydrogen, hydroxyl, halogen, and straight, branched or cyclic monovalent organic groups of 1 to 15 carbon atoms, and at least one of $Q^1$, $Q^2$, $Q^3$, and $Q^4$ is a monovalent organic group containing a polymerizable unsaturated group or a monovalent organic group having a functional group which can be converted to a polymerizable unsaturated group. A combination of any of $Q^1$ to $Q^4$ may bond together to form a ring with the carbon atom or atoms to which they are attached. $Q^5$, $Q^6$, $Q^7$, $Q^8$, $Q^9$ and $Q^{10}$ are each independently selected from among hydrogen, hydroxyl, halogen, and straight, branched or cyclic monovalent organic groups of 1 to 15 carbon atoms, and at least one of $Q^5$, $Q^6$, $Q^7$, $Q^8$, $Q^9$ and $Q^{10}$ is a monovalent organic group containing a polymerizable unsaturated group or a monovalent organic group having a functional group which can be converted to a polymerizable unsaturated group. A combination of any of $Q^5$ to $Q^{10}$ may bond together to form a ring with the carbon atom or atoms to which they are attached. $Q^{11}$, $Q^{12}$, $Q^{13}$, and $Q^{14}$ are each independently selected from among hydrogen, hydroxyl, halogen, and straight, branched or cyclic monovalent organic groups of 1 to 15 carbon atoms, and at least one of $Q^{11}$, $Q^{12}$, $Q^{13}$, and $Q^{14}$ is a monovalent organic group containing a polymerizable unsaturated group or a monovalent organic group having a functional group which can be converted to a polymerizable unsaturated group. A combination of any of $Q^{11}$, to $Q^{14}$ may bond together to form a ring with the carbon atom or atoms to which they are attached.

Hemiacetal cyclization reaction is generally carried out in a solvent and preferably under basic or acidic conditions, although the exact reaction conditions vary widely with the structure of reactants. Basic conditions are preferably such that a keto-alcohol compound creates an alkoxide. Suitable bases which can be used herein include organic bases such as triethylamine, diisopropylethylamine, N,N-dimethylaniline, pyridine, and 4-dimethylaminopyridine; inorganic bases such as sodium hydroxide, potassium hydroxide, barium hydroxide, sodium carbonate, sodium hydrogen carbonate, potassium carbonate, lithium hydride, sodium hydride, potassium hydride, and calcium hydride; alkyl metals such as methyllithium, n-butyllithium, methylmagnesium chloride, and ethylmagnesium bromide; and alkoxides such as sodium methoxide, sodium ethoxide, and potassium t-butoxide. In this case, although cyclization may be driven by treating a keto-alcohol compound as isolated with such a base, it is preferred that the alkoxide formed in the course of synthesis of a keto-alcohol compound itself be used as such and subjected to cyclization. Suitable acids which can be used herein include mineral acids such as hydrochloric acid, hydrobromic acid, sulfuric acid, and nitric acid; organic acids such as oxalic acid, trifluoroacetic acid, methanesulfonic acid, benzenesulfonic acid, and p-toluenesulfonic acid; and Lewis acids such as aluminum trichloride, aluminum ethoxide, aluminum isopropoxide, boron trifluoride, boron trichloride, boron tribromide, tin tetrachloride, tin tetrabromide, dibutyltin dichloride, dibutyltin dimethoxide, dibutyltin oxide, titanium tetrachloride, titanium tetrabromide, titanium(IV) methoxide, titanium(IV) ethoxide, titanium(IV) isopropoxide, and titanium(IV) oxide. In this case, although cyclization may be driven by treating a keto-alcohol compound as isolated with such an acid, it is preferred that cyclization be incurred by acid treatment as the post-treatment in the course of synthesis of a keto-alcohol compound itself. Suitable solvents which can be used herein include ethers such as diethyl ether, dibutyl ether, diethylene glycol diethyl ether, diethylene glycol dimethyl ether, tetrahydrofuran and 1,4-dioxane; hydrocarbons such as hexane, heptane, benzene, toluene, xylene and cumene; nitriles such as acetonitrile; and aprotic polar solvents such as N,N-dimethylformamide and hexamethylphosphoric triamide, alone or in admixture. The reaction temperature is preferably from −50° C. to approximately the boiling point of the solvent, and more preferably from −20° C. to 100° C. It is desirable from the yield standpoint to continue the reaction to completion while monitoring the reaction by gas chromatography (GC) or thin-layer chromatography (TLC). The reaction time is usually about 0.1 to about 250 hours.

The method of preparing cyclization precursor keto-alcohol compounds having the general formula (v), (vi), (vii) or (viii) differs with the structure. Introduction of an α,α,α,α',α'-pentafluorocarbonyl group moiety may be carried out, for example, by reacting a carbonyl compound with 1,1,3,3,3-pentafluoro-2-propenyl oxide (see T. Nakai et al., Tetrahedron Letters, Vol. 29, p. 4119, 1988 and T. Nakai et al., Organic Syntheses, Vol. 76, p. 151, 1998) or by gem-fluorination reaction of an α,α,α-trifluoroketone at α',α'-positions with an electrophilic fluorinating reagent (see T. Hiyama, Organofluorine Compounds Chemistry and Applications, p. 39, 2000). In particular, the reaction of a carbonyl compound with 1,1,3,3,3-pentafluoro-2-propenyl oxide is preferred because the necessary penta-fluoro-substituted partial structure can be introduced at a stretch.

Silicone Resin

The fluorinated cyclic structure-bearing silicone resins of the invention comprise a partial structure having the following general formula (1a), (2a), (3a) or (4a).

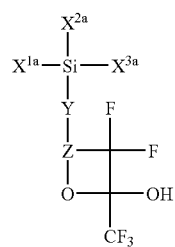
(1a)

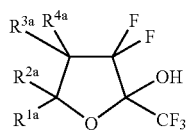
(2a)

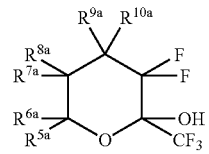
(3a)

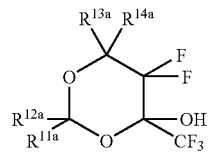
(4a)

Herein Y is a single bond or a divalent organic group, Z is a trivalent organic group, at least one of $X^{1a}$, $X^{2a}$ and $X^{3a}$ is an oxygen atom, and the remaining is a hydrogen atom, a hydroxyl group, a halogen atom, a straight, branched or cyclic alkoxy group of 1 to 6 carbon atoms, or a monovalent organic group of 1 to 20 carbon atoms having a straight, branched, cyclic or polycyclic skeleton (excluding alkoxy).

At least one of $R^{1a}$, $R^{2a}$, $R^{3a}$ and $R^{4a}$, preferably one, is a silicon-containing substituent group of the general formula:

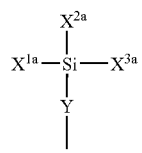

wherein at least one of $X^{1a}$, $X^{2a}$ and $X^{3a}$ is an oxygen atom and the remaining is a hydrogen atom, a hydroxyl group, a halogen atom, a straight, branched or cyclic alkoxy group of 1 to 6 carbon atoms, or a monovalent organic group of 1 to 20 carbon atoms having a straight, branched, cyclic or polycyclic skeleton (excluding alkoxy), and Y is a single bond or a divalent organic group, and the remaining $R^{1a}$ to $R^{4a}$ are each independently a hydrogen atom, a hydroxyl group, a halogen atom, or a monovalent organic group of 1 to 20 carbon atoms having a straight, branched, cyclic or polycyclic skeleton, or a combination of any two or more of $R^{1a}$, $R^{2a}$, $R^{3a}$ and $R^{4a}$ may bond together to form a ring with the carbon atom or atoms to which they are attached.

At least one of $R^{5a}$, $R^{6a}$, $R^{7a}$, $R^{8a}$, $R^{9a}$ and $R^{10a}$, preferably one, is a silicon-containing substituent group of the general formula:

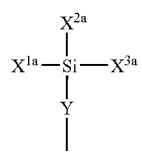

wherein at least one of $X^{1a}$, $X^{2a}$ and $X^{3a}$ is an oxygen atom and the remaining is a hydrogen atom, a hydroxyl group, a halogen atom, a straight, branched or cyclic alkoxy group of 1 to 6 carbon atoms, or a monovalent organic group of 1 to 20 carbon atoms having a straight, branched, cyclic or polycyclic skeleton (excluding alkoxy), and Y is a single bond or a divalent organic group, and the remaining $R^{5a}$ to $R^{10a}$ are each independently a hydrogen atom, a hydroxyl group, a halogen atom, or a monovalent organic group of 1 to 20 carbon atoms having a straight, branched, cyclic or polycyclic skeleton, or a combination of any two or more of $R^{5a}$, $R^{6a}$, $R^{7a}$, $R^{8a}$, $R^{9a}$ and $R^{10a}$ may bond together to form a ring with the carbon atom or atoms to which they are attached.

At least one of $R^{11a}$, $R^{12a}$, $R^{13a}$ and $R^{14a}$ preferably one, is a silicon-containing substituent group of the general formula:

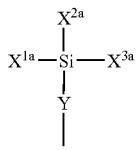

wherein at least one of $X^{1a}$, $X^{2a}$ and $X^{3a}$ is an oxygen atom and the remaining is a hydrogen atom, a hydroxyl group, a halogen atom, a straight, branched or cyclic alkoxy group of 1 to 6 carbon atoms, or a monovalent organic group of 1 to 20 carbon atoms having a straight, branched, cyclic or polycyclic skeleton (excluding alkoxy), and Y is a single bond or a divalent organic group, and the remaining $R^{11a}$ to $R^{14a}$ are each independently a hydrogen atom, a hydroxyl group, a halogen atom, or a monovalent organic group of 1 to 20 carbon atoms having a straight, branched, cyclic or polycyclic skeleton, or a combination of any two or more of $R^{11a}$, $R^{12a}$, $R^{13a}$ and $R^{14a}$ may bond together to form a ring with the carbon atom or atoms to which they are attached.

In the fluorinated cyclic structure-bearing silicone resins of the above general formulae, at least one of $X^{1a}$, $X^{2a}$ and $X^{3a}$ is an oxygen atom, through which the silicon atom bonds to another silicon atom to form a siloxane linkage (Si—O—Si) and hence, a polysiloxane chain.

While at least one of $R^{1a}$, $R^{2a}$, $R^{3a}$ and $R^{4a}$ is a silicon-containing substituent group as shown above, examples of the remaining substituent groups are as exemplified above for $R^1$, $R^2$, $R^3$ and $R^4$ in the fluorinated cyclic structure-bearing silicon compounds of the invention. Similarly, while at least one of $R^{5a}$, $R^{6a}$, $R^{7a}$, $R^{8a}$, $R^{9a}$ and $R^{10a}$ is a silicon-containing substituent group as shown above, examples of the remaining substituent groups are as exemplified for $R^5$, $R^6$, $R^7$, $R^8$, $R^9$ and $R^{10}$ in the fluorinated cyclic structure-bearing silicon compounds of the invention. While at least one of $R^{11a}$, $R^{12a}$, $R^{13a}$ and $R^{14a}$ is a silicon-containing substituent group as shown above, examples of the remaining substituent groups are as exemplified for $R^{11}$, $R^{12}$, $R^{13}$ and $R^{14}$ in the fluorinated cyclic structure-bearing silicon compounds of the invention. Also, examples of Y and Z are as exemplified above for Y and Z in the fluorinated cyclic structure-bearing silicon compounds of the invention.

In the fluorinated cyclic structure-bearing silicone resins of formulae (1a), (2a), (3a) and (4a) according to the invention, depending on the type and combination of the groups represented by $X^{1a}$, $X^{2a}$, $X^{3a}$, Y, Z, $R^{1a}$, $R^{2a}$, $R^{3a}$, $R^{4a}$, $R^{5a}$, $R^{6a}$, $R^{7a}$, $R^{8a}$, $R^{9a}$, $R^{10a}$, $R^{11a}$, $R^{12a}$, $R^{13a}$ and $R^{14a}$, carbon atoms constituting the molecule can be asymmetric, and there can exist enantiomers and diastereomers. Each of formulae (1a) to (4a) collectively represents all such stereoisomers. Such stereoisomers may be used alone or in admixture.

In formula (1a) or in the event where formula (2a), (3a) or (4a) has only one substituent group $X^{1a}X^{2a}X^{3a}Si$—Y— (for example, $R^{1a}$, $R^{5a}$ or $R^{11a}$ is $X^{1a}X^{2a}X^{3a}Si$—Y—, and the remaining are the aforementioned atoms or groups other than $X^{1a}X^{2a}X^{3a}Si$—Y—), the structure is a $R_3SiO_{1/2}$ unit, known as M unit, when only one of $X^{1a}$, $X^{2a}$ and $X^{3a}$ is an oxygen atom; a $R_2SiO_{2/2}$ unit, known as D unit, when two of $X^{1a}$, $X^{2a}$ and $X^{3a}$ are oxygen atoms; and a $RSiO_{3/2}$ unit, known as T unit, when all of $X^{1a}$, $X^{2a}$ and $X^{3a}$ are oxygen atoms. It is provided that one R has the formula:

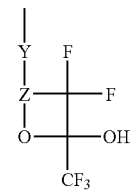

(alternatively, when $R^{1a}$, $R^{5a}$ or $R^{11a}$ is $X^{1a}X^{2a}X^{3a}Si$—Y—, for example, the above formulae are:

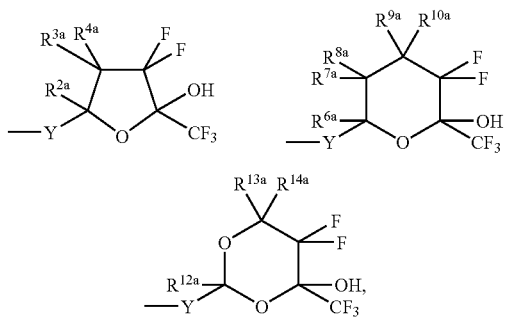

respectively), and the remaining R are hydrogen, hydroxyl, halogen, straight, branched or cyclic $C_1$-$C_6$ alkoxy groups or monovalent $C_1$-$C_{20}$ organic groups having a straight, branched, cyclic or polycyclic skeleton (excluding alkoxy).

Suitable methods may be employed in preparing the fluorinated cyclic structure-bearing silicone resins of the invention. A first method is by using a fluorinated cyclic structure-bearing silicon compound of formula (1), (2), (3) or (4) as a silane monomer and preferably, another silane monomer as a comonomer and effecting cohydrolytic condensation reaction of such a mixture.

The comonomers which can be used in the cohydrolytic condensation reaction together with the fluorinated cyclic structure-bearing silicon compound of the invention include silicon compounds having the general formulae (5), (6) and (7).

-continued

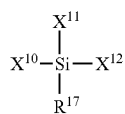
(7)

Herein $R^{15}$ is a $C_3$-$C_{20}$ organic group with a straight, branched, cyclic or polycyclic structure which has a carboxyl group as a functional group, the carboxyl group being protected with an acid-decomposable protecting group or not protected, and which may contain a halogen, oxygen or sulfur atom or atoms in to the carboxyl group $R^{16}$ is a $C_4$-$C_{16}$ organic group which has a lactone ring or carboxylic anhydride as a functional group, and which may contain a halogen, oxygen or sulfur atom or atoms in addition to the lactone ring or carboxylic anhydride. $R^{17}$ is a $C_3$-$C_{20}$ organic group with a straight, branched, cyclic or polycyclic structure which has a hydroxyl group as a functional group and which may contain a halogen, oxygen or sulfur atom or atoms. $X^4$, $X^5$, $X^6$, $X^7$, $X^8$, $X^9$, $X^{10}$, $X^{11}$ and $X^{12}$ each are hydrogen, hydroxyl, halogen, a straight, branched or cyclic $C_1$-$C_6$ alkoxy group, or a monovalent $C_1$-$C_{20}$ organic group having a straight, branched, cyclic or polycyclic skeleton (excluding alkoxy).

Through cohydrolytic condensation reaction, these comonomers are incorporated as units having a partial structure of the general formulae (5a), (6a) and (7a) to form the fluorinated cyclic structure-bearing silicone resins of the invention.

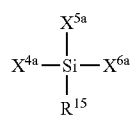
(5a)

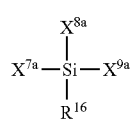
(6a)

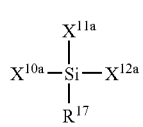
(7a)

Herein $R^{15}$, $R^{16}$ and $R^{17}$ are as defined above. At least one of $X^{4a}$, $X^{5a}$ and $X^{6a}$ is an oxygen atom, and the remaining are hydrogen, hydroxyl, halogen, a straight, branched or cyclic $C_1$-$C_6$ alkoxy group, or a monovalent $C_1$-$C_{20}$ organic group having a straight, branched, cyclic or polycyclic skeleton (excluding alkoxy). At least one of $X^{7a}$, $X^{8a}$ and $X^{9a}$ is an oxygen atom, and the remaining are hydrogen, hydroxyl, halogen, a straight, branched or cyclic $C_1$-$C_6$ alkoxy group, or a monovalent $C_1$-$C_{20}$ organic group having a straight, branched, cyclic or polycyclic skeleton (excluding alkoxy). At least one of $X^{10a}$, $X^{11a}$ and $X^{12a}$ is an oxygen atom, and the remaining are hydrogen, hydroxyl, halogen, a straight, branched or cyclic $C_1$-$C_6$ alkoxy group, or a monovalent $C_1$-$C_{20}$ organic group having a straight, branched, cyclic or polycyclic skeleton (excluding alkoxy).

Also for each set of three $X^{4a}$ to $X^{6a}$, $X^{7a}$ to $X^{9a}$, and $X^{10a}$ to $X^{12a}$, the structure is a $R'_3SiO_{1/2}$ unit, known as M unit, when only one of three is an oxygen atom; a $R'_2SiO_{2/2}$ unit, known as D unit, when two are oxygen atoms; and a $R'SiO_{3/2}$ unit, known as T unit, when all three are oxygen atoms. It is provided that one $R'$ is $R^{15}$, $R^{16}$ or $R^{17}$, and the remaining $R'$ are hydrogen, hydroxyl, halogen, straight, branched or cyclic $C_1$-$C_6$ alkoxy groups or monovalent $C_1$-$C_{20}$ organic groups having a straight, branched, cyclic or polycyclic skeleton (excluding alkoxy).

Examples of $X^4$, $X^5$ and $X^6$; $X^7$, $X^8$ and $X^9$; and $X^{10}$, $X^{11}$ and $X^{12}$ are as exemplified above for $X^1$, $X^2$ and $X^3$ in the fluorinated cyclic structure-bearing silicon compounds of the invention. Also, examples of $X^{4a}$, $X^{5a}$ and $X^{6a}$; $X^{7a}$, $X^{8a}$ and $X^{9a}$; and $X^{10a}$, $X^{11a}$ and $X^{12a}$ are as exemplified above for $X^{1a}$, $X^{2a}$ and $X^{3a}$ in the fluorinated cyclic structure-bearing silicone resins of the invention.

In the silicon compounds of formula (5), $R^{15}$ is a substituent group having an acid labile group-protected carboxylic acid (carboxyl group protected with an acid-decomposable protecting group), which is believed to have a function of establishing differential dissolution between exposed and unexposed areas, i.e., contrast. The acid labile group is a technical term generally used in the resist-related art. The acid labile group with which a functional group is protected functions such that when a strong acid is generated from a photoacid generator upon exposure, the bond between the acid labile group and the functional group is scissored under the catalysis of the strong acid. As a result of scission, carboxylic acid is regenerated herein. $R^{15}$ is a $C_3$-$C_{20}$ organic group with a straight, branched, cyclic or polycyclic structure which may contain a halogen, oxygen or sulfur atom or atoms. Although groups of many different structures may be used as $R^{15}$, cyclic hydrocarbon groups having silicon and a protected carboxyl group directly attached thereto are preferred. Suitable cyclic hydrocarbon groups include cyclopentane, cyclohexane, bicyclo[2.2.1]heptane (or norbornane), bicyclo[2.2.2]octane, and tetracyclo[4.4.0.1$^{2,5}$.1$^{7,10}$]dodecane (or tetracyclododecane). Inter alia, those groups containing bicyclo[2.2.1]heptane or tetracyclo[4.4.0.1$^{2,5}$.1$^{7,10}$] dodecane are especially preferred.

Preferred, non-limiting examples of the silicon compounds of formula (5) are given below.

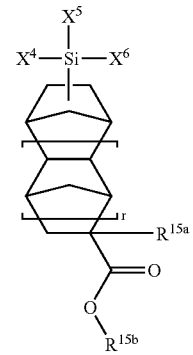

Herein $R^{15a}$ is hydrogen, methyl or trifluoromethyl, $R^{15b}$ is hydrogen or an acid labile group, r is 0 or 1, $X^4$, $X^5$ and $X^6$ are as defined above.

The acid labile group represented by $R^{15b}$ may be selected from a variety of such groups. Examples of the acid labile group are groups of the following general formulae (L1) to (L4), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms.

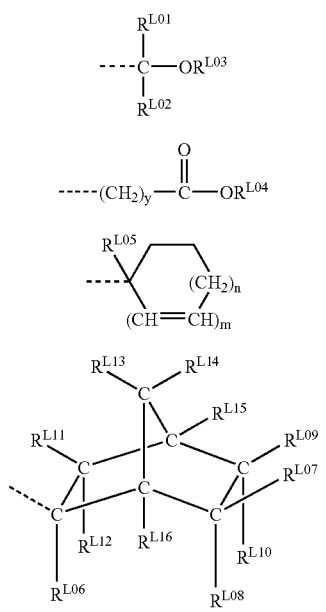

In these formulae and throughout the specification, the broken line denotes a valence bond. $R^{L01}$ and $R^{L02}$ are hydrogen or straight, branched or cyclic alkyl groups of 1 to 18 carbon atoms, preferably 1 to 10 carbon atoms. Exemplary alkyl groups include methyl, ethyl, n-propyl, isopropyl, n-butyl, sec-butyl, tert-butyl, cyclopentyl, cyclohexyl, 2-ethylhexyl, and n-octyl. $R^{L03}$ is a monovalent hydrocarbon group of 1 to 18 carbon atoms, preferably 1 to 10 carbon atoms, which may contain a hetero atom such as oxygen, examples of which include unsubstituted straight, branched or cyclic alkyl groups and substituted forms of such alkyl groups in which some hydrogen atoms are replaced by hydroxyl, alkoxy, oxo, amino, alkylamino or the like. Illustrative examples are the substituted alkyl groups shown below.

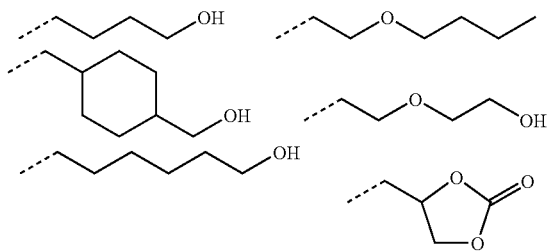

A pair of $R^{L01}$ and $R^{L02}$, $R^{L01}$ and $R^{L03}$, or $R^{L02}$ and $R^{L03}$ may form a ring with carbon and oxygen atoms to which they are attached. Each of $R^{L01}$, $R^{L02}$ and $R^{L03}$ is a straight or branched alkylene group of 1 to 18 carbon atoms, preferably 1 to 10 carbon atoms when they form a ring.

$R^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (L1). Exemplary tertiary alkyl groups are tert-butyl, tert-amyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, and 2-ethyl-2-adamantyl. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-2-oxooxolan-5-yl. Letter y is an integer of 0 to 6.

In formula (L3), $R^{L05}$ is a monovalent hydrocarbon group of 1 to 8 carbon atoms or a substituted or unsubstituted aryl group of 6 to 20 carbon atoms. Examples of the monovalent hydrocarbon group include straight, branched or cyclic alkyl groups such as methyl, ethyl, n-propyl, isopropyl, n-butyl, sec-butyl, tert-butyl, tert-amyl, n-pentyl, n-hexyl, cyclopentyl, and cyclohexyl, and substituted forms of such groups in which some hydrogen atoms are substituted with hydroxyl, alkoxy, carboxy, alkoxycarbonyl, oxo, amino, alkylamino, cyano, mercapto, alkylthio, sulfo or other groups. Exemplary aryl groups are phenyl, methylphenyl, naphthyl, anthryl, phenanthryl, and pyrenyl. Letter m is equal to 0 or 1, n is equal to 0, 1, 2 or 3, and 2 m+n is equal to 2 or 3.

In formula (L4), $R^{L06}$ is a monovalent hydrocarbon group of 1 to 8 carbon atoms or a substituted or unsubstituted aryl group of 6 to 20 carbon atoms. Examples of these groups are the same as exemplified for $R^{L05}$. $R^{L07}$ to $R^{L16}$ independently represent hydrogen or monovalent hydrocarbon groups of 1 to 15 carbon atoms. Exemplary hydrocarbon groups are straight, branched or cyclic alkyl groups such as methyl, ethyl, n-propyl, isopropyl, n-butyl, sec-butyl, tert-butyl, tert-amyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted forms of these groups in which some hydrogen atoms are replaced by hydroxyl, alkoxy, carboxy, alkoxycarbonyl, oxo, amino, alkylamino, cyano, mercapto, alkylthio, sulfo or other groups. Alternatively, $R^{L07}$ to $R^{L16}$, taken together, form a ring (for example, a pair of $R^{L07}$ and $R^{L08}$, $R^{L07}$ and $R^{L09}$, $R^{L08}$ and $R^{L10}$, $R^{L09}$ and $R^{L10}$, $R^{L11}$ and $R^{L12}$, $R^{L13}$ and $R^{L14}$, or a similar pair form a ring). Each of $R^{L07}$ to $R^{L16}$ represents a divalent $C_1$-$C_{15}$ hydrocarbon group when they form a ring, examples of which are the ones exemplified above for the monovalent hydrocarbon groups, with one hydrogen atom being eliminated. Two of $R^{L07}$ to $R^{L16}$ which are attached to adjoining carbon atoms (for example, a pair of $R^{L07}$ and $R^{L09}$, $R^{L09}$ and $R^{L15}$, $R^{L13}$ and $R^{L15}$, or a similar pair) may bond together directly to form a double bond.

Of the acid labile groups of formula (L1), the straight and branched ones are exemplified by the following groups.

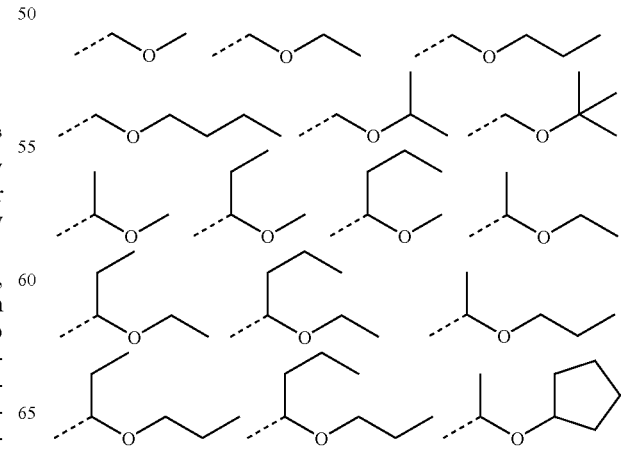

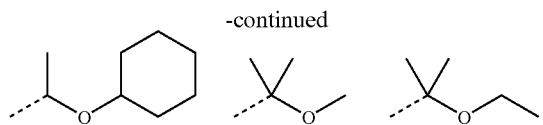

Of the acid labile groups of formula (L1), the cyclic ones are, for example, tetrahydrofuran-2-yl, 2-methyltetrahydrofuran-2-yl, tetrahydropyran-2-yl, and 2-methyltetrahydropyran-2-yl.

Examples of the acid labile groups of formula (L2) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl groups.

Examples of the acid labile groups of formula (L3) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-cyclohexylcyclopentyl, 1-(4-methoxy-n-butyl)cyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl groups.

Examples of the tertiary alkyl groups of 4 to 20 carbon atoms, trialkylsilyl groups in which each alkyl moiety has 1 to 6 carbon atoms, and oxoalkyl groups of 4 to 20 carbon atoms are as exemplified for $R^{L04}$.

In the silicon compounds of formula (6), $R^{16}$ is a $C_4$-$C_{16}$ organic group which has a lactone ring or carboxylic anhydride as a functional group, and which may contain a halogen, oxygen or sulfur atom or atoms in addition to the lactone ring or carboxylic anhydride. The lactone ring or carboxylic anhydride as a functional group is believed to have the functions of providing a polarity for substrate adhesion and establishing a high resolution. Although groups of many different structures may be used as $R^{16}$, groups having a cyclic hydrocarbon group are preferred. Suitable cyclic hydrocarbon groups include cyclopentane, cyclohexane, bicyclo[2.2.1]heptane (or norbornane), bicyclo[2.2.2]octane, and tetracyclo[4.4.0.1$^{2,5}$.1$^{7,10}$]dodecane (or tetracyclododecane). Inter alia, those groups containing bicyclo[2.2.1]heptane or tetracyclo[4.4.0.1$^{2,5}$.1$^{7,10}$]dodecane are especially preferred. The lactone ring or carboxylic anhydride is most preferably one having a five-membered ring structure.

Preferred, non-limiting examples of the silicon compounds of formula (6) are given below.

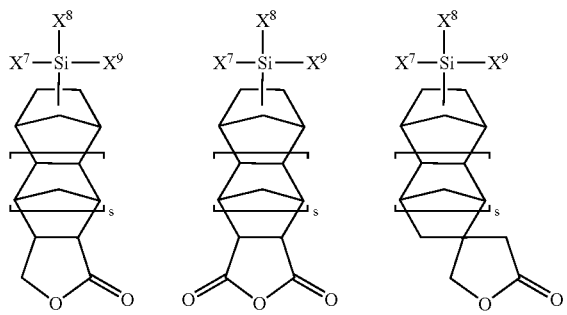

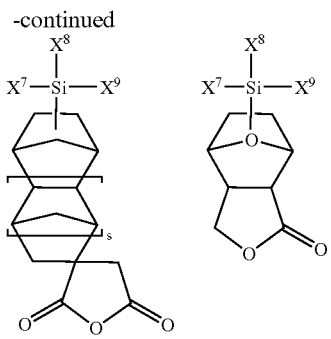

Herein s is 0 or 1, $X^7$, $X^8$ and $X^9$ are as defined above.

In the silicon compounds of formula (7), $R^{17}$ is a $C_3$-$C_{20}$ organic group with a straight, branched, cyclic or polycyclic structure which has a hydroxyl group as a functional group and which may contain a halogen, oxygen or sulfur atom or atoms. The hydroxyl group as a functional group is incorporated as a polar group for controlling substrate adhesion, dissolution or the like. Although groups of many different structures may be used as $R^{17}$, groups having a cyclic hydrocarbon group are preferred. Suitable cyclic hydrocarbon groups include cyclopentane, cyclohexane, bicyclo[2.2.1]heptane (or norbornane), bicyclo[2.2.2]octane, and tetracyclo[4.4.0.1$^{2,5}$.1$^{7,10}$]dodecane (or tetracyclododecane). Inter alia, those groups containing bicyclo[2.2.1]heptane or tetracyclo[4.4.0.1$^{2,5}$.1$^{7,10}$]dodecane are especially preferred.

Preferred, non-limiting examples of the silicon compounds of formula (7) are given below.

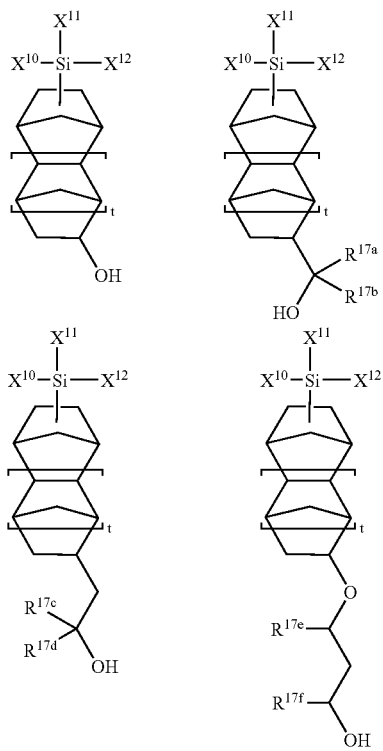

Herein $R^{17a}$ and $R^{17b}$ are each a $C_1$-$C_8$ alkyl or perfluoroalkyl group or may bond together to form a ring with the carbon atom to which they are attached; $R^{17c}$ and $R^{17d}$ are each a $C_1$-$C_8$ alkyl or perfluoroalkyl group or may bond together to form a ring with the carbon atom to which they are attached; $R^{17e}$ and $R^{17f}$ are each a $C_1$-$C_8$ alkyl or perfluoroalkyl group or may bond together to form a ring with the carbon atom to which they are attached; t is 0 or 1; $X^{10}$, $X^{11}$ and $X^{12}$ are as defined above.

The silicon compounds of formulae (5), (6) and (7) are used in cohydrolytic condensation together with the fluorinated cyclic structure-bearing silicon compounds of the invention while they function as mono-, di- or tri-functional silane monomers depending on the number of hydrolyzable substituent groups on silicon. The hydrolyzable substituent groups in the molecule of silane monomers may be of the same type or two or more different types of hydrolyzable substituent groups may be included. Preferred hydrolyzable substituent groups are alkoxy groups, with methoxy and ethoxy being more preferred. When the mono- or di-functional silane monomer is used, the remaining two or one substituent group on silicon other than the hydrolyzable substituent groups is a monovalent organic group of 1 to 20 carbon atoms having a straight, branched, cyclic or polycyclic skeleton. Monovalent organic groups of up to 6 carbon atoms are preferred for ease of purification by distillation or the like, with alkyl of up to 6 carbon atoms, perfluoroalkyl of 1 to 8 carbon atoms, and phenyl being especially preferred. For each class, these silane monomers may be used alone or in admixture.

In preparing the fluorinated cyclic structure-bearing silicone resins of the invention through cohydrolytic condensation, the monofunctional monomer is used for end-capping of a silicone resin (e.g., silanol ends of a siloxane polymer) as M units. For the preparation of silicone resins (polysiloxane polymers), either a difunctional monomer (as D units for mainly providing a chain or cyclic polysiloxane polymer) or a trifunctional monomer (as T units for mainly providing a ladder or cage shaped silsesquioxane polymer) or a mixture of both is used. In this regard, if the difunctional monomer is equal to or more than 50 mol % of the entire monomers subject to condensation, a silicone resin resulting from condensation may become unlikely to solidify and thus difficult to purify. Thus, the trifunctional monomer should preferably be used in an amount of more than 50 mol % of the entire monomers.

The mixing ratio of monomers in a reaction solution subject to cohydrolysis is described. The proportion of the silane monomer of formula (5) relative to the entire silane monomers, which generally governs the contrast between exposed and unexposed areas of resist film, is preferably 5 to 80 mol %, more preferably 10 to 50 mol %, although it varies with the molecular weight of protective group or the like. The proportion of the total of the fluorinated cyclic structure-bearing silane monomer of the invention, the silane monomer of formula (6), and the monomer of formula (7), that is, the total of silane monomers having polar groups relative to the entire silane monomers is preferably 20 to 95 mol %, more preferably 50 to 90 mol %. If this proportion is too low, pattern stripping and pattern collapse by swelling can occur during development. If this proportion is too high, the resist film is reduced in contrast and resolution. The proportion of an individual silane monomer having a polar group relative to the entire silane monomers having polar groups should preferably be 5 to 95 mol % in order that said individual silane monomer exert its own function.

Upon cohydrolysis, one or more hydrolyzable silane monomers having at least two hydrolyzable substituent groups may be added as long as the amount is limited to or below 30 mol % based on the entire monomers. Suitable additional monomers include silane monomers of the general formulae (8), (9) and (10).

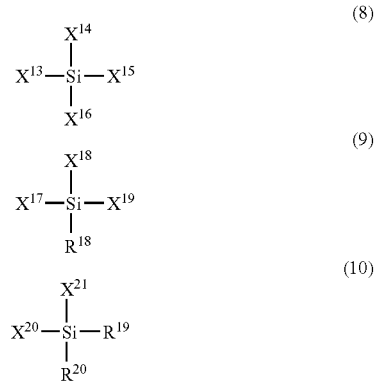

Herein $X^{13}$, $X^{14}$, $X^{15}$, $X^{16}$, $X^{17}$, $X^{18}$, $X^{19}$, $X^{20}$ and $X^{21}$ each are hydrogen, hydroxyl, halogen, or a straight, branched or cyclic $C_1$-$C_6$ alkoxy group. $R^{18}$, $R^{19}$ and $R^{20}$ each are a $C_1$-$C_{20}$ alkyl or perfluoroalkyl group having a straight, branched, cyclic or polycyclic skeleton.

These silane monomers are incorporated as units having a partial structure of the general formulae (8a), (9a) and (10a) to form the fluorinated cyclic structure-bearing silicone resins of the invention.

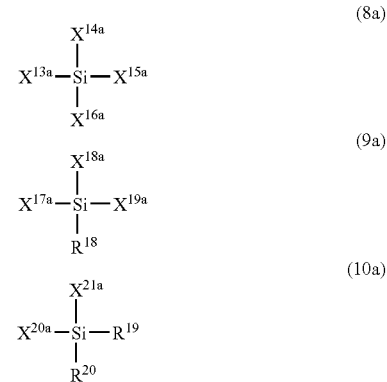

Herein $R^{18}$, $R^{19}$ and $R^{20}$ are as defined above. At least one of $X^{13a}$, $X^{14a}$, $X^{15a}$ and $X^{16a}$ is an oxygen atom, and the remaining are hydrogen, hydroxyl, halogen, or a straight, branched or cyclic $C_1$-$C_6$ alkoxy group. At least one of $X^{17a}$, $X^{18a}$ and $X^{19a}$ is an oxygen atom, and the remaining are hydrogen, hydroxyl, halogen, or a straight, branched or cyclic $C_1$-$C_6$ alkoxy group. At least one or $X^{20a}$ and $X^{21a}$ is an oxygen atom, and the remaining is hydrogen, hydroxyl, halogen, or a straight, branched or cyclic $C_1$-$C_6$ alkoxy group.

Also for each set of $X^{13a}$ to $X^{16a}$, $X^{17a}$ to $X^{19a}$, and $X^{20a}$ to $X^{21a}$, the structure is a $R''_3SiO_{1/2}$ unit, known as M unit, when only one of them is an oxygen atom; a $R''_2SiO_{2/2}$ unit, known as D unit, when two are oxygen atoms; a $R''SiO_{3/2}$ unit, known as T unit, when three are oxygen atoms; and a $SiO_{4/2}$ unit, known as Q unit, when four are oxygen atoms. It is provided that in the case of formula (8a), R" is hydrogen, hydroxyl, halogen, or a straight, branched or cyclic alkoxy group; in the case of formula (9a), one R" is $R^{18}$, and the remaining R" are hydrogen, hydroxyl, halogen, or straight, branched or cyclic $C_1$-$C_6$ alkoxy groups; in the case of formula (10a), two R" are $R^{19}$ and $R^{20}$, and the remaining R" are hydrogen, hydroxyl, halogen, or straight, branched or cyclic $C_1$-$C_6$ alkoxy groups.

Examples of $X^{13}$, $X^{14}$, $X^{15}$ and $X^{16}$; $X^{17}$, $X^{18}$ and $X^{19}$; and $X^{20}$ and $X^{21}$ are as exemplified above for $X^1$, $X^2$ and $X^3$ in the fluorinated cyclic structure-bearing silicon compounds of the invention. Also, examples of $X^{13a}$, $X^{14a}$, $X^{15a}$ and $X^{16a}$; $X^{17a}$, $X^{18a}$ and $X^{19a}$; and $X^{20a}$ and $X^{21a}$ are as exemplified above for $X^{1a}$, $X^{2a}$ and $X^{3a}$ in the fluorinated cyclic structure-bearing silicone resins of the invention.

Where all silane monomers have bulky side chains, for example, only a lower molecular weight product can be obtained by mere adjustment of condensation conditions. In such a situation, the molecular weight can be increased by adding a monomer in which the substituent group(s) bonded to a silicon atom, other than the hydrolyzable groups, is solely an alkyl group of up to 4 carbon atoms. As is known in the art, when it is desired to enhance the transparency of a resin to exposure light of a shorter wavelength, for example, light of 157 nm, the desired effect is achieved by increasing the number of fluorine atoms per unit weight of the resin. To further impart such transparency to the resin, the addition of a halosilane or alkoxysilane having a fluoroalkyl group incorporated therein is effective.

The cohydrolytic condensate can be produced according to the ordinary way of cohydrolytic condensation. Specifically, a mixture of silane monomers is contacted with a sufficient amount of water to induce cohydrolytic condensation to synthesize the desired product. The reaction may be effected in the presence of an acid catalyst or base catalyst and also in an organic solvent. Examples of suitable acid catalysts used in the reaction include mineral acids such as hydrochloric acid, nitric acid, sulfuric acid, perchloric acid, and phosphoric acid; and organic acids such as acetic acid, oxalic acid, methanesulfonic acid, p-toluenesulfonic acid, trifluoroacetic acid, trifluoromethanesulfonic acid, and citric acid. Examples of suitable base catalysts include ammonia, organic bases such as methylamine, dimethylamine, ethylamine, diethylamine, triethylamine, choline, diethylhydroxylamine, 1,8-diazabicyclo[5.4.0]undecan-7-ene (DBU), 1,5-diazabicyclo[4.3.0]non-5-ene (DBN), and 1,4-diazabicyclo[2.2.2]octane (DABCO); and hydroxide salts such as sodium hydroxide, potassium hydroxide, tetramethylammonium hydroxide, and tetrapropylammonium hydroxide. Suitable organic solvents include polar solvents such as ethanol, isopropyl alcohol, acetone, methyl ethyl ketone, methyl isobutyl ketone, acetonitrile, N,N-dimethylformamide (DMF), and dimethyl sulfoxide (DMSO); and aromatic hydrocarbon solvents such as benzene, toluene, and xylene, which may be used alone or in admixture.

A second method for preparing the fluorinated cyclic structure-bearing silicone resins of the invention is by carbon-to-silicon bond-forming reactions of reactive silicone resins with fluoro-hemiacetal derivatives. Of these reactions, preference is given to hydrosilylation reaction of SiH-containing silicone resins (e.g., MQ cage oligosiloxane having SiH group at M end) with fluoro-hemiacetal derivatives having an unsaturated bond, especially a double bond. The fluoro-hemiacetal derivatives having an unsaturated bond used herein may be those described as the starting reactant in the preparation of the silane monomers. Even in the preparation of silicone resins by the second method, using a derivative having an unsaturated bond corresponding to that described as the comonomer in the first method (cohydrolytic condensation reaction), carbon-to-silicon bond-forming reaction such as hydrosilylation reaction can be performed at the same time as the reaction of the fluoro-hemiacetal derivative having an unsaturated bond whereby a fluorinated cyclic structure-bearing silicone resin having the same composition as in the first method is produced.

The fluorinated cyclic structure-bearing silicone resins should preferably have a weight average molecular weight (Mw) of 1,000 to 100,000, more preferably 1,000 to 30,000, and even more preferably 1,500 to 20,000, as measured by gel permeation chromatography (GPC) versus polystyrene standards. Resins having a Mw in excess of 100,000 may be difficult to purify, and resins having a Mw in excess of 30,000 tend to decline in resist composition resolution, though depending on a combination of monomers. Resins having a Mw of less than 1,500 tend to have a degraded pattern profile, and resins having a Mw of less than 1,000 may have more tendency.

The fluorinated cyclic structure-bearing silicone resins of the invention are fully transparent to radiation having a wavelength of up to 500 nm, especially up to 300 nm, exhibit improved development performance due to the inclusion of appropriate acidic hydroxyl groups, and thus find best use as the base resin in radiation-sensitive resist compositions. Examples of the radiation having a wavelength of up to 300 nm include ArF laser (193 nm), $F_2$ laser (157 nm), $Ar_2$ laser (126 nm), and extreme ultraviolet (EUV, 13 nm). The exposure system may be either conventional dry exposure or immersion exposure. In the immersion lithography, the liquid fill between the wafer and the projection lens should have a higher refractive index and high transparency, with water having a refractive index of 1.44 at wavelength 193 nm being often used. For better resolution, liquids having a refractive index of 1.6 or higher such as phosphoric acid, ethylene glycol and trialkoxyaluminum may also be used.

Resist Composition

The present invention in the third aspect provides a resist composition comprising (A) the above-described silicone resin as a base resin, (B) a photoacid generator, (C) an organic solvent, and optionally (D) a nitrogen-containing organic compound.

Component B

The photoacid generator (B) may be any compound capable of generating an acid upon exposure to high energy radiation having a wavelength of up to 300 nm or electron beam as long as a resist composition comprising the photoacid generator, the inventive resin and an organic solvent can be a homogeneous solution which is effectively applicable to form a uniform film.

Examples of the photoacid generator which can be used herein include:

(i) onium salts of the formula (P1a-1), (P1a-2) or (P1b), (ii) diazomethane derivatives of the formula (P2), (iii) glyoxime derivatives of the formula (P3), (iv) bissulfone derivatives of the formula (P4), (v) sulfonic acid esters of N-hydroxyimide compounds of the formula (P5), (vi) β-ketosulfonic acid derivatives, (vii) disulfone derivatives, (viii) nitrobenzylsulfonate derivatives, (ix) sulfonate derivatives, and (x) oxime sulfonates.

These photoacid generators are described in detail.

(i) Onium Salts of Formula (P1a-1), (P1a-2) or (P1b):

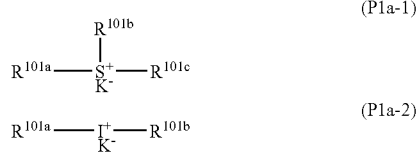

Herein, $R^{101a}$, $R^{101b}$, and $R^{101c}$ independently represent straight, branched or cyclic alkyl, alkenyl or oxoalkyl groups of 1 to 12 carbon atoms, aryl groups of 6 to 20 carbon atoms, or aralkyl or aryloxoalkyl groups of 7 to 12 carbon atoms, wherein some or all of the hydrogen atoms may be replaced by alkoxy or other groups. Also, $R^{101b}$ and $R^{101c}$, taken together, may form a ring. $R^{101b}$ and $R^{101c}$ each are alkylene groups of 1 to 6 carbon atoms when they form a ring. $K^-$ is a non-nucleophilic counter ion.

$R^{101a}$, $R^{101b}$, and $R^{101c}$ may be the same or different and are illustrated below. Exemplary alkyl groups include methyl, ethyl, propyl, isopropyl, n-butyl; sec-butyl, tert-butyl, pentyl, hexyl, heptyl, octyl, cyclopentyl, cyclohexyl, cycloheptyl, cyclopropylmethyl, 4-methylcyclohexyl, cyclohexylmethyl, norbornyl, and adamantyl. Exemplary alkenyl groups include vinyl, allyl, propenyl, butenyl, hexenyl, and cyclohexenyl. Exemplary oxoalkyl groups include 2-oxocyclopentyl and 2-oxocyclohexyl as well as 2-oxopropyl, 2-cyclopentyl-2-oxoethyl, 2-cyclohexyl-2-oxoethyl, and 2-(4-methylcyclohexyl)-2-oxoethyl. Exemplary aryl groups include phenyl and naphthyl; alkoxyphenyl groups such as p-methoxyphenyl, m-methoxyphenyl, o-methoxyphenyl, ethoxyphenyl, p-tert-butoxyphenyl, and m-tert-butoxyphenyl; alkylphenyl groups such as 2-methylphenyl, 3-methylphenyl, 4-methylphenyl, ethylphenyl, 4-tert-butylphenyl, 4-butylphenyl, and dimethylphenyl; alkylnaphthyl groups such as methylnaphthyl and ethylnaphthyl; alkoxynaphthyl groups such as methoxynaphthyl and ethoxynaphthyl; dialkylnaphthyl groups such as dimethylnaphthyl and diethylnaphthyl; and dialkoxynaphthyl groups such as dimethoxynaphthyl and diethoxynaphthyl. Exemplary aralkyl groups include benzyl, phenylethyl, and phenethyl. Exemplary aryloxoalkyl groups are 2-aryl-2-oxoethyl groups such as 2-phenyl-2-oxoethyl, 2-(1-naphthyl)-2-oxoethyl, and 2-(2-naphthyl)-2-oxoethyl. Examples of the non-nucleophilic counter ion represented by $K^-$ include halide ions such as chloride and bromide ions, fluoroalkylsulfonate ions such as triflate, 1,1,1-trifluoroethanesulfonate, and nonafluorobutanesulfonate, arylsulfonate ions such as tosylate, benzenesulfonate, 4-fluorobenzenesulfonate, and 1,2,3,4,5-pentafluorobenzenesulfonate, and alkylsulfonate ions such as mesylate and butanesulfonate.

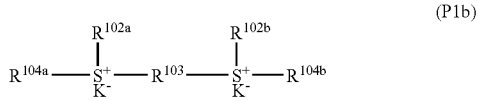

Herein, $R^{102a}$ and $R^{102b}$ independently represent straight, branched or cyclic alkyl groups of 1 to 8 carbon atoms. $R^{103}$ represents a straight, branched or cyclic alkylene group of 1 to 10 carbon atoms. $R^{104a}$ and $R^{104b}$ independently represent 2-oxoalkyl groups of 3 to 7 carbon atoms. $K^-$ is a non-nucleophilic counter ion.

Illustrative of the groups represented by $R^{102a}$ and $R^{102b}$ are methyl, ethyl, propyl, isopropyl, n-butyl, sec-butyl, tert-butyl, pentyl, hexyl, heptyl, octyl, cyclopentyl, cyclohexyl, cyclopropylmethyl, 4-methylcyclohexyl, and cyclohexylmethyl. Illustrative of the groups represented by $R^{103}$ are methylene, ethylene, propylene, butylene, pentylene, hexylene, heptylene, octylene, nonylene, 1,4-cyclohexylene, 1,2-cyclohexylene, 1,3-cyclopentylene, 1,4-cyclooctylene, and 1,4-cyclohexanedimethylene. Illustrative of the groups represented by $R^{104a}$ and $R^{104b}$ are 2-oxopropyl, 2-oxocyclopentyl, 2-oxocyclohexyl, and 2-oxocycloheptyl. Illustrative examples of the counter ion represented by $K^-$ are the same as exemplified for formulae (P1a-1) and (P1a-2).

(ii) Diazomethane Derivatives of Formula (P2)

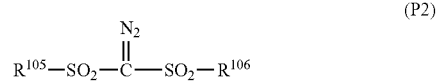

Herein, $R^{105}$ and $R^{106}$ independently represent straight, branched or cyclic alkyl or halogenated alkyl groups of 1 to 12 carbon atoms, aryl or halogenated aryl groups of 6 to 20 carbon atoms, or aralkyl groups of 7 to 12 carbon atoms.

Of the groups represented by $R^{105}$ and $R^{106}$, exemplary alkyl groups include methyl, ethyl, propyl, isopropyl, n-butyl, sec-butyl, tert-butyl, pentyl, hexyl, heptyl, octyl, amyl, cyclopentyl, cyclohexyl, cycloheptyl, norbornyl, and adamantyl. Exemplary halogenated alkyl groups include trifluoromethyl, 1,1,1-trifluoroethyl, 1,1,1-trichloroethyl, and nonafluorobutyl. Exemplary aryl groups include phenyl; alkoxyphenyl groups such as p-methoxyphenyl, m-methoxyphenyl, o-methoxyphenyl, ethoxyphenyl, p-tert-butoxyphenyl, and m-tert-butoxyphenyl; and alkylphenyl groups such as 2-methylphenyl, 3-methylphenyl, 4-methylphenyl, ethylphenyl, 4-tert-butylphenyl, 4-butylphenyl, and dimethylphenyl. Exemplary halogenated aryl groups include fluorophenyl, chlorophenyl, and 1,2,3,4,5-pentafluorophenyl. Exemplary aralkyl groups include benzyl and phenethyl.

(iii) Glyoxime Derivatives of Formula (P3)

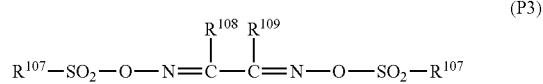

Herein, $R^{107}$, $R^{108}$, and $R^{109}$ independently represent straight, branched or cyclic alkyl or halogenated alkyl groups of 1 to 12 carbon atoms, aryl or halogenated aryl groups of 6 to 20 carbon atoms, or aralkyl groups of 7 to 12 carbon atoms. Also, $R^{108}$ and $R^{109}$, taken together, may form a ring. $R^{108}$ and $R^{109}$ each are straight or branched alkylene groups of 1 to 6 carbon atoms when they form a ring.

Illustrative examples of the alkyl, halogenated alkyl, aryl, halogenated aryl, and aralkyl groups represented by $R^{107}$, $R^{108}$, and $R^{109}$ are the same as exemplified for $R^{105}$ and $R^{106}$. Examples of the alkylene groups represented by $R^{108}$ and $R^{109}$ include methylene, ethylene, propylene, butylene, and hexylene.

(iv) Bissulfone Derivatives of Formula (P4)

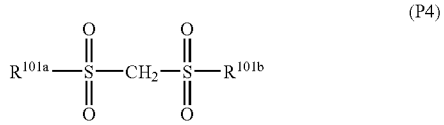

Herein, $R^{101a}$ and $R^{101b}$ are as defined above.

(v) Sulfonic Acid Esters of N-Hydroxyimide Compounds of Formula (P5)

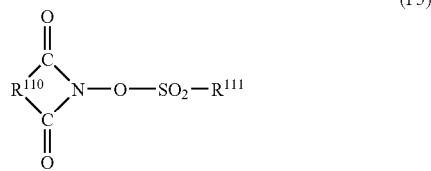

Herein, $R^{110}$ is an arylene group of 6 to 10 carbon atoms, alkylene group of 1 to 6 carbon atoms, or alkenylene group of 2 to 6 carbon atoms wherein some or all of the hydrogen atoms may be replaced by straight or branched alkyl or alkoxy groups of 1 to 4 carbon atoms, nitro, acetyl, or phenyl groups. $R^{111}$ is a straight, branched or cyclic alkyl group of 1 to 8 carbon atoms, alkenyl, alkoxyalkyl, phenyl or naphthyl group wherein some or all of the hydrogen atoms may be replaced by alkyl or alkoxy groups of 1 to 4 carbon atoms, phenyl groups (which may have substituted thereon an alkyl or alkoxy of 1 to 4 carbon atoms, nitro, or acetyl group), hetero-aromatic groups of 3 to 5 carbon atoms, or chlorine or fluorine atoms.

Of the groups represented by $R^{110}$, exemplary arylene groups include 1,2-phenylene and 1,8-naphthylene; exemplary alkylene groups include methylene, ethylene, trimethylene, tetramethylene, phenylethylene, and norbornane-2,3-diyl; and exemplary alkenylene groups include 1,2-vinylene, 1-phenyl-1,2-vinylene, and 5-norbornene-2,3-diyl. Of the groups represented by $R^{111}$, exemplary alkyl groups are as exemplified for $R^{101a}$ to $R^{101c}$; exemplary alkenyl groups include vinyl, 1-propenyl, allyl, 1-butenyl, 3-butenyl, isoprenyl, 1-pentenyl, 3-pentenyl, 4-pentenyl, dimethylallyl, 1-hexenyl, 3-hexenyl, 5-hexenyl, 1-heptenyl, 3-heptenyl, 6-heptenyl, and 7-octenyl; and exemplary alkoxyalkyl groups include methoxymethyl, ethoxymethyl, propoxymethyl, butoxymethyl, pentyloxymethyl, hexyloxymethyl, heptyloxymethyl, methoxyethyl, ethoxyethyl, propoxyethyl, butoxyethyl, pentyloxyethyl, hexyloxyethyl, methoxypropyl, ethoxypropyl, propoxypropyl, butoxypropyl, methoxybutyl, ethoxybutyl, propoxybutyl, methoxypentyl, ethoxypentyl, methoxyhexyl, and methoxyheptyl.

Of the substituents on these groups, the alkyl groups of 1 to 4 carbon atoms include methyl, ethyl, propyl, isopropyl, n-butyl, isobutyl and tert-butyl; and the alkoxy groups of 1 to 4 carbon atoms include methoxy, ethoxy, propoxy, isopropoxy, n-butoxy, isobutoxy, and tert-butoxy. The phenyl groups which may have substituted thereon an alkyl or alkoxy of 1 to 4 carbon atoms, nitro, or acetyl group include phenyl, tolyl, p-tert-butoxyphenyl, p-acetylphenyl and p-nitrophenyl. The hetero-aromatic groups of 3 to 5 carbon atoms include pyridyl and furyl.

Illustrative examples of the photoacid generator include:
onium salts such as
diphenyliodonium trifluoromethanesulfonate,
(p-tert-butoxyphenyl)phenyliodonium trifluoromethane-sulfonate,
diphenyliodonium p-toluenesulfonate,
(p-tert-butoxyphenyl)phenyliodonium p-toluenesulfonate,
triphenylsulfonium trifluoromethanesulfonate,
(p-tert-butoxyphenyl)diphenylsulfonium trifluoromethane-sulfonate,
bis(p-tert-butoxyphenyl)phenylsulfonium trifluoromethane-sulfonate,
tris(p-tert-butoxyphenyl)sulfonium trifluoromethane-sulfonate,
triphenylsulfonium p-toluenesulfonate,
(p-tert-butoxyphenyl)diphenylsulfonium p-toluene-sulfonate,
bis(p-tert-butoxyphenyl)phenylsulfonium p-toluene-sulfonate,
tris(p-tert-butoxyphenyl)sulfonium p-toluenesulfonate,
triphenylsulfonium nonafluorobutanesulfonate,
triphenylsulfonium butanesulfonate,
trimethylsulfonium trifluoromethanesulfonate,
trimethylsulfonium p-toluenesulfonate,
cyclohexylmethyl(2-oxocyclohexyl)sulfonium trifluoromethane-sulfonate,
cyclohexylmethyl(2-oxocyclohexyl)sulfonium p-toluene-sulfonate,
dimethylphenylsulfonium trifluoromethanesulfonate,
dimethylphenylsulfonium p-toluenesulfonate,
dicyclohexylphenylsulfonium trifluoromethanesulfonate,
dicyclohexylphenylsulfonium p-toluenesulfonate,
trinaphthylsulfonium trifluoromethanesulfonate,
cyclohexylmethyl(2-oxocyclohexyl)sulfonium trifluoromethane-sulfonate,
(2-norbornyl)methyl(2-oxocyclohexyl)sulfonium trifluoromethanesulfonate,
ethylenebis[methyl(2-oxocyclopentyl)sulfonium trifluoromethanesulfonate], and
1,2'-naphthylcarbonylmethyltetrahydrothiophenium triflate; diazomethane derivatives such as
bis(benzenesulfonyl)diazomethane,
bis(p-toluenesulfonyl)diazomethane,
bis(xylenesulfonyl)diazomethane,
bis(cyclohexylsulfonyl)diazomethane,
bis(cyclopentylsulfonyl)diazomethane,
bis(n-butylsulfonyl)diazomethane,
bis(isobutylsulfonyl)diazomethane,
bis(sec-butylsulfonyl)diazomethane,
bis(n-propylsulfonyl)diazomethane,
bis(isopropylsulfonyl)diazomethane,
bis(tert-butylsulfonyl)diazomethane,
bis(n-amylsulfonyl)diazomethane,
bis(isoamylsulfonyl)diazomethane,
bis(sec-amylsulfonyl)diazomethane,
bis(tert-amylsulfonyl)diazomethane,
1-cyclohexylsulfonyl-1-(tert-butylsulfonyl)diazomethane,
1-cyclohexylsulfonyl-1-(tert-amylsulfonyl)diazomethane, and
1-tert-amylsulfonyl-1-(tert-butylsulfonyl)diazomethane; glyoxime derivatives such as
bis-O-(p-toluenesulfonyl)-α-dimethylglyoxime,
bis-O-(p-toluenesulfonyl)-α-diphenylglyoxime,
bis-O-(p-toluenesulfonyl)-α-dicyclohexylglyoxime,
bis-O-(p-toluenesulfonyl)-2,3-pentanedioneglyoxime,
bis-O-(p-toluenesulfonyl)-2-methyl-3,4-pentanedioneglyoxime, bis-O-(n-butanesulfonyl)-α-dimethylglyoxime,
bis-O-(n-butanesulfonyl)-α-diphenylglyoxime,
bis-O-(n-butanesulfonyl)-α-dicyclohexylglyoxime,
bis-O-(n-butanesulfonyl)-2,3-pentanedioneglyoxime,
bis-O-(n-butanesulfonyl)-2-methyl-3,4-pentanedioneglyoxime,
bis-O-(methanesulfonyl)-α-dimethylglyoxime,
bis-O-(trifluoromethanesulfonyl)-α-dimethylglyoxime,
bis-O-(1,1,1-trifluoroethanesulfonyl)-α-dimethylglyoxime,
bis-O-(tert-butanesulfonyl)-α-dimethylglyoxime,
bis-O-(perfluorooctanesulfonyl)-α-dimethylglyoxime,
bis-O-(cyclohexanesulfonyl)-α-dimethylglyoxime,
bis-O-(benzenesulfonyl)-α-dimethylglyoxime,
bis-O-(p-fluorobenzenesulfonyl)-α-dimethylglyoxime,
bis-O-(p-tert-butylbenzenesulfonyl)-α-dimethylglyoxime,
bis-O-(xylenesulfonyl)-α-dimethylglyoxime, and
bis-O-(camphorsulfonyl)-α-dimethylglyoxime;
    bissulfone derivatives such as
bisnaphthylsulfonylmethane, bistrifluoromethylsulfonylmethane,
bismethylsulfonylmethane, bisethylsulfonylmethane,
bispropylsulfonylmethane, bisisopropylsulfonylmethane,
bis-p-toluenesulfonylmethane, and bisbenzenesulfonylmethane;
    β-ketosulfone derivatives such as
2-cyclohexylcarbonyl-2-(p-toluenesulfonyl)propane and
2-isopropylcarbonyl-2-(p-toluenesulfonyl)propane;
    nitrobenzyl sulfonate derivatives such as
2,6-dinitrobenzyl p-toluenesulfonate and
2,4-dinitrobenzyl p-toluenesulfonate;
    sulfonic acid ester derivatives such as
1,2,3-tris(methanesulfonyloxy)benzene,
1,2,3-tris(trifluoromethanesulfonyloxy)benzene, and
1,2,3-tris(p-toluenesulfonyloxy)benzene; and
    sulfonic acid esters of N-hydroxyimides such as
N-hydroxysuccinimide methanesulfonate,
N-hydroxysuccinimide trifluoromethanesulfonate,
N-hydroxysuccinimide ethanesulfonate,
N-hydroxysuccinimide 1-propanesulfonate,
N-hydroxysuccinimide 2-propanesulfonate,
N-hydroxysuccinimide 1-pentanesulfonate,
N-hydroxysuccinimide 1-octanesulfonate,
N-hydroxysuccinimide p-toluenesulfonate,
N-hydroxysuccinimide p-methoxybenzenesulfonate,
N-hydroxysuccinimide 2-chloroethanesulfonate,
N-hydroxysuccinimide benzenesulfonate,
N-hydroxysuccinimide 2,4,6-trimethylbenzenesulfonate,
N-hydroxysuccinimide 1-naphthalenesulfonate,
N-hydroxysuccinimide 2-naphthalenesulfonate,
N-hydroxy-2-phenylsuccinimide methanesulfonate,
N-hydroxymaleimide methanesulfonate,
N-hydroxymaleimide ethanesulfonate,
N-hydroxy-2-phenylmaleimide methanesulfonate,
N-hydroxyglutarimide methanesulfonate,
N-hydroxyglutarimide benzenesulfonate,
N-hydroxyphthalimide methanesulfonate,
N-hydroxyphthalimide benzenesulfonate,
N-hydroxyphthalimide trifluoromethanesulfonate,
N-hydroxyphthalimide p-toluenesulfonate,
N-hydroxynaphthalimide methanesulfonate,
N-hydroxynaphthalimide benzenesulfonate,
N-hydroxy-5-norbornene-2,3-dicarboxyimide methanesulfonate,
N-hydroxy-5-norbornene-2,3-dicarboxyimide trifluoromethane-sulfonate, and
N-hydroxy-5-norbornene-2,3-dicarboxyimide p-toluenesulfonate.

Preferred among these photoacid generators are onium salts such as triphenylsulfonium trifluoromethanesulfonate,
(p-tert-butoxyphenyl)diphenylsulfonium trifluoromethanesulfonate,
tris(p-tert-butoxyphenyl)sulfonium trifluoromethanesulfonate,
triphenylsulfonium p-toluenesulfonate,
(p-tert-butoxyphenyl)diphenylsulfonium p-toluenesulfonate,
tris(p-tert-butoxyphenyl)sulfonium p-toluenesulfonate,
trinaphthylsulfonium trifluoromethanesulfonate,
cyclohexylmethyl(2-oxocyclohexyl)sulfonium trifluoromethane-sulfonate,
(2-norbornyl)methyl(2-oxocylohexyl)sulfonium trifluoromethanesulfonate, and
1,2'-naphthylcarbonylmethyltetrahydrothiophenium triflate;

diazomethane derivatives such as
bis(benzenesulfonyl)diazomethane,
bis(p-toluenesulfonyl)diazomethane,
bis(cyclohexylsulfonyl)diazomethane,
bis(n-butylsulfonyl)diazomethane,
bis(isobutylsulfonyl)diazomethane,
bis(sec-butylsulfonyl)diazomethane,
bis(n-propylsulfonyl)diazomethane,
bis(isopropylsulfonyl)diazomethane, and
bis(tert-butylsulfonyl)diazomethane;

glyoxime derivatives such as
bis-O-(p-toluenesulfonyl)-α-dimethylglyoxime and
bis-O-(n-butanesulfonyl)-α-dimethylglyoxime;
bissulfone derivatives such as bisnaphthylsulfonylmethane;

and sulfonic acid esters of N-hydroxyimide compounds such as
N-hydroxysuccinimide methanesulfonate,
N-hydroxysuccinimide trifluoromethanesulfonate,
N-hydroxysuccinimide 1-propanesulfonate,
N-hydroxysuccinimide 2-propanesulfonate,
N-hydroxysuccinimide 1-pentanesulfonate,
N-hydroxysuccinimide p-toluenesulfonate,
N-hydroxynaphthalimide methanesulfonate, and
N-hydroxynaphthalimide benzenesulfonate.
    Also included are the oxime sulfonates described in U.S. Pat. No. 6,004,724, for example,
(5-(4-toluenesulfonyl)oxyimino-5H-thiophen-2-ylidene)-phenylacetonitrile,
(5-(10-camphorsulfonyl)oxyimino-5H-thiophen-2-ylidene)phenylacetonitrile,
(5-n-octanesulfonyloxyimino-5H-thiophen-2-ylidene)phenylacetonitrile,
(5-(4-toluenesulfonyl)oxyimino-5H-thiophen-2-ylidene)(2-methylphenyl)acetonitrile,
(5-(10-camphorsulfonyl)oxyimino-5H-thiophen-2-ylidene)(2-methylphenyl)acetonitrile,
(5-n-octanesulfonyloxyimino-5H-thiophen-2-ylidene)(2-methylphenyl)acetonitrile, etc.
    Also included are the oxime sulfonates described in U.S. Pat. No. 6,261,738 and JP-A 2000-314956, for example, 2,2,2-trifluoro-1-phenyl-ethanone oxime-O-methylsulfonate; 2,2,2-trifluoro-1-phenyl-ethanone oxime-O-(10-camphorylsulfonate); 2,2,2-trifluoro-1-phenyl-ethanone oxime-O-(4-methoxyphenylsulfonate); 2,2,2-trifluoro-1-phenyl-ethanone oxime-O-(1-naphthylsulfonate); 2,2,2-trifluoro-1-phenyl-ethanone oxime-O-(2-naphthylsulfonate); 2,2,2-trifluoro-1-phenyl-ethanone oxime-O-(2,4,6-trimethylphenylsulfonate); 2,2,2-trifluoro-1-(4-methylphenyl)-ethanone oxime-O-(10- camphorylsulfonate); 2,2,2-trifluoro-1-(4-methylphenyl))-ethanone oxime-O-(methylsulfonate); 2,2,2-trifluoro-1-(2-methylphenyl)-ethanone oxime-O-(10-camphorylsulfonate); 2,2,2-trifluoro-1-(2,4-dimethylphenyl)-ethanone oxime-O-(10-camphorylsulfonate); 2,2,2-trifluoro-1-(2,4-dimethylphenyl)-ethanone oxime-O-(1-naphthylsulfonate); 2,2,2-trifluoro-1-(2,4-dimethylphenyl)-ethanone oxime-O-(2-naphthylsulfonate); 2,2,2-trifluoro-1-(2,4,6-trimethylphenyl)-ethanone oxime-O-(10-camphorylsulfonate); 2,2,2-trifluoro-1-(2,4,6-trimethylphenyl)-ethanone oxime-O-(1-naphthylsulfonate); 2,2,2-trifluoro-1-(2,4,6-trimethylphenyl)-ethanone oxime-O-(2-naphthylsulfonate); 2,2,2-trifluoro-1-(4-methoxyphenyl)-ethanone oxime-O-methylsulfonate; 2,2,2-trifluoro-1-(4-methylthiophenyl)-ethanone oxime-O-methylsulfonate; 2,2,2-trifluoro-1-(3,4-dimethoxyphenyl)-ethanone oxime-O-methylsulfonate; 2,2,3,3,4,4,4-heptafluoro-1-phenyl-butanone oxime-O-(10-camphorylsulfonate); 2,2,2-trifluoro-1-(phenyl)-ethanone oxime-O-methylsulfonate; 2,2,2-trifluoro-1-(phenyl)-ethanone oxime-O-10-camphorylsulfonate; 2,2,2-trifluoro-1-(phenyl)-ethanone oxime-O-(4-methoxyphenyl)sulfonate; 2,2,2-trifluoro-1-(phenyl)-ethanone oxime-O-(1-naphthyl)sulfonate; 2,2,2-trifluoro-1-(phenyl)-ethanone oxime-O-(2-naphthyl)sulfonate; 2,2,2-trifluoro-1-(phenyl)-ethanone oxime-O-(2,4,6-trimethylphenyl)sulfonate; 2,2,2-trifluoro-1-(4-methylphenyl)-ethanone oxime-O-(10-camphoryl)sulfonate; 2,2,2-trifluoro-1-(4-methylphenyl)-ethanone oxime-O-methylsulfonate; 2,2,2-trifluoro-1-(2-methylphenyl)-ethanone oxime-O-(10-camphoryl)sulfonate; 2,2,2-trifluoro-1-(2,4-dimethylphenyl)-ethanone oxime-O-(1-naphthyl)sulfonate; 2,2,2-trifluoro-1-(2,4-dimethylphenyl)-ethanone oxime-O-(2-naphthyl)sulfonate; 2,2,2-trifluoro-1-(2,4,6-trimethylphenyl)-ethanone oxime-O-(10-camphoryl)sulfonate; 2,2,2-trifluoro-1-(2,4,6-trimethylphenyl)-ethanone oxime-O-(1-naphthyl)sulfonate; 2,2,2-trifluoro-1-(2,4,6-trimethylphenyl)-ethanone oxime-O-(2-naphthyl)sulfonate; 2,2,2-trifluoro-1-(4-methoxyphenyl)-ethanone oxime-O-methylsulfonate; 2,2,2-trifluoro-1-(4-thiomethylphenyl)-ethanone oxime-O-methylsulfonate; 2,2,2-trifluoro-1-(3,4-dimethoxyphenyl)-ethanone oxime-O-methylsulfonate; 2,2,2-trifluoro-1-(4-methoxyphenyl)-ethanone oxime-O-(4-methylphenyl)sulfonate; 2,2,2-trifluoro-1-(4-methoxyphenyl)-ethanone oxime-O-(4-methoxyphenyl)sulfonate; 2,2,2-trifluoro-1-(4-methoxyphenyl)-ethanone oxime-O-(4-dodecylphenyl)-sulfonate; 2,2,2-trifluoro-1-(4-methoxyphenyl)-ethanone oxime-O-octylsulfonate; 2,2,2-trifluoro-1-(4-thiomethyl-phenyl)-ethanone oxime-O-(4-methoxyphenyl)sulfonate; 2,2,2-trifluoro-1-(4-thiomethylphenyl)-ethanone oxime-O-(4-dodecylphenyl)sulfonate; 2,2,2-trifluoro-1-(4-thiomethyl-phenyl)-ethanone oxime-O-octylsulfonate; 2,2,2-trifluoro-1-(4-thiomethylphenyl)-ethanone oxime-O-(2-naphthyl)sulfonate; 2,2,2-trifluoro-1-(2-methylphenyl)-ethanone oxime-O-methylsulfonate; 2,2,2-trifluoro-1-(4-methylphenyl)ethanone oxime-O-phenylsulfonate; 2,2,2-trifluoro-1-(4-chlorophenyl)-ethanone oxime-O-phenylsulfonate; 2,2,3,3,4,4,4-heptafluoro-1-(phenyl)-butanone oxime-O-(10-camphoryl)sulfonate; 2,2,2-trifluoro-1-naphthyl-ethanone oxime-O-methylsulfonate; 2,2,2-trifluoro-2-naphthyl-ethanone oxime-O-methylsulfonate; 2,2,2-trifluoro-1-[4-benzylphenyl]-ethanone oxime-O-methylsulfonate; 2,2,2-trifluoro-1-[4-(phenyl-1,4-dioxa-but-1-yl)phenyl]-ethanone oxime-O-methylsulfonate; 2,2,2-trifluoro-1-naphthyl-ethanone oxime-O-propylsulfonate; 2,2,2-trifluoro-2-naphthyl-ethanone oxime-O-propylsulfonate; 2,2,2-trifluoro-1-[4-benzylphenyl]-ethanone oxime-O-propyl-sulfonate; 2,2,2-trifluoro-1-[4-methylsulfonylphenyl]-ethanone oxime-O-propylsulfonate; 1,3-bis[1-(4-phenoxyphenyl)-2,2,2-trifluoroethanone oxime-O-sulfonyl]phenyl; 2,2,2-trifluoro-1-[4-methylsulfonyl-oxyphenyl]-ethanone oxime-O-propylsulfonate; 2,2,2-trifluoro-1-[4-methylcarbonyloxyphenyl]-ethanone oxime-O-propylsulfonate; 2,2,2-trifluoro-1-[6H,7H-5,8-dioxonaphth-2-yl]-ethanone oxime-O-propylsulfonate; 2,2,2-trifluoro-1-[4-methoxycarbonylmethoxyphenyl]-ethanone oxime-O-propylsulfonate; 2,2,2-trifluoro-1-[4-(methoxycarbonyl)-(4-amino-1-oxa-pent-1-yl)-phenyl]-ethanone oxime-O-propylsulfonate; 2,2,2-trifluoro-1-[3,5-dimethyl-4-ethoxyphenyl]-ethanone oxime-O-propylsulfonate; 2,2,2-trifluoro-1-[4-benzyloxyphenyl]-ethanone oxime-O-propylsulfonate; 2,2,2-trifluoro-1-[2-thiophenyl]-ethanone oxime-O-propylsulfonate; and 2,2,2-trifluoro-1-[1-dioxathiophen-2-yl)]-ethanone oxime-O-propylsulfonate.

Also included are the oxime sulfonates described in JP-A 9-95479 and JP-A 9-230588 and the references cited therein, for example, α-(p-toluenesulfonyloxyimino)-phenylacetonitrile,
α-(p-chlorobenzenesulfonyloxyimino)-phenylacetonitrile,
α-(4-nitrobenzenesulfonyloxyimino)-phenylacetonitrile,
α-(4-nitro-2-trifluoromethylbenzenesulfonyloxyimino)-phenylacetonitrile,
α-(benzenesulfonyloxyimino)-4-chlorophenylacetonitrile,
α-(benzenesulfonyloxyimino)-2,4-dichlorophenylacetonitrile,
α-(benzenesulfonyloxyimino)-2,6-dichlorophenylacetonitrile,
α-(benzenesulfonyloxyimino)-4-methoxyphenylacetonitrile,
α-(2-chlorobenzenesulfonyloxyimino)-4-methoxyphenylacetonitrile,
α-(benzenesulfonyloxyimino)-2-thienylacetonitrile,
α-(4-dodecylbenzenesulfonyloxyimino)-phenylacetonitrile,
α-[(4-toluenesulfonyloxyimino)-4-methoxyphenyl]acetonitrile,
α-[(dodecylbenzenesulfonyloxyimino)-4-methoxyphenyl]-acetonitrile,
α-(tosyloxyimino)-3-thienylacetonitrile,
α-(methylsulfonyloxyimino)-1-cyclopentenylacetonitrile,
α-(ethylsulfonyloxyimino)-1-cyclopentenylacetonitrile,
α-(isopropylsulfonyloxyimino)-1-cyclopentenylacetonitrile,
α-(n-butylsulfonyloxyimino)-1-cyclopentenylacetonitrile,
α-(ethylsulfonyloxyimino)-1-cyclohexenylacetonitrile,
α-(isopropylsulfonyloxyimino)-1-cyclohexenylacetonitrile, and
α-(n-butylsulfonyloxyimino)-1-cyclohexenylacetonitrile.

Suitable bisoxime sulfonates include those described in JP-A 9-208554, for example, bis(α-(4-toluenesulfonyloxy)imino)-p-phenylenediacetonitrile,
bis(α-(benzenesulfonyloxy)imino)-p-phenylenediacetonitrile,
bis(α-(methanesulfonyloxy)imino)-p-phenylenediacetonitrile,
bis(α-(butanesulfonyloxy)imino)-p-phenylenediacetonitrile,
bis(α-(10-camphorsulfonyloxy)imino)-p-phenylenediacetonitrile,
bis(α-(4-toluenesulfonyloxy)imino)-p-phenylenediacetonitrile,
bis(α-(trifluoromethanesulfonyloxy)imino)-p-phenylene-diacetonitrile,
bis(α-(4-methoxybenzenesulfonyloxy)imino)-p-phenylenediacetonitrile,
bis(α-(4-toluenesulfonyloxy)imino)-m-phenylenediacetonitrile, bis(α-(benzenesulfonyloxy)imino)-m-phenylenediacetonitrile,
bis(α-(methanesulfonyloxy)imino)-m-phenylenediacetonitrile,
bis(α-(butanesulfonyloxy)imino)-m-phenylenediacetonitrile,
bis(α-(10-camphorsulfonyloxy)imino)-m-phenylenediacetonitrile,
bis(α-(4-toluenesulfonyloxy)imino)-m-phenylenediacetonitrile,
bis(α-(trifluoromethanesulfonyloxy)imino)-m-phenylenediacetonitrile,
bis(α-(4-methoxybenzenesulfonyloxy)imino)-m-phenylene-diacetonitrile, etc.

These photoacid generators may be used singly or in combinations of two or more thereof. Onium salts are effective for improving rectangularity, while diazomethane derivatives and glyoxime derivatives are effective for reducing standing waves. The combination of an onium salt with a diazomethane or a glyoxime derivative allows for fine adjustment of the profile.

The photoacid generator is added in an amount of 0.1 to 50 parts, and especially 0.5 to 40 parts by weight, per 100 parts by weight of the base resin (all parts are by weight, hereinafter). Less than 0.1 part of the photoacid generator may generate a less amount of acid upon exposure, sometimes leading to a poor sensitivity and resolution whereas more than 50 parts of the photoacid generator may adversely affect the transmittance and resolution of resist.

Component C

The organic solvent (C) used herein may be any organic solvent in which the base resin, photoacid generator, and other components are soluble. Illustrative, non-limiting, examples of the organic solvent include ketones such as cyclohexanone and methyl isopentyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone. These solvents may be used alone or in combinations of two or more thereof. Of the above organic solvents, it is recommended to use diethylene glycol dimethyl ether, 1-ethoxy-2-propanol, propylene glycol monomethyl ether acetate, cyclohexanone, or a mixture thereof because the photoacid generator is most soluble therein.

An appropriate amount of the organic solvent used is about 200 to 1,000 parts, especially about 400 to 800 parts by weight per 100 parts by weight of the base resin.

Component D

The nitrogen-containing organic compound (D) is preferably a compound capable of suppressing the rate of diffusion when the acid generated by the photoacid generator diffuses within the resist film. The inclusion of the nitrogen-containing organic compound holds down the rate of acid diffusion within the resist film, resulting in better resolution. In addition, it suppresses changes in sensitivity following exposure, thus reducing substrate and environment dependence, as well as improving the exposure latitude and the pattern profile.

Examples of suitable nitrogen-containing organic compounds include primary, secondary, and tertiary aliphatic amines, mixed amines, aromatic amines, heterocyclic amines, nitrogen-containing compounds having carboxyl group, nitrogen-containing compounds having sulfonyl group, nitrogen-containing compounds having hydroxyl group, nitrogen-containing compounds having hydroxyphenyl group, alcoholic nitrogen-containing compounds, amide derivatives, imide derivatives, and carbamates.

Examples of suitable primary aliphatic amines include ammonia, methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine.

Examples of suitable secondary aliphatic amines include dimethylamine, diethylamine, di-n-propylamine, di-isopropylamine, di-n-butylamine, diisobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N,N-dimethyltetraethylenepentamine.

Examples of suitable tertiary aliphatic amines include trimethylamine, triethylamine, tri-n-propylamine, triisopropylamine, tri-n-butylamine, triisobutylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, and N,N,N',N'-tetramethyltetraethylenepentamine.

Examples of suitable mixed amines include dimethylethylamine, methylethylpropylamine, benzylamine, phenethylamine, and benzyldimethylamine.

Examples of suitable aromatic and heterocyclic amines include aniline derivatives (e.g., aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, and diaminonaphthalene; and pyrrole derivatives (e.g., pyrrole, 2H-pyrrole, 1-methylpyrrole, 2,4-dimethylpyrrole, 2,5-dimethylpyrrole, and N-methylpyrrole), oxazole derivatives (e.g., oxazole and isooxazole), thiazole derivatives (e.g., thiazole and isothiazole), imidazole derivatives (e.g., imidazole, 4-methylimidazole, and 4-methyl-2-phenylimidazole), pyrazole derivatives, furazan derivatives, pyrroline derivatives (e.g., pyrroline and 2-methyl-1-pyrroline), pyrrolidine derivatives (e.g., pyrrolidine, N-methylpyrrolidine, pyrrolidinone, and N-methylpyrrolidone), imidazoline derivatives, imidazolidine derivatives, pyridine derivatives (e.g., pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 4-pyrrolidinopyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (e.g., quinoline and 3-quinolinecarbonitrile), isoquinoline derivatives, cinnoline derivatives, quinazoline derivatives, quinoxaline derivatives, phthalazine derivatives, purine derivatives, pteridine derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Examples of suitable nitrogen-containing compounds having carboxyl group include aminobenzoic acid, indolecarboxylic acid, and amino acid derivatives (e.g., nicotinic acid, alanine, alginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine).

Examples of suitable nitrogen-containing compounds having sulfonyl group include 3-pyridinesulfonic acid and pyridinium p-toluenesulfonate.

Examples of suitable nitrogen-containing compounds having hydroxyl group, nitrogen-containing compounds having hydroxyphenyl group, and alcoholic nitrogen-containing compounds include 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, piperidine ethanol, 1-(2-hydroxyethyl)pyrrolidine, 1-(2-hydroxyethyl)-2-pyrrolidinone, 3-piperidino-1,2-propanediol, 3-pyrrolidino-1,2-propanediol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)isonicotinamide.

Examples of suitable amide derivatives include formamide, N-methylformamide, N,N-dimethylformamide, acetamide, N-methylacetamide, N,N-dimethylacetamide, propionamide, benzamide, and 1-cyclohexylpyrrolidone. Suitable imide derivatives include phthalimide, succinimide, and maleimide. Suitable carbamates include N-t-butoxycarbonyl-N,N-dicyclohexylamine, N-t-butoxycarbonylbenzimidazole, and oxazolidinone.

In addition, nitrogen-containing organic compounds of the following general formula (B)-1 may also be included alone or in admixture.

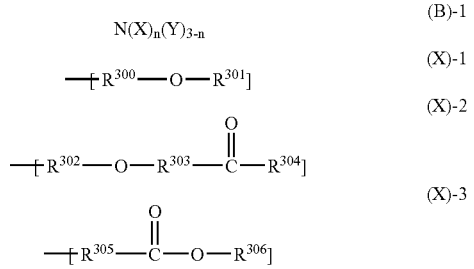

$$N(X)_n(Y)_{3-n} \quad \text{(B)-1}$$

$$\text{---}[R^{300}\text{---}O\text{---}R^{301}] \quad \text{(X)-1}$$

$$\text{---}[R^{302}\text{---}O\text{---}R^{303}\text{---}\overset{O}{\underset{\|}{C}}\text{---}R^{304}] \quad \text{(X)-2}$$

$$\text{---}[R^{305}\text{---}\overset{O}{\underset{\|}{C}}\text{---}O\text{---}R^{306}] \quad \text{(X)-3}$$

In the formulas, n is 1, 2 or 3. The side chain X may be the same or different and is represented by the formula (X)-1, (X)-2 or (X)-3. The side chain Y may be the same or different and stands for hydrogen or a straight, branched or cyclic alkyl group of 1 to 20 carbon atoms which may contain an ether or hydroxyl group. Two or three X's may bond together to form a ring. $R^{300}$, $R^{302}$ and $R^{305}$ are independently straight or branched alkylene groups of 1 to 4 carbon atoms; $R^{301}$ and $R^{304}$ are independently hydrogen or straight, branched or cyclic alkyl groups of 1 to 20 carbon atoms, which may contain at least one hydroxyl group, ether, ester or lactone ring; $R^{303}$ is a single bond or a straight or branched alkylene group of 1 to 4 carbon atoms; and $R^{306}$ is a straight, branched or cyclic alkyl group of 1 to 20 carbon atoms, which may contain at least one hydroxyl group, ether, ester or lactone ring.

Illustrative, non-limiting examples of the compounds of formula (B)-1 include tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl]amine, 4,7,13,16,21,24-hexaoxa-1,10-diazabicyclo[8.8.8]hexacosane, 4,7,13,18-tetraoxa-1,10-diazabicyclo[8.5.5]eicosane, 1,4,10,13-tetraoxa-7,16-diazabicyclooctadecane, 1-aza-12-crown-4, 1-aza-15-crown-5, 1-aza-18-crown-6, tris(2-formyloxyethyl)amine, tris(2-acetoxyethyl)amine, tris(2-propionyloxyethyl)amine, tris(2-butyryloxyethyl)amine, tris(2-isobutyryloxyethyl)amine, tris(2-valeryloxyethyl)amine, tris(2-pivaloyloxyethyl)amine, N,N-bis(2-acetoxyethyl)-2-(acetoxyacetoxy)ethylamine, tris(2-methoxycarbonyloxyethyl)amine, tris(2-tert-butoxycarbonyloxyethyl)amine, tris[2-(2-oxopropoxy)ethyl]amine, tris[2-(methoxycarbonylmethyl)oxyethyl]amine, tris[2-(tert-butoxycarbonylmethyloxy)ethyl]amine, tris[2-(cyclohexyloxycarbonylmethyloxy)ethyl]amine, tris(2-methoxycarbonylethyl)amine, tris(2-ethoxycarbonylethyl)amine, N,N-bis(2-hydroxyethyl)-2-(methoxycarbonyl)ethylamine, N,N-bis(2-acetoxyethyl)-2-(methoxycarbonyl)ethylamine, N,N-bis(2-hydroxyethyl)-2-(ethoxycarbonyl)ethylamine, N,N-bis(2-acetoxyethyl)-2-(ethoxycarbonyl)ethylamine, N,N-bis(2-hydroxyethyl)-2-(2-methoxyethoxycarbonyl)ethylamine, N,N-bis(2-acetoxyethyl)-2-(2-methoxyethoxycarbonyl)ethylamine, N,N-bis(2-hydroxyethyl)-2-(2-hydroxyethoxycarbonyl)ethylamine, N,N-bis(2-acetoxyethyl)-2-(2-acetoxyethoxycarbonyl)ethylamine, N,N-bis(2-hydroxyethyl)-2-[(methoxycarbonyl)methoxycarbonyl]-ethylamine, N,N-bis(2-acetoxyethyl)-2-[(methoxycarbonyl)methoxycarbonyl]-ethylamine, N,N-bis(2-hydroxyethyl)-2-(2-oxopropoxycarbonyl)ethylamine, N,N-bis(2-acetoxyethyl)-2-(2-oxopropoxycarbonyl)ethylamine, N,N-bis(2-hydroxyethyl)-2-(tetrahydrofurfuryloxycarbonyl)-ethylamine, N,N-bis(2-acetoxyethyl)-2-(tetrahydrofurfuryloxycarbonyl)-ethylamine, N,N-bis(2-hydroxyethyl)-2-[(2-oxotetrahydrofuran-3-yl)oxy-carbonyl]ethylamine, N,N-bis(2-acetoxyethyl)-2-[(2-oxotetrahydrofuran-3-yl)oxy-carbonyl]ethylamine, N,N-bis(2-hydroxyethyl)-2-(4-hydroxybutoxycarbonyl)ethylamine, N,N-bis(2-formyloxyethyl)-2-(4-formyloxybutoxycarbonyl)-ethylamine, N,N-bis(2-formyloxyethyl)-2-(2-formyloxyethoxycarbonyl)-ethylamine, N,N-bis(2-methoxyethyl)-2-(methoxycarbonyl)ethylamine, N-(2-hydroxyethyl)-bis[2-(methoxycarbonyl)ethyl]amine, N-(2-acetoxyethyl)-bis[2-(methoxycarbonyl)ethyl]amine, N-(2-hydroxyethyl)-bis[2-(ethoxycarbonyl)ethyl]amine, N-(2-acetoxyethyl)-bis[2-(ethoxycarbonyl)ethyl]amine, N-(3-hydroxy-1-propyl)-bis[2-(methoxycarbonyl)ethyl]amine, N-(3-acetoxy-1-propyl)-bis[2-(methoxycarbonyl)ethyl]amine, N-(2-methoxyethyl)-bis[2-(methoxycarbonyl)ethyl]amine, N-butyl-bis[2-(methoxycarbonyl)ethyl]amine, N-butyl-bis[2-(2-methoxyethoxycarbonyl)ethyl]amine, N-methyl-bis(2-acetoxyethyl)amine, N-ethyl-bis(2-acetoxyethyl)amine, N-methyl-bis(2-pivaloyloxyethyl)amine, N-ethyl-bis[2-(methoxycarbonyloxy)ethyl]amine, N-ethylbis[2-(tert-butoxycarbonyloxy)ethyl]amine, tris(methoxycarbonylmethyl)amine, tris(ethoxycarbonylmethyl)amine, N-butyl-bis(methoxycarbonylmethyl)amine, N-hexyl-bis (methoxycarbonylmethyl)amine, and β-(diethylamino)-δ-valerolactone.

Also useful are one or more of nitrogen-containing organic cyclic structure compounds having the following general formula (B)-2.

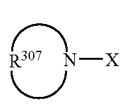

(B)-2

Herein X is as defined above, and $R^{307}$ is a straight or branched alkylene group of 2 to 20 carbon atoms which may contain one or more carbonyl, ether, ester or sulfide groups.

Illustrative examples of the compounds having formula (B)-2 include 1-[2-(methoxymethoxy)ethyl]pyrrolidine, 1-[2-(methoxymethoxy)ethyl]piperidine, 4-[2-(methoxymethoxy)ethyl]morpholine, 1-[2-[(2-methoxyethoxy)methoxy]ethyl]pyrrolidine, 1-[2-[(2-methoxyethoxy)methoxy]ethyl]piperidine, 4-[2-[(2-methoxyethoxy)methoxy]ethyl]morpholine, 2-(1-pyrrolidinyl)ethyl acetate, 2-piperidinoethyl acetate, 2-morpholinoethyl acetate, 2-(1-pyrrolidinyl)ethyl formate, 2-piperidinoethyl propionate, 2-morpholinoethyl acetoxyacetate, 2-(1-pyrrolidinyl)ethyl methoxyacetate, 4-[2-(methoxycarbonyloxy)ethyl]morpholine, 1-[2-(t-butoxycarbonyloxy)ethyl]piperidine, 4-[2-(2-methoxyethoxycarbonyloxy)ethyl]morpholine, methyl 3-(1-pyrrolidinyl)propionate, methyl 3-piperidinopropionate, methyl 3-morpholinopropionate, methyl 3-(thiomorpholino) propionate, methyl 2-methyl-3-(1-pyrrolidinyl)propionate, ethyl 3-morpholinopropionate, methoxycarbonylmethyl 3-piperidinopropionate, 2-hydroxyethyl 3-(1-pyrrolidinyl) propionate, 2-acetoxyethyl 3-morpholinopropionate, 2-oxotetrahydrofuran-3-yl 3-(1-pyrrolidinyl)propionate, tetrahydrofurfuryl 3-morpholinopropionate, glycidyl 3-piperidinopropionate, 2-methoxyethyl 3-morpholinopropionate, 2-(2-methoxyethoxy)ethyl 3-(1-pyrrolidinyl)propionate, butyl 3-morpholinopropionate, cyclohexyl 3-piperidinopropionate, α-(1-pyrrolidinyl)methyl-γ-butyrolactone, β-piperidino-γ-butyrolactone, β-morpholino-δ-valerolactone, methyl 1-pyrrolidinylacetate, methyl piperidinoacetate, methyl morpholinoacetate, methyl thiomorpholinoacetate, ethyl 1-pyrrolidinylacetate, and 2-methoxyethyl morpholinoacetate.

Also, one or more of nitrogen-containing compounds having cyano represented by the following general formulae (B)-3 to (B)-6 may be blended.

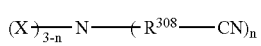

(B)-3

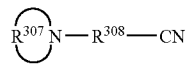

(B)-4

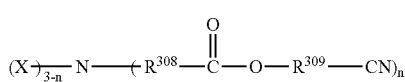

(B)-5

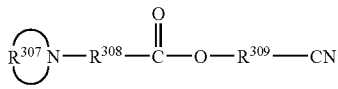

(B)-6

Herein, X, $R^{307}$ and n are as defined above, and $R^{308}$ and $R^{309}$ are each independently a straight or branched alkylene group of 1 to 4 carbon atoms.

Illustrative examples of the nitrogen-containing compounds having cyano as represented by formulae (B)-3 to (B)-6 include 3-(diethylamino)propiononitrile, N,N-bis(2-hydroxyethyl)-3-aminopropiononitrile, N,N-bis(2-acetoxyethyl)-3-aminopropiononitrile, N,N-bis(2-formyloxyethyl)-3-aminopropiononitrile, N,N-bis(2-methoxyethyl)-3-aminopropiononitrile, N,N-bis[2-(methoxymethoxy)ethyl]-3-aminopropiononitrile, methyl N-(2-cyanoethyl)-N-(2-methoxyethyl)-3-aminopropionate, methyl N-(2-cyanoethyl)-N-(2-hydroxyethyl)-3-aminopropionate, methyl N-(2-acetoxyethyl)-N-(2-cyanoethyl)-3-aminopropionate, N-(2-cyanoethyl)-N-ethyl-3-aminopropiononitrile, N-(2-cyanoethyl)-N-(2-hydroxyethyl)-3-aminopropiononitrile, N-(2-acetoxyethyl)-N-(2-cyanoethyl)-3-aminopropiononitrile, N-(2-cyanoethyl)-N-(2-formyloxyethyl)-3-aminopropiononitrile, N-(2-cyanoethyl)-N-(2-methoxyethyl)-3-aminopropiononitrile, N-(2-cyanoethyl)-N-[2-(methoxymethoxy)ethyl]-3-aminopropiononitrile, N-(2-cyanoethyl)-N-(3-hydroxy-1-propyl)-3-aminopropiononitrile, N-(3-acetoxy-1-propyl)-N-(2-cyanoethyl)-3-aminopropiononitrile, N-(2-cyanoethyl)-N-(3-formyloxy-1-propyl)-3-aminopropiononitrile, N-(2-cyanoethyl)-N-tetrahydrofurfuryl-3-aminopropiononitrile, N,N-bis(2-cyanoethyl)-3-aminopropiononitrile, diethylaminoacetonitrile, N,N-bis(2-hydroxyethyl)aminoacetonitrile, N,N-bis(2-acetoxyethyl)aminoacetonitrile, N,N-bis(2-formyloxyethyl)aminoacetonitrile, N,N-bis(2-methoxyethyl)aminoacetonitrile, N,N-bis[2-(methoxymethoxy) ethyl]aminoacetonitrile, methyl N-cyanomethyl-N-(2-methoxyethyl)-3-aminopropionate, methyl N-cyanomethyl-N-(2-hydroxyethyl)-3-aminopropionate, methyl N-(2-acetoxyethyl)-N-cyanomethyl-3-aminopropionate, N-cyanomethyl-N-(2-hydroxyethyl)aminoacetonitrile, N-(2-acetoxyethyl)-N-(cyanomethyl)aminoacetonitrile, N-cyanomethyl-N-(2-formyloxyethyl)aminoacetonitrile, N-cyanomethyl-N-(2-methoxyethyl)aminoacetonitrile, N-cyanomethyl-N-[2-(methoxymethoxy)ethyl]aminoacetonitrile, N-cyanomethyl-N-(3-hydroxy-1-propyl)aminoacetonitrile, N-(3-acetoxy-1-propyl)-N-(cyanomethyl)aminoacetonitrile, N-cyanomethyl-N-(3-formyloxy-1-propyl) aminoacetonitrile, N,N-bis(cyanomethyl)aminoacetonitrile, 1-pyrrolidinepropiononitrile, 1-piperidinepropiononitrile, 4-morpholinepropiononitrile, 1-pyrrolidineacetonitrile, 1-piperidineacetonitrile, 4-morpholineacetonitrile, cyanomethyl 3-diethylaminopropionate, cyanomethyl N,N-bis(2-hydroxyethyl)-3-aminopropionate, cyanomethyl N,N-bis(2-acetoxyethyl)-3-aminopropionate, cyanomethyl N,N-bis(2-formyloxyethyl)-3-aminopropionate, cyanomethyl N,N-bis (2-methoxyethyl)-3-aminopropionate, cyanomethyl N,N-bis [2-(methoxymethoxy)ethyl]-3-aminopropionate,
2-cyanoethyl 3-diethylaminopropionate, 2-cyanoethyl N,N-bis(2-hydroxyethyl)-3-aminopropionate, 2-cyanoethyl N,N-bis(2-acetoxyethyl)-3-aminopropionate, 2-cyanoethyl N,N-bis(2-formyloxyethyl)-3-aminopropionate, 2-cyanoethyl N,N-bis(2-methoxyethyl)-3-aminopropionate, 2-cyanoethyl N,N-bis[2-(methoxymethoxy)ethyl]-3-aminopropionate, cyanomethyl 1-pyrrolidinepropionate, cyanomethyl 1-piperidinepropionate, cyanomethyl 4-morpholinepropionate, 2-cyanoethyl 1-pyrrolidinepropionate, 2-cyanoethyl 1-piperidinepropionate, and 2-cyanoethyl 4-morpholinepropionate.

Also included are organic nitrogen-containing compounds having an imidazole skeleton and a polar functional group, represented by the general formula (B)-7.

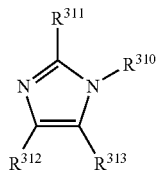
(B)-7

Herein, $R^{310}$ is a straight, branched or cyclic alkyl group of 2 to 20 carbon atoms bearing at least one polar functional group selected from among hydroxyl, carbonyl, ester, ether, sulfide, carbonate, cyano and acetal groups; $R^{311}$, $R^{312}$ and $R^{313}$ are each independently a hydrogen atom, a straight, branched or cyclic alkyl group, aryl group or aralkyl group having 1 to 10 carbon atoms.

Also included are organic nitrogen-containing compounds having a benzimidazole skeleton and a polar functional group, represented by the general formula (B)-8.

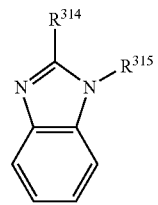
(B)-8

Herein, $R^{314}$ is a hydrogen atom, a straight, branched or cyclic alkyl group, aryl group or aralkyl group having 1 to 10 carbon atoms. $R^{315}$ is a polar functional group-bearing, straight, branched or cyclic alkyl group of 1 to 20 carbon atoms, and the alkyl group contains as the polar functional group at least one group selected from among ester, acetal and cyano groups, and may additionally contain at least one group selected from among hydroxyl, carbonyl, ether, sulfide and carbonate groups.

Further included are heterocyclic nitrogen-containing compounds having a polar functional group, represented by the general formulae (B)-9 and (B)-10.

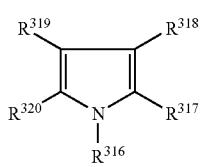
(B)-9

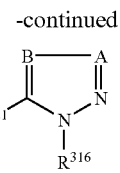
(B)-10

Herein, A is a nitrogen atom or $=\!\!C\!-\!R^{322}$, B is a nitrogen atom or $=\!\!C\!-\!R^{323}$, $R^{316}$ is a straight, branched or cyclic alkyl group of 2 to 20 carbon atoms bearing at least one polar functional group selected from among hydroxyl, carbonyl, ester, ether, sulfide, carbonate, cyano and acetal groups; $R^{317}$, $R^{318}$, $R^{319}$ and $R^{320}$ are each independently a hydrogen atom, a straight, branched or cyclic alkyl group or aryl group having 1 to 10 carbon atoms, or a pair of $R^{317}$ and $R^{318}$ and a pair of $R^{319}$ and $R^{320}$, taken together, may form a benzene, naphthalene or pyridine ring; $R^{321}$ is a hydrogen atom, a straight, branched or cyclic alkyl group or aryl group having 1 to 10 carbon atoms; $R^{322}$ and $R^{323}$ each are a hydrogen atom, a straight, branched or cyclic alkyl group or aryl group having 1 to 10 carbon atoms, or a pair of $R^{321}$ and $R^{323}$, taken together, may form a benzene or naphthalene ring.

Also included are nitrogen-containing organic compounds of aromatic carboxylic ester structure having the general formulae (B)-11 to (B)-14.

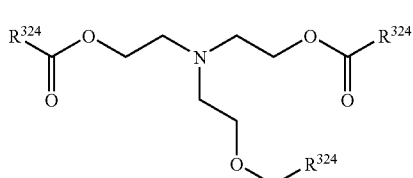
(B)-11

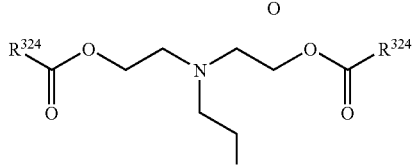
(B)-12

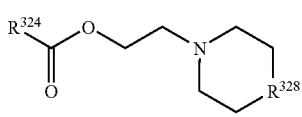
(B)-13

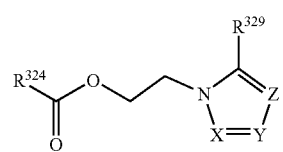
(B)-14

Herein $R^{324}$ is a $C_6$-$C_{20}$ aryl group or $C_4$-$C_{20}$ hetero-aromatic group, in which some or all of hydrogen atoms may be replaced by halogen atoms, straight, branched or cyclic $C_1$-$C_{20}$ alkyl groups, $C_6$-$C_{20}$ aryl groups, $C_7$-$C_{20}$ aralkyl groups, $C_1$-$C_{10}$ alkoxy groups, $C_1$-$C_{10}$ acyloxy groups or $C_1$-$C_{10}$ alkylthio groups. $R^{325}$ is $CO_2R^{326}$, $OR^{327}$ or cyano group. $R^{326}$ is a $C_1$-$C_{10}$ alkyl group, in which some methylene groups may be replaced by oxygen atoms. $R^{327}$ is a $C_1$-$C_{10}$ alkyl or acyl group, in which some methylene groups may be replaced by oxygen atoms. $R^{328}$ is a single bond, methylene, ethylene, sulfur atom or —O(CH$_2$CH$_2$O)$_n$— group wherein n is 0, 1, 2, 3 or 4. R$^{329}$ is hydrogen, methyl, ethyl or phenyl. X is a nitrogen atom or CR$^{330}$. Y is a nitrogen atom or CR$^{331}$. Z is a nitrogen atom or CR$^{332}$. R$^{330}$, R$^{331}$ and R$^{332}$ are each independently hydrogen, methyl or phenyl. Alternatively, a pair of R$^{330}$ and R$^{331}$ or a pair of R$^{331}$ and R$^{332}$ may bond together to form a C$_6$-C$_{20}$ aromatic ring or C$_2$-C$_{20}$ heteroaromatic ring.

Further included are nitrogen-containing organic compounds of 7-oxanorbornane-2-carboxylic ester structure having the general formula (B)-15.

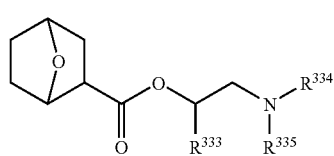

(B)-15

Herein R$^{333}$ is hydrogen or a straight, branched or cyclic C$_1$-C$_{10}$ alkyl group. R$^{334}$ and R$^{335}$ are each independently a C$_1$-C$_{20}$ alkyl group, C$_6$-C$_{20}$ aryl group or C$_1$-C$_{20}$ aralkyl group, which may contain one or more polar functional groups selected from among ether, carbonyl, ester, alcohol, sulfide, nitrile, amine, imine, and amide and in which some hydrogen atoms may be replaced by halogen atoms. R$^{334}$ and R$^{335}$, taken together, may form a heterocyclic or hetero-aromatic ring of 2 to 20 carbon atoms.

The organic nitrogen-containing compounds may be used alone or in admixture of two or more. The organic nitrogen-containing compound is preferably formulated in an amount of 0.001 to 2 parts, and especially 0.01 to 1 part by weight, per 100 parts by weight of the entire base resin. Less than 0.001 part of the nitrogen-containing compound achieves no or little addition effect whereas more than 2 parts would result in too low a sensitivity.

While the resist composition of the invention is basically composed of the inventive polymer, the photoacid generator, the organic solvent and optionally the nitrogen-containing organic compound as described above, it may further include any well-known components such as dissolution inhibitors, acidic compounds, stabilizers, dyes, and surfactants, if necessary.

Pattern formation using the resist composition of the invention may be carried out by a known lithographic technique. For example, the resist composition is applied onto a substrate such as a silicon wafer by spin coating or the like to form a resist film having a thickness of 0.3 to 2.0 μm, which is then pre-baked on a hot plate at 60 to 150° C. for 1 to 10 minutes, and preferably at 80 to 130° C. for 1 to 5 minutes. A patterning mask having the desired pattern is then placed over the resist film, and the film exposed through the mask to an electron beam or to high-energy radiation such as deep-UV radiation, excimer laser radiation or x-ray in a dose of about 1 to 200 mJ/cm$^2$, and preferably about 10 to 100 mJ/cm$^2$. The resist film is then post-exposure baked (PEB) on a hot plate at 60 to 150° C. for 1 to 5 minutes, and preferably at 80 to 130° C. for 1 to 3 minutes. Finally, development is carried out using as the developer an aqueous alkali solution, such as a 0.1 to 5 wt % (preferably 2 to 3 wt %) aqueous solution of tetramethylammonium hydroxide (TMAH), this being done by a conventional method such as dip, puddle, or spray development for a period of 0.1 to 3 minutes, and preferably 0.5 to 2 minutes. These steps result in the formation of the desired pattern on the substrate. Of the various types of high-energy radiation that may be used, the resist composition of the invention is best suited to fine pattern formation with deep-UV radiation or excimer laser radiation having a wavelength of 248 to 157 nm, x-rays, or electron beams. The invention is applicable to not only dry light exposure, but also light exposure by the immersion process.

Described below is a method of processing a substrate using the resist composition according to the bilayer resist process. A substrate to be processed is usually an inorganic substrate. An underlying film (or organic film) is formed on the substrate. The resist composition of the invention is applied onto the underlying film to form a resist coating. If necessary, an antireflective coating may be formed between the resist composition and the underlying film. The resist coating is patterned by the above-mentioned procedure, after which the pattern is transferred to the underlying film by oxygen gas etching using the resist pattern as an etching mask. The oxygen gas etching is reactive plasma etching using oxygen gas as a main component. With this method, silicon oxide having high resistance to oxygen gas etching is formed from the resist pattern, allowing the underlying organic film to be processed at a high aspect ratio. SO$_2$, CO$_2$, CO, NH$_3$ or N$_2$ gas may be added to the oxygen gas for protecting side walls for preventing the film from being configured to a T-top profile by over-etching. Prior to the oxygen gas etching, brief etching with a fluorocarbon gas may be carried out for removing any scum of the resist after development and smoothening line edges to prohibit roughening.

Subsequently, the processable film or substrate is subjected to dry etching. Etching with a fluorocarbon gas as a main component is carried out when the processable film is SiO$_2$ or Si$_3$N$_4$. Exemplary fluorocarbon gases are CF$_4$, CHF$_3$, CH$_2$F$_2$, C$_2$F$_6$, C$_3$F$_8$, C$_4$F$_{10}$ and C$_5$F$_{12}$. At the same time as the dry etching of the processable film, the silicon-containing resist film can be stripped off. Etching with chlorine or bromine gas as a main component is employed when the processable film is polysilicon, tungsten silicide, TiN/Al or the like.

In the bilayer resist process, the underlying film may be made of any organic material which is selected from a number of well-known organic film materials. As the organic film, aromatic resins are generally preferred, with those aromatic resins which can be crosslinked during film formation so as to prevent intermixing during coating and film formation of the resist composition thereon being especially preferred.

Suitable aromatic resins include novolac resins and polyhydroxystyrene resins. Aromatic resins further having a fluorene or indene skeleton are advantageously used to enhance the etching resistance of the organic film during etching of the substrate after the pattern has been transferred to the organic film. It is possible to form an antireflective coating on the organic film and to form a resist film of the invention thereon. If the organic film possesses an antireflective function, advantageously the overall process becomes simpler. To impart an antireflective function, an aromatic resin having an anthracene skeleton or naphthalene skeleton or benzene skeleton having a conjugated unsaturated bond is preferably used.

Crosslinks can be formed by a crosslinking method as employed for thermosetting resins and negative resist compositions. In general, a composition solution comprising a resin having functional groups such as phenol, alkoxyphenyl, alcohol or carboxylic acid, a material capable of thermal decomposition to generate an acid, and a crosslinker capable of forming crosslinks with the functional groups in the presence of an acid catalyst, such as hexaalkoxymethylmelamine is applied onto a processable substrate, and the coating is heated to generate an acid, with which crosslinks are formed.

EXAMPLE

Examples of the invention are given below by way of illustration and not by way of limitation.

Reference Example 1

Synthesis of 5,5-difluoro-6-(5-norbornen-2-yl)-4-trifluoromethyl-1,3-dioxan-4-ol (synthesis of dioxane hemiacetal monomer)

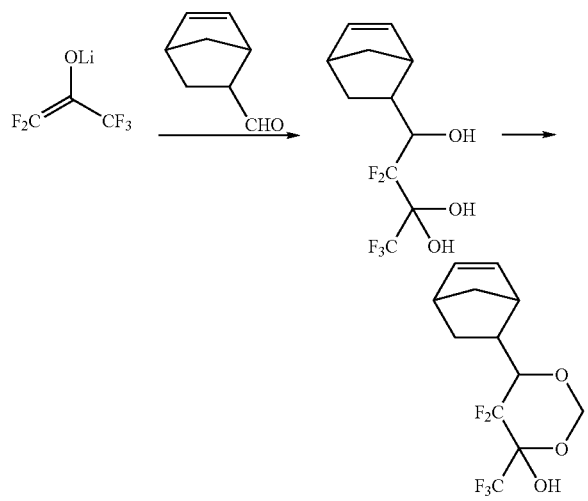

[1-1] Synthesis of 1-(5-norbornen-2-yl)-2,2,4,4,4-pentafluorobutane-1,3,3-triol

In a nitrogen atmosphere at −70° C., 1290 ml of 1.6M n-butyllithium in hexane was added to a mixture of 168 g of 1,1,1,3,3,3-hexafluoro-2-propanol and 1200 g of tetrahydrofuran. The mixture was allowed to warm up slowly to 0° C. and stirred at the temperature for 30 minutes. Then 134 g of 5-norbornene-2-carboxaldehyde was added at 0° C. The mixture was stirred for 1 hour, after which dilute hydrochloric acid was added for quenching and neutralization. This was followed by conventional aqueous work-up and purification by silica gel column chromatography, collecting 230 g of 1-(5-norbornen-2-yl)-2,2,4,4,4-pentafluorobutane-1,3,3-triol (yield 80% based on the 1,1,1,3,3,3-hexafluoro-2-propanol).

1-(5-norbornen-2-yl)-2,2,4,4,4-pentafluorobutane-1,3,3-triol

Colorless Solid
IR (KBr): ν=3409, 3288, 3062, 2979, 2946, 2923, 2879, 1486, 1454, 1423, 1338, 1311, 1255, 1241, 1207, 1172, 1153, 1112, 1076, 1025, 900, 842, 711 cm$^{-1}$
$^1$H-NMR (300 MHz in DMSO-d6, major diastereomer): δ=0.72 (1H, m), 1.18 (1H, br.d, J=8.0 Hz), 1.29 (1H, br.d, J=8.0 Hz), 1.74 (1H, ddd, J=12.0, 9.0, 3.7 Hz), 2.44 (1H, m), 2.77 (1H, m), 3.02 (1H, m), 3.52 (1H, ddd, J=22.0, 10.6, 7.4 Hz), 6.02 (1H, dd, J=5.7, 2.8 Hz), 6.19 (1H, dd, J=5.7, 3.0 Hz), 6.29 (1H, d, J=7.4 Hz), 7.37 (1H, s), 7.96 (1H, d, J=1.9 Hz) ppm
$^{19}$F-NMR (283 MHz in CDCl$_3$, major diastereomer): δ=−130.0 (1F), −120.6 (1F), −82.0 (3F) ppm

[1-2] Synthesis of 5,5-difluoro-6-(5-norbornen-2-yl)-4-trifluoromethyl-1,3-dioxan-4-ol A mixture of 40.0 g of the triol compound, an equivalent of keto-alcohol compound, obtained in [1-1], 3.4 g of a cation-exchange resin (sulfonic acid type), 15.0 g of s-trioxane, and 200 g of toluene was stirred for 24 hours at 60° C. The cation-exchange resin was filtered off, after which the reaction solution was directly purified by column chromatography, obtaining 32.1 g of 5,5-difluoro-6-(5-norbornen-2-yl)-4-trifluoromethyl-1,3-dioxan-4-ol (yield 76%).

5,5-difluoro-6-(5-norbornen-2-yl)-4-trifluoromethyl-1,3-dioxan-4-ol

Colorless Solid
IR (KBr): ν=3396, 3061, 3034, 3001, 2978, 2954, 2931, 2902, 2881, 1351, 1340, 1330, 1245, 1222, 1209, 1178, 1141, 1103, 1072, 1062, 1041, 993, 914, 844, 835, 732, 719, 690, 671, 649 cm$^{-1}$
$^1$H-NMR (600 MHz in DMSO-d6, major diastereomer): δ=0.75 (1H, ddd, J=11.6, 6.9, 3.8 Hz), 1.19 (1H, d, J=8.2 Hz), 1.29 (1H, dd, J=8.2, 1.4 Hz), 1.78 (1H, ddd, J=11.6, 9.3, 3.8 Hz), 2.43 (1H, dddd, J=10.7, 9.3, 3.8, 3.7 Hz), 2.81 (1H, m), 2.96 (1H, m), 3.38 (1H, dd, J=22.7, 10.7 Hz), 5.02 (2H, s), 5.97 (1H, dd, J=5.5, 2.8 Hz), 6.23 (1H, dd, J=5.5, 3.1 Hz), 8.94 (1H, d, J=3.1 Hz) ppm
$^{13}$C-NMR (150 MHz in DMSO-d6, major diastereomer): δ=28.16 (d, J=5 Hz), 35.62, 41.84, 43.37, 47.35, 77.66 (dd, J=25, 22 Hz), 85.96, 91.77 (dquint-like, J=23, 31 Hz), 113.68 (dd, J=261, 255 Hz), 121.17 (q, J=287 Hz), 132.00, 138.06 ppm
$^{19}$F-NMR (565 MHz in DMSO-d6, major diastereomer): δ=−131.21 (1F, ddq, J=247, 24, 14 Hz), −122.51 (1F, dm, J=247 Hz), −80.40 (3F, dd, J=14, 7 Hz) ppm Reference Example 2

Synthesis of 4,4-difluoro-5-hydroxy-3-methyl-5-trifluoromethyltetrahydrofuran-3-yl 5-norbornene-2-carboxylate

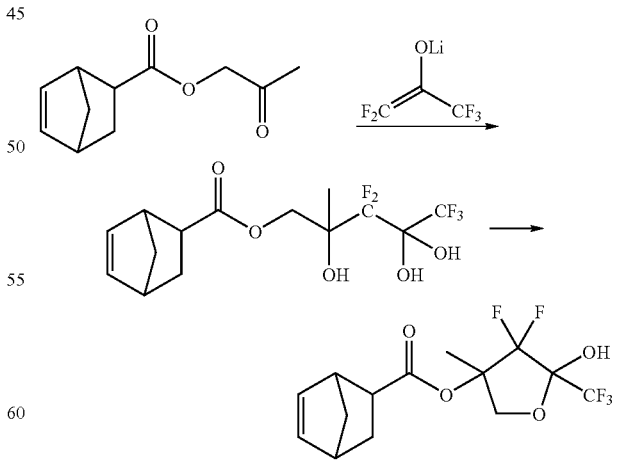

In a nitrogen atmosphere at 5° C., 100 ml of 1.6M n-butyllithium in hexane was added to a mixture of 21.7 g of 1,1,1,3,3,3-hexafluoro-2-propanol and 120 g of tetrahydrofuran. The mixture was stirred at 5° C. for 1 hour. Then a dilution of 22.8 g of 2-oxopropyl 5-norbornene-2-carboxylate in 30 g of tetrahydrofuran was added at 5° C. The mixture was stirred for 15 hours, after which dilute hydrochloric acid was added for quenching and neutralization. This was followed by conventional aqueous work-up and recrystallization from hexane for purification, collecting 24.6 g of 2-methyl-3,3,5,5,5-pentafluoro-2,4,4-trihydroxypentyl 5-norbornene-2-carboxylate (yield 58%).

A mixture of 10.1 g of the thus obtained 2-methyl-3,3,5,5,5-pentafluoro-2,4,4-trihydroxypentyl 5-norbornene-2-carboxylate, 3.3 g of triethylamine, and 30 g of toluene was stirred for 12 hours at 40° C. in a nitrogen atmosphere and further heated at 80° C. for 6 hours, after which dilute hydrochloric acid was added for quenching and neutralization. This was followed by conventional aqueous work-up and distillation for purification, collecting 7.4 g of 4,4-difluoro-5-hydroxy-3-methyl-5-trifluoromethyl-tetrahydrofuran-3-yl 5-norbornene-2-carboxylate (yield 75% based on the 2-methyl-3,3,5,5,5-pentafluoro-2,4,4-trihydroxypentyl 5-norbornene-2-carboxylate).

4,4-difluoro-5-hydroxy-3-methyl-5-trifluoromethyl-tetrahydrofuranyl 5-norbornene-2-carboxylate Yellow Liquid
boiling point 110° C. (40 Pa)
IR (KBr): ν=3399, 3064, 2981, 2906, 2879, 1741, 1627, 1571, 1452, 1386, 1336, 1274, 1201, 1168, 1130, 1110, 1097, 1066, 1024, 995, 908, 862, 838, 815, 777, 740, 715, 694, 653, 619, 538 cm$^{-1}$
$^1$H-NMR (600 MHz in DMSO-d6, mixture of four diastereomers): δ=1.20-2.25 (7H, m), 2.85-2.95 (1H, m), 2.95-3.20 (2H, m), 4.05-4.40 (2H, m), 5.80-6.20 (2H, m), 8.75 (1H, br.s) ppm
$^{19}$F-NMR (565 MHz in DMSO-d6, mixture of four diastereomers): δ=-125.2--122.3 (1F), -123.1--118.6 (1F), -80.8--80.5 (3F) ppm Example 1

Synthesis of a mixture (Silane Monomer 1) of 5,5-difluoro-6-[5-(trimethoxysilyl)norbornan-2-yl]-4-trifluoromethyl-1,3-dioxan-4-ol and 5,5-difluoro-6-[6-(trimethoxysilyl)norbornan-2-yl]-4-trifluoromethyl-1,3-dioxan-4-ol

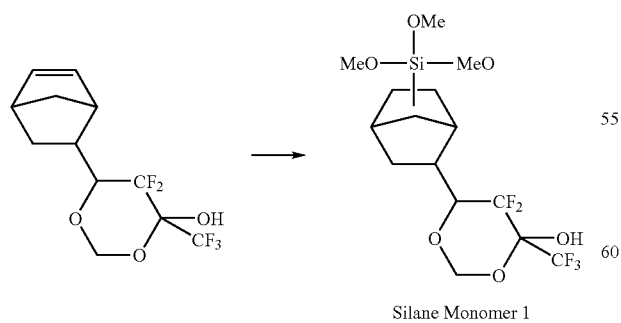

Silane Monomer 1

A mixture of 50.0 g of 5,5-difluoro-6-(5-norbornen-2-yl)-4-trifluoromethyl-1,3-dioxan-4-ol, 2.0 g of a 5% isopropyl alcohol solution of chloroplatinic acid, and 22.4 g of trimethoxysilane was heated and stirred at 80° C. in a nitrogen atmosphere. After the completion of reaction, low-boiling fractions were distilled off under reduced pressure, and thin-film distillation was subsequently performed. There was obtained 50.6 g of the target compound (yield 72%).

A mixture of 5,5-difluoro-6-[5-(trimethoxysilyl)-norbornan-2-yl]-4-trifluoromethyl-1,3-dioxan-4-ol and 5,5-difluoro-6-[6-(trimethoxysilyl)norbornan-2-yl]-4-trifluoromethyl-1,3-dioxan-4-ol GC-MS (EI): (m/z)$^+$=31, 66, 91, 121, 141, 187, 215, 277, 360, 390, 422 [M$^+$]
GC-MS (CI, methane): (m/z)$^+$=79, 121, 141, 159, 187, 215, 235, 253, 373, 393, 423 [(M+H)$^+$]

Example 2

Synthesis of a mixture (Silane Monomer 2) of 5,5-difluoro-6-[5-(triethoxysilyl)norbornan-2-yl]-4-trifluoromethyl-1,3-dioxan-4-ol and 5,5-difluoro-6-[6-(triethoxysilyl)norbornan-2-yl]-4-trifluoromethyl-1,3-dioxan-4-ol

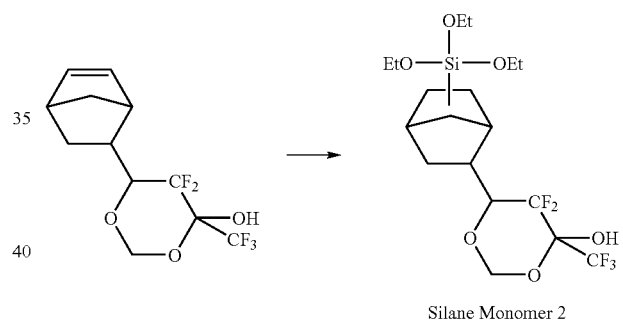

Silane Monomer 2

A mixture of 50.0 g of 5,5-difluoro-6-(5-norbornen-2-yl)-4-trifluoromethyl-1,3-dioxan-4-ol, 2.0 g of a 5% isopropyl alcohol solution of chloroplatinic acid, and 30.1 g of triethoxysilane was heated and stirred at 80° C. in a nitrogen atmosphere. After the completion of reaction, low-boiling fractions were distilled off under reduced pressure, and thin-film distillation was subsequently performed. There was obtained 57.3 g of the target compound (yield 74%).

A mixture of 5,5-difluoro-6-[5-(triethoxysilyl)norbornan-2-yl]-4-trifluoromethyl-1,3-dioxan-4-ol and 5,5-difluoro-6-[6-(triethoxysilyl)norbornan-2-yl]-4-trifluoromethyl-1,3-dioxan-4-ol GC-MS (EI): (m/z)$^+$=29, 55, 79, 119, 163, 193, 229, 388, 418, 464 [M$^+$]
GC-MS (CI, methane): (m/z)$^+$=79, 107, 129, 163, 183, 217, 237, 257, 287, 343, 389, 435, 465 [(M+H)$^+$]

Example 3

Synthesis of a mixture (Silane Monomer 3) of 4,4-difluoro-5-hydroxy-3-methyl-5-trifluoromethyltetrahydrofuranyl 5-trimethoxysilylnorbornane-2-carboxylate and 4,4-difluoro-5-hydroxy-3-methyl-5-trifluoromethyltetrahydrofuranyl 6-trimethoxysilylnorbornane-2-carboxylate

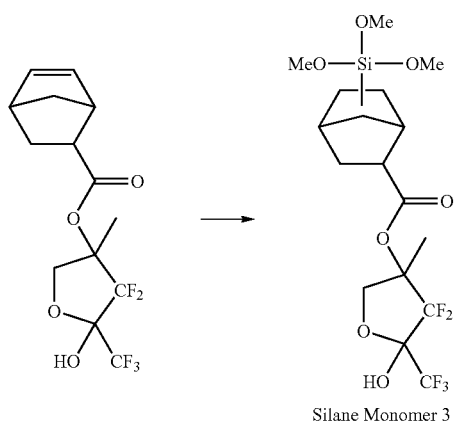

Silane Monomer 3

A mixture of 57.0 g of 4,4-difluoro-5-hydroxy-3-methyl-5-trifluoromethyltetrahydrofuranyl 5-norbornene-2-carboxylate, 2.0 g of a 5% isopropyl alcohol solution of chloroplatinic acid, and 22.4 g of trimethoxysilane was heated and stirred at 80° C. in a nitrogen atmosphere. After the completion of reaction, low-boiling fractions were distilled off under reduced pressure, and thin-film distillation was subsequently performed. There was obtained 51.9 g of the target compound (yield 67%).

Example 4

Synthesis of a mixture (Silane Monomer 4) of 4,4-difluoro-5-hydroxy-3-methyl-5-trifluoromethyltetrahydrofuranyl 5-triethoxysilylnorbornane-2-carboxylate and 4,4-difluoro-5-hydroxy-3-methyl-5-trifluoromethyltetrahydrofuranyl 6-triethoxysilylnorbornane-2-carboxylate

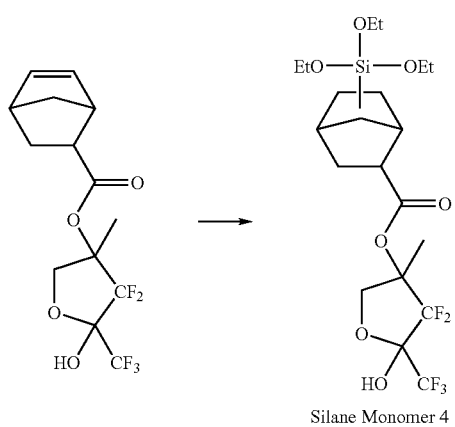

Silane Monomer 4

A mixture of 57.0 g of 4,4-difluoro-5-hydroxy-3-methyl-5-trifluoromethyltetrahydrofuranyl 5-norbornene-2-carboxylate, 2.0 g of a 5% isopropyl alcohol solution of chloroplatinic acid, and 30.1 g of triethoxysilane was heated and stirred at 80° C. in a nitrogen atmosphere. After the completion of reaction, low-boiling fractions were distilled off under reduced pressure, and thin-film distillation was subsequently performed. There was obtained 58.3 g of the target compound (yield 69%).

Example 5

Synthesis of Polymer 1

A 200-ml four-necked flask equipped with a stirrer, reflux condenser, dropping funnel and thermometer was charged with 0.2 g of acetic acid, 20 g of water and 20 g of ethanol and kept at 30° C. To the flask, a solution of 9.3 g (20 mmol) Silane Monomer 2, 10.8 g (30 mmol) Silane Monomer 5, and 16.4 g (50 mmol) Silane Monomer 8 in 40 g ethanol was added dropwise over 3 hours. Subsequently the reaction mixture was aged at 30° C. for 20 hours. The reaction mixture was diluted with methyl isobutyl ketone, washed with water repeatedly until the organic layer became neutral, and concentrated, obtaining 28.2 g of an oligomer.

Using 50 g of toluene, the oligomer was poured into a 100-ml three-necked flask equipped with a stirrer, reflux condenser, and thermometer. With 56 mg of potassium hydroxide added, the liquid was heated under reflux for 20 hours. The reaction solution was cooled, diluted with methyl isobutyl ketone, washed with water repeatedly until the organic layer became neutral, and concentrated, obtaining 25.1 g of a polymer.

On NMR and GPC analysis, this polymer was identified to be Polymer 1 of the following formula with a weight average molecular weight (Mw) of 3,100.

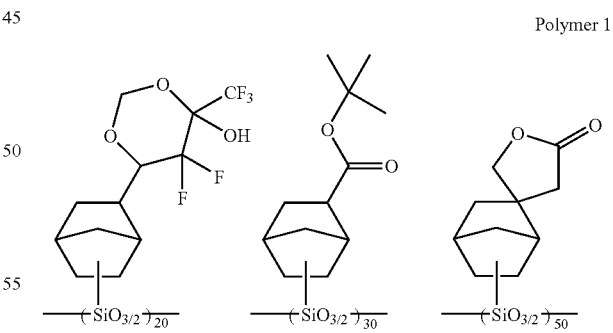

Polymer 1

Examples 6-18 and Comparative Examples 1-2

A series of polysiloxane compounds (Polymers 2 to 16) were prepared by the same procedure as in Example 5 aside from using silane monomers in combination as shown in Table 1.

TABLE 1

| | Polymer | Silane Monomers | | | | Yield (g) | Mw |
|---|---|---|---|---|---|---|---|
| Example 5 | Polymer 1 | Monomer 2 20 mmol | Monomer 5 30 mmol | Monomer 8 50 mmol | | 25.1 | 3,100 |
| Example 6 | Polymer 2 | Monomer 4 20 mmol | Monomer 7 25 mmol | Monomer 9 55 mmol | | 25.9 | 3,450 |
| Example 7 | Polymer 3 | Monomer 2 60 mmol | Monomer 5 40 mmol | | | 30.3 | 2,900 |
| Example 8 | Polymer 4 | Monomer 4 70 mmol | Monomer 5 30 mmol | | | 34 | 3,000 |
| Example 9 | Polymer 5 | Monomer 2 30 mmol | Monomer 5 30 mmol | Monomer 11 40 mmol | | 26.9 | 2,400 |
| Example 10 | Polymer 6 | Monomer 2 20 mmol | Monomer 5 30 mmol | Monomer 8 30 mmol | Monomer 11 20 mmol | 25 | 2,700 |
| Example 11 | Polymer 7 | Monomer 2 40 mmol | Monomer 6 30 mmol | Monomer 10 30 mmol | | 29.2 | 3,000 |
| Example 12 | Polymer 8 | Monomer 2 40 mmol | Monomer 6 20 mmol | Monomer 12 40 mmol | | 29.6 | 3,050 |
| Example 13 | Polymer 9 | Monomer 4 10 mmol | Monomer 7 40 mmol | Monomer 8 50 mmol | | 25.6 | 3,350 |
| Example 14 | Polymer 10 | Monomer 4 40 mmol | Monomer 5 30 mmol | Monomer 13 30 mmol | | 29 | 3,100 |
| Example 15 | Polymer 11 | Monomer 2 20 mmol | Monomer 7 30 mmol | Monomer 9 40 mmol | Monomer 13 10 mmol | 26.6 | 3,200 |
| Example 16 | Polymer 12 | Monomer 4 10 mmol | Monomer 5 40 mmol | Monomer 10 40 mmol | Monomer 14 10 mmol | 26.1 | 3,150 |
| Example 17 | Polymer 13 | Monomer 2 20 mmol | Monomer 7 25 mmol | Monomer 12 35 mmol | Monomer 15 20 mmol | 22.4 | 4,300 |
| Example 18 | Polymer 14 | Monomer 4 30 mmol | Monomer 7 30 mmol | Monomer 9 10 mmol | Monomer 15 30 mmol | 23.9 | 6,500 |
| Comparative Example 1 | Polymer 15 | Monomer 5 40 mmol | Monomer 9 60 mmol | | | 21.9 | 3,050 |
| Comparative Example 2 | Polymer 16 | Monomer 7 30 mmol | Monomer 8 70 mmol | | | 24.0 | 3.400 |

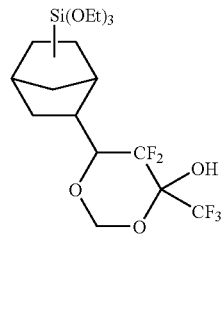

Silane Monomer 2

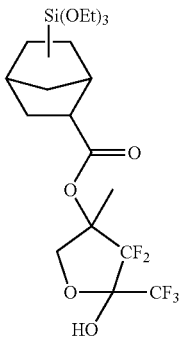

Silane Monomer 4

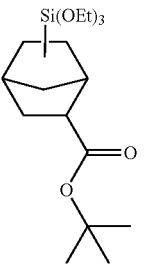

Silane Monomer 5

Silane Monomer 6

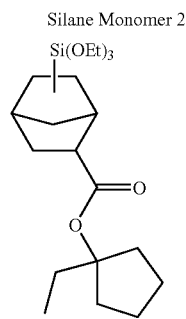

Silane Monomer 7

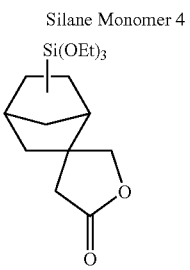

Silane Monomer 8

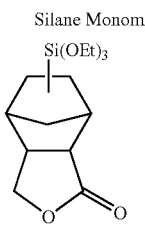

Silane Monomer 9

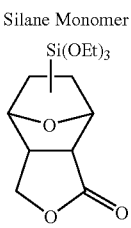

Silane Monomer 10

TABLE 1-continued

| Polymer | Silane Monomers | | | Yield (g) | Mw |
|---|---|---|---|---|---|
| | Silane Monomer 11: MeSi(OEt)₂ with spiro bicyclic lactone structure | Silane Monomer 12: Si(OEt)₃ with bicyclic anhydride structure | Silane Monomer 13: Si(OEt)₃ with bicyclic-CH₂-C(CF₃)₂OH structure | Silane Monomer 14: Si(OEt)₃ with bicyclic-C(CF₃)₂OH structure | |

Silane Monomer 15: (EtO)₃SiMe

Note that Me is methyl and Et is ethyl.

Resist Preparation

A positive resist film-forming solution was prepared by dissolving each polysiloxane of Examples 5 to 18 and Comparative Examples 1 to 2, a photoacid generator, a basic compound, and a surfactant as shown in Table 2 in propylene glycol monomethyl ether acetate (PGMEA) and filtering through a filter with a pore diameter of 0.2 μm.

The resist solution was spin-coated on a silicon wafer having an antireflective coating (DUV-30J by Nissan Chemical Industries Ltd., 55 nm) coated thereon, and baked at 110° C. for 90 seconds to form a resist film of 200 nm thick. The resist film was exposed on an ArF excimer laser stepper NSR-S305B (Nikon Corp., NA=0.68, σ=0.85), baked at 90° C. for 90 seconds, and developed in a 2.38 wt % tetramethylammonium hydroxide aqueous solution for 60 seconds, forming a positive pattern.

Evaluation

The resist pattern was evaluated as follows. The optimum dose (Eop, mJ/cm²) is defined as the dose which provides a 1:1 resolution at the top and bottom of a 0.18 μm line-and-space pattern. The resolution is defined as the minimum line width (μm) of the lines and spaces that separate at this dose. The results are shown in Table 2. It was demonstrated that the radiation-sensitive resin compositions within the scope of the invention had a high resolution upon ArF excimer laser exposure.

TABLE 2

| | Polymer (pbw) | Photoacid generator (pbw) | Base (pbw) | Solvent (pbw) | Sensitivity (mJ/cm²) | Resolution (nm) |
|---|---|---|---|---|---|---|
| Example 5 | Polymer 1 (100) | PAG1 (2) | tributylamine (0.1) | PGMEA (900) | 40 | 100 |
| Example 6 | Polymer 2 (100) | PAG1 (2) | tributylamine (0.1) | PGMEA (900) | 31 | 95 |
| Example 7 | Polymer 3 (100) | PAG1 (2) | tributylamine (0.1) | PGMEA (900) | 39 | 105 |
| Example 8 | Polymer 4 (100) | PAG1 (2) | tributylamine (0.1) | PGMEA (900) | 41 | 100 |
| Example 9 | Polymer 5 (100) | PAG1 (2) | tributylamine (0.1) | PGMEA (900) | 38 | 105 |
| Example 10 | Polymer 6 (100) | PAG1 (2) | tributylamine (0.1) | PGMEA (900) | 39 | 105 |
| Example 11 | Polymer 7 (100) | PAG1 (2) | tributylamine (0.1) | PGMEA (900) | 37 | 100 |
| Example 12 | Polymer 8 (100) | PAG1 (2) | tributylamine (0.1) | PGMEA (900) | 38 | 100 |
| Example 13 | Polymer 9 (100) | PAG1 (2) | tributylamine (0.1) | PGMEA (900) | 28 | 95 |
| Example 14 | Polymer 10 (100) | PAG1 (2) | tributylamine (0.1) | PGMEA (900) | 40 | 100 |
| Example 15 | Polymer 11 (100) | PAG1 (2) | tributylamine (0.1) | PGMEA (900) | 30 | 95 |
| Example 16 | Polymer 12 (100) | PAG1 (2) | tributylamine (0.1) | PGMEA (900) | 39 | 105 |
| Example 17 | Polymer 13 (100) | PAG1 (2) | tributylamine (0.1) | PGMEA (900) | 30 | 95 |
| Example 18 | Polymer 14 (100) | PAG1 (2) | tributylamine (0.1) | PGMEA (900) | 29 | 95 |
| Comparative Example 1 | Polymer 15 (100) | PAG1 (2) | tributylamine (0.1) | PGMEA (900) | 41 | 120 |

TABLE 2-continued

| | Polymer (pbw) | Photoacid generator (pbw) | Base (pbw) | Solvent (pbw) | Sensitivity (mJ/cm$^2$) | Resolution (nm) |
|---|---|---|---|---|---|---|
| Comparative Example 2 | Polymer 16 (100) | PAG1 (2) | tributylamine (0.1) | PGMEA (900) | 32 | 115 |

The photoacid generators in Table 2 are as follows.
PAG-1: triphenylsulfonium nonafluoro-n-butanesulfonate
PAG-2: diphenyliodonium nonafluoro-n-butanesulfonate It is seen from Tables 1 and 2 that the resist compositions comprising polymers containing silicon compounds within the scope of the invention succeed in significantly improving threshold resolution by preventing the patterns from being collapsed by swelling. Due to a very high transmittance in the VUV region, the compositions are promising in the F$_2$ or ArF lithography.

Japanese Patent Application No. 2005-198609 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A silicon compound bearing a fluorinated cyclic structure, having the general formula (1):

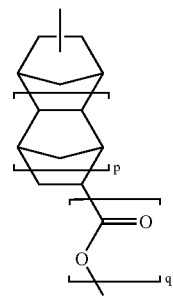

(1)

wherein X$^1$, X$^2$ and X$^3$ each are hydrogen, hydroxyl, halogen, a straight, branched or cyclic alkoxy group of 1 to 6 carbon atoms, or a monovalent organic group of 1 to 20 carbon atoms having a straight, branched, cyclic or polycyclic skeleton (excluding alkoxy), Y is a single bond or a divalent organic group, and Z is a trivalent organic group.

2. The silicon compound bearing a fluorinated cyclic structure of claim 1 wherein Y is a divalent organic group having an aliphatic ring.

3. The silicon compound bearing a fluorinated cyclic structure of claim 1 wherein Y is a divalent organic group having the general formula:

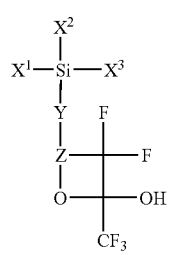

wherein p and q are each independently 1 or 0.

4. A silicon compound bearing a fluorinated cyclic structure, having the general formula (2), (3) or (4):

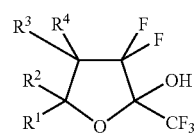

(2)

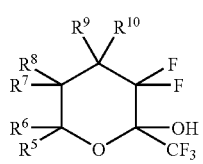

(3)

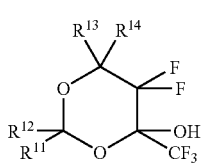

(4)

wherein at least one of R$^1$, R$^2$, R$^3$ and R$^4$ is a silicon-containing substituent group of the general formula:

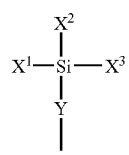

wherein X$^1$, X$^2$ and X$^3$ each are hydrogen, hydroxyl, halogen, a straight, branched or cyclic alkoxy group of 1 to 6 carbon atoms, or a monovalent organic group of 1 to 20 carbon atoms having a straight, branched, cyclic or polycyclic skeleton (excluding alkoxy), and Y is a single bond or a divalent organic group, and each of the remaining R$^1$ to R$^4$ is independently hydrogen, hydroxyl, halogen, or a monovalent organic group of 1 to 20 carbon atoms having a straight, branched, cyclic or polycyclic skeleton, or a combination of any two or more of $R^1$, $R^2$, $R^3$ and $R^4$ may bond together to form a ring with the carbon atom or atoms to which they are attached;

at least one of $R^5$, $R^6$, $R^7$, $R^8$, $R^9$ and $R^{10}$ is a silicon-containing substituent group of the general formula:

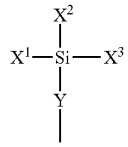

wherein $X^1$, $X^2$ and $X^3$ each are hydrogen, hydroxyl, halogen, a straight, branched or cyclic alkoxy group of 1 to 6 carbon atoms, or a monovalent organic group of 1 to 20 carbon atoms having a straight, branched, cyclic or polycyclic skeleton (excluding alkoxy), and Y is a single bond or a divalent organic group, and each of the remaining $R^5$ to $R^{10}$ is independently hydrogen, hydroxyl, halogen, or a monovalent organic group of 1 to 20 carbon atoms having a straight, branched, cyclic or polycyclic skeleton, or a combination of any two or more of $R^5$ to $R^{10}$ may bond together to form a ring with the carbon atom or atoms to which they are attached;

at least one of $R^{11}$, $R^{12}$, $R^{13}$ and $R^{14}$ is a silicon-containing substituent group of the general formula:

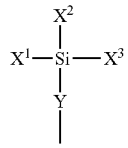

wherein $X^1$, $X^2$ and $X^3$ each are hydrogen, hydroxyl, halogen, a straight, branched or cyclic alkoxy group of 1 to 6 carbon atoms, or a monovalent organic group of 1 to 20 carbon atoms having a straight, branched, cyclic or polycyclic skeleton (excluding alkoxy), and Y is a single bond or a divalent organic group, and each of the remaining $R^{11}$ to $R^{14}$ is independently hydrogen, hydroxyl, halogen, or a monovalent organic group of 1 to 20 carbon atoms having a straight, branched, cyclic or polycyclic skeleton, or a combination of any two or more of $R^{11}$, $R^{12}$, $R^{13}$ and $R^{14}$ may bond together to form a ring with the carbon atom or atoms to which they are attached.

5. The silicon compound bearing a fluorinated cyclic structure of claim 4 wherein Y is a divalent organic group having an aliphatic ring.

6. The silicon compound bearing a fluorinated cyclic structure of claim 4 wherein Y is a divalent organic group having the general formula:

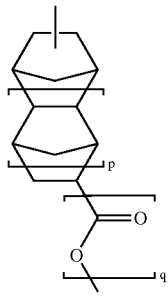

wherein p and q are each independently 1 or 0.

7. A fluorinated cyclic structure-bearing silicone resin comprising a partial structure having the general formula (1a), (2a), (3a) or (4a):

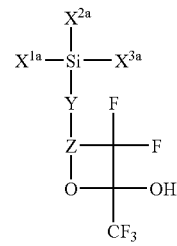

(1a)

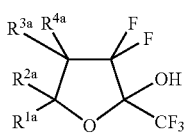

(2a)

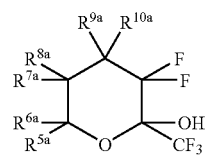

(3a)

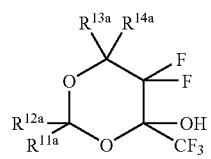

(4a)

wherein Y is a single bond or a divalent organic group, Z is a trivalent organic group, at least one of $X^{1a}$, $X^{2a}$ and $X^{3a}$ is an oxygen atom, and the remaining is hydrogen, hydroxyl, halogen, a straight, branched or cyclic alkoxy group of 1 to 6 carbon atoms, or a monovalent organic group of 1 to 20 carbon atoms having a straight, branched, cyclic or polycyclic skeleton (excluding alkoxy), at least one of $R^{1a}$, $R^{2a}$, $R^{3a}$ and $R^{4a}$ is a silicon-containing substituent group of the general formula:

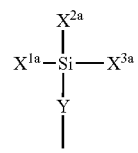

wherein at least one of $X^{1a}$, $X^{2a}$ and $X^{3a}$ is an oxygen atom and the remaining is hydrogen, hydroxyl, halogen, a straight, branched or cyclic alkoxy group of 1 to 6 carbon atoms, or a monovalent organic group of 1 to 20 carbon atoms having a straight, branched, cyclic or polycyclic skeleton (excluding alkoxy), and Y is as defined above, and each of the remaining $R^{1a}$ to $R^{4a}$ is independently hydrogen, hydroxyl, halogen, or a monovalent organic group of 1 to 20 carbon atoms having a straight, branched, cyclic or polycyclic skeleton, or a combination of any two or more of $R^{1a}$ to $R^{4a}$ may bond together to form a ring with the carbon atom or atoms to which they are attached;

at least one of $R^{5a}$, $R^{6a}$, $R^{7a}$, $R^{8a}$, $R^{9a}$ and $R^{10a}$ is a silicon-containing substituent group of the general formula:

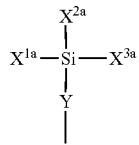

wherein at least one of $X^{1a}$, $X^{2a}$ and $X^{3a}$ is an oxygen atom and the remaining is hydrogen, hydroxyl, halogen, a straight, branched or cyclic alkoxy group of 1 to 6 carbon atoms, or a monovalent organic group of 1 to 20 carbon atoms having a straight, branched, cyclic or polycyclic skeleton (excluding alkoxy), and Y is as defined above, and each of the remaining $R^{5a}$ to $R^{10a}$ is independently hydrogen, hydroxyl, halogen, or a monovalent organic group of 1 to 20 carbon atoms having a straight, branched, cyclic or polycyclic skeleton, or a combination of any two or more of $R^{5a}$ to $R^{10a}$ may bond together to form a ring with the carbon atom or atoms to which they are attached;

at least one of $R^{11a}$, $R^{12a}$, $R^{13a}$ and $R^{14a}$ is a silicon-containing substituent group of the general formula:

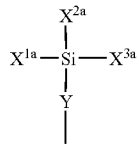

wherein at least one $X^{1a}$, $X^{2a}$ and $X^{3a}$ is an oxygen atom and the remaining is hydrogen, hydroxyl, halogen, a straight, branched or cyclic alkoxy group of 1 to 6 carbon atoms, or a monovalent organic group of 1 to 20 carbon atoms having a straight, branched, cyclic or polycyclic skeleton (excluding alkoxy), and Y is as defined above, and each of the remaining $R^{11a}$ to $R^{14a}$ is independently hydrogen, hydroxyl, halogen, or a monovalent organic group of 1 to 20 carbon atoms having a straight, branched, cyclic or polycyclic skeleton, or a combination of any two or more of $R^{11a}$ to $R^{14a}$ may bond together to form a ring with the carbon atom or atoms to which they are attached.

8. A resist composition comprising
(A) the silicone resin of claim 7,
(B) a photoacid generator, and
(C) a solvent.

9. A patterning process comprising the steps of:
applying the resist composition of claim 8 onto a substrate to form a resist layer,
heat treating the resist layer and exposing it to high energy radiation having a wavelength of up to 300 nm or electron beam through a photomask, and
optionally heat treating the exposed resist layer, and developing it with a developer.

10. The fluorinated cyclic structure-bearing silicone resin of claim 7 wherein Y is a divalent organic group having an aliphatic ring.

11. The fluorinated cyclic structure-bearing silicone resin of claim 7 wherein Y is a divalent organic group having the general formula:

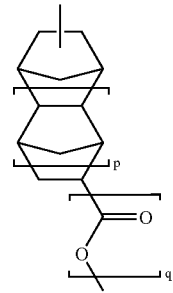

wherein p and q are each independently 1 or 0.

* * * * *